United States Patent
Koyama et al.

(10) Patent No.: US 7,605,183 B2
(45) Date of Patent: *Oct. 20, 2009

(54) INHIBITORY OR BLOCKING AGENTS OF MOLECULAR GENERATING AND/OR INDUCING FUNCTIONS

(76) Inventors: Shozo Koyama, 48-2 Oazasatoyamabe, Matsumoto-shi, Nagano (JP); Yoshihiro Yamaguchi, Manjuzukashukusha 3, 7-4, Arigasaki 3-chome, Matsumoto-shi, Nagano (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/889,162

(22) Filed: Aug. 9, 2007

(65) Prior Publication Data

US 2008/0200558 A1    Aug. 21, 2008

Related U.S. Application Data

(60) Division of application No. 11/513,174, filed on Aug. 31, 2006, now abandoned, which is a continuation of application No. 10/718,854, filed on Nov. 24, 2003, now abandoned, which is a division of application No. 10/029,259, filed on Dec. 28, 2001, now Pat. No. 6,710,090, which is a division of application No. 08/813,842, filed on Mar. 7, 1997, now Pat. No. 6,346,551, which is a continuation of application No. PCT/JP95/01783, filed on Sep. 7, 1995, now abandoned.

(30) Foreign Application Priority Data

Sep. 9, 1994    (JP)    ................................ 6-252660

(51) Int. Cl.
*A61K 31/122*    (2006.01)
*C07C 49/607*    (2006.01)

(52) U.S. Cl. ...................................... 514/690; 568/377

(58) Field of Classification Search ................ 568/377; 514/690

See application file for complete search history.

(56) References Cited

U.S. PATENT DOCUMENTS

| | | | |
|---|---|---|---|
| 6,346,551 B1 | 2/2002 | Koyoma et al. | ............. 514/690 |
| 6,710,090 B2 | 3/2004 | Koyama et al. | ............. 514/690 |

OTHER PUBLICATIONS

Janssen et al; Chem. Ber., 115(3), 1234-43, 1982.
Shozo et al, Gen. Pharmacol., 28(5), pp. 805-811, 1997.

*Primary Examiner*—Sikarl A Witherspoon
(74) *Attorney, Agent, or Firm*—Kubovcik & Kubovcik

(57) ABSTRACT

A method for inhibiting or blocking molecular generating and/or inducing functions of molecules using an inhibitory or blocking agent of the formula:

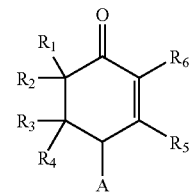

wherein R1-6 are as defined herein.

36 Claims, 26 Drawing Sheets

7,605,183 B2

```
                        SEQUENCE LISTING

<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide dimer

<400> SEQUENCE: 1
cttcggactt cgga                                                   14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide dimer

<400> SEQUENCE: 2
cttcgggctt cggg                                                   14
```

INHIBITORY OR BLOCKING AGENTS OF MOLECULAR GENERATING AND/OR INDUCING FUNCTIONS

This application is a division of application Ser. No. 11/513,174 filed Aug. 31, 2006 now abandoned, which is a continuation of application Ser. No. 10/718,854, filed Nov. 24, 2003, now abandoned, which is a division of application Ser. No. 10/029,259, filed Dec. 28, 2001, now U.S. Pat. No. 6,710,090, which is a division of application Ser. No. 08/813, 842, filed Mar. 7, 1997, now U.S. Pat. No. 6,346,551, which is a continuation of international application PCT/JP95/01783, filed Jul. 9, 1995, now abandoned, which claims priority of Japanese patent application No. 6-252660, filed Sep. 9, 1994, each of which is incorporated herein by reference.

TECHNICAL FIELD

This invention relates to compounds which have inhibitory effect or blocking effects on substrates (for example, lipids, carbohydrates, amino acids) of less than 10000 of molecular weight which has constituted structure and function of organism fundamentally and, function which is generated by macromolecules such as peptides, proteins, enzymes, nucleic acids and genes (DNA, tRNA, mRNA, rRNA) which are synthesized biologically. These applications of those inhibitory effects or blocking effects relate to antibacterial agents, antifungal agent, antiviral agent, bactericidal and/or sterilized agents (food stuff preserving agents, germination inhibitory or maturation inhibitory agents for fruits and vegetables, antibacterial agents accompanied with forming or elaborating process of plastics, antimicrobial coating materials and, waxes for interior materials and floor, preventable agents of bacterial and fungal proliferation and/or infection for house holding electric instruments, daily use goods, house furnishings and, agents for preventing of bacterial and fungal proliferation and/or infection for paper and pulp such as slime cleaning agents on industrial field of electronics, preventable agents of bacterial and fungal proliferation and/or infection for metal processing, preventable agents of bacterial and fungal proliferation and/or infection for the disposal of wastes), and those are also related to anticancer drugs, contraceptive agents for external use and/or spermatocidal agents, anticoagulants and/or antifibrinolytic agents, modulating agents of function of bioactive substances and/or inhibitors of bioactive substances such as enzymes, peptides, genes and so on, inhibitory and/or blocking agents of antigen-antibody reaction, organ and tissue preservatives, thrombolytic agents, conformation altering agents of saccharide-chains, agents for preventing arteriosclerosis, metabolism (lipids, sugar) improving agents, agents for wound healing, epithelialization promoting agents (including restoration effect of hair). Moreover, those are related to reductants of non-biological molecules (phospholipids, glyceryl group, sulfudoryl group, thiol ester group, monosaccharide and disaccharide with polysaccharide, silicone, vinyl, cellulose and so on), free radical scavengers, desulfurization agents and/or oxidation preventing agents. In addition, those are related to the following effects concerning low molecules and or macromolecules of non-biological substances, based on chemical and orbital dynamic concept concerning the inhibitory or blocking agents of molecular generating and/or inducing functions, which is proposed in this invention. Those are related to depolymerization agents, improving agents for surface active substances, phase transition agents, improving agents of phase transition, plasticity and/or elasticity promoting agents, plasticity and/or elasticity improving agents (plasticizers), fiber flexibility promoters, improving agents for fiber flexibility, glutinous agents, viscidity improving agents, adhesives, adhesive property improving agents, painting-agents, improving agents of painting, moldability improving agents, improving agents of molding forming and/or fabrication, copolymerization agents, stabilizers, antioxidants, improving agents for filling and plugging, agents for improving smoothness, ultraviolet rays absorbents, ultraviolet rays absorptivity improving agents, shock-resistant improving agents, improving agents for light stability, improving agents of mold lubricants, mold releasing agents, parting agents or surface lubricants, improving agents of molecular ring creator. Moreover, those are related to improving agents of wear resistance and/or abrasion resistance, aging resistors and/or durability, improving agents of material property and it's function, fluidability improving agents, improving agents for property of water absorption, improving agents for property of water resistance, improving agents for rigidness, hardness and softness, improving agents of crystallized materials and/or amorphous materials, flexibility promoters, and improving agents for changing flexibility. And, those are related to improving agents of physical property of macromolecules composite materials, function improving agents of macromolecules composite materials, improving agents of physical property of functional macromolecules composite materials, function improving agents of functional macromolecules composite materials, modulation agents and/or improving agents of excitation wavelength and fluorescent wavelength on pigmentums, coating materials, cosmetic pigments, colorants, photolysis agents and improving agents of photolysis.

BACKGROUND ART

Formerly, it has been well known that the basic principle of organic structural chemistry such as bond angle, molecular weight, acidity, bond length, structure, hydrogen bond, resonance, basicity, optical activity, configuration, and conformation is important as well as mechanism of chemical reactions (by Morrison and Boyd, organic chemistry, 6th edition, Tokyo Kagaku Doujinn publication at reference <ref. 1>). On the other hand, for example, elements of living organism consist of lipids, carbohydrates, proteins, enzymes, nucleic acids, macromolecules amino acids and peptides and genes (for example, DNA, tRNA, mRNA, rRNA) and by those elements, in addition, formation of cell membrane, intracellular organella, intracellular and/or extracellular substrates are constructed. Function of these complex substances is generated by multi-dimensional structure (conformation) depending on each substance. In order to understand the mechanism which is related to development and generation of each physiological function (recognition and/or acceptance of substance), it is important to understand the multi-dimensional structure which each substance has. (Alberts, Bray, Lewis, Raff, Roberts and Watson works, The Molecular Biology of the CELL, Garland Publishing Inc., 3th. edition <ref. 2>). It is also known that methyl group contributes in order to produce fluidability and hydrophobicity of substances in the non-living organism, which contains lipids, proteins and so on. <ref. 1>. The cell membrane of organism, which is the base units separating from external environment, also consists of hydrophobic component of lipids outside a membrane. And, this cell membrane has important role in signal acceptance into a cell from another cell. To connect and adhere between each cell and to surround intercellular organella also constructed with extremely thin film-like membrane which consist of lipids and proteins molecules. The proteins which is embedded in the membrane has highly biological activities as intermediates around the cell, and between an inside of organella and cytoplasm. According to types of cells, it is an existence of various enzymes which involves in intracellular signal transduction and in intercellular respiration. In addition, it is also known that there is a substance such as tubulin which is relation on morphologic keep of cell, mitosis and prolifelation. Moreover, proteins in a plasma membrane contribute to recognize signals between cells. Hydroxyl group, sulfudoryl group (—SH) and disulfide bond are constituted ester. According to these cross-linking reaction, also, physiological functions which are generated by multi-dimensional structure of a substance are altered. In addition, amino nitrogen generates property of basicity as well as nucleophilic property on molecular reaction. When peptides and proteins are denaturated, coiling of each peptide and proteins is relaxed. Thus, the particular multi-dimensional structure of the peptide and proteins is crumbled, followed by losing a particular bioactivity of the peptides and proteins. Moreover, such change in conformation appears not only in peptide and proteins but in complex substance with phospholipids and glycoproteins (for example, nucleic acids). In addition, in order to maintain a specificity of each physiological function which is generated by moiety of membrane, a substance which is secreted into the outside of cells, enzymes which exists into the cell, cytoskeleton and a substrate which is synthesized within cell, it is also known that it is important that each substance forming living organism has two-dimensional and three-dimensional configuration such as helical structure and sheet. A state of charge distribution and electric charge density of molecules which consist of substances and is generated function by these multi-dimensional structure differs in species differences and morbidity <ref. 2>. In addition, virus, which has not cell membrane and is not living organism, consists of peptides chain which are constructed by many amino acid bindings. And, these virus particles have also multi-dimensional structure such as two-dimension and/or three-dimension. Among multi-dimensional structure, helical structure is formed in 3.6 amino acid residues per one helical rotation. Thus, it produces a space which side chain can occupy. And, possible hydrogen bonds on this helical structure can be constituted all. In addition, multi-dimensional structure generates the function of α domain, beta domain, α/beta domain, exon or intron. This concept is also a scientific fact and important knowledge. Though a core part of this structure is conserved in homologous proteins, dimensional changes in a helix loop region occur. Moreover, formation of conformation depends on a type of the secondary structure to bind each loop and a number of amino acids in helix loop rather than amino acid sequences. Therefore, it is in general to be determined by combination of α-α, beta-beta, α-beta or beta sheet-α loop. And, multi-dimensional structure of helix loop induces a change of cytoskeleton, mitosis and prolifelation according to change in conformation of each substance (for example, tubulin and spectrin) resulting from changes in an intracellular energy. Moreover, recent scientific topics is to know mechanism of oncogeneis, mechanism of anticancer agents, mechanism of anti-proliferation, natural cell death (for example apoptosis), mechanism of aging process of the nerve cell, cell recognition or mechanism of cell adhesion. While such scientific knowledge is turned into basement, it is hoped for development of new drugs which is utilized to organism such as human being. Though pharmacological effects of conventional antibacterial agents and anticancer drugs have been introduced at cell death, primary mechanism of cell death due to those conventional antibacterial agents and anticancer drugs is to raise denaturation, coagulation and/or necrosis. For this reason, an appearance of mutants and resistant strains as major scientific problems has been left numerously to be resolved. From such a reason, additionally, scientific interest in mechanism of apoptosis arises at present. Moreover, living organism can move automatically by a flagellum and pilli, and a supermicro-size of motor has been provided for pilli of spermatozoa. On driving motor of this organism, energy which is generated by hydrolysis of ATP is utilized. A change in this energy produces to alter multi-dimensional structure of the helix loop which is configurated by myosin. These multi-dimensional structure is to apply to molecular biology of every kinds of genes and antibodies from recent knowledge. It is well known scientific fact and knowledge that it is important to generate physiological function based on recognizing two- or three-dimensional conformation of each substance <ref. 2>. But, it has been known that the substance which consists of living organism does not usually exist in an initial position and, it exists in dynamic state (for example, movement of membrane proteins is slower than that of lipids molecules which is about 100 times later). In addition, if movement of lipids molecule results in more animation, fluidability of a membrane indeed becomes larger. But, the speed of the movement differs dependently on types of lipids. A self-action adjustment capability of membrane fluidability holds in organism. On the other hand, it is also known that a hindrance of those adjustment capability causes onset of diseases in human being. For this reason, it is hoped standby that the countermeasure is proposed against a hindrance of the adjustment capability. In addition, interaction of hydrophobicity between hydrophobic groups is greatly committing in stability of lipids bilayer of the biomembrane which is known as a fluidability model. Moreover, since side chain of many amino acids with hydrophobic property flanking in an inside of proteins, it does not come in contact with to water. For this reason, it is also well known that multi-dimensional structure of proteins is kept by hydrogen bond, hydrophobic interaction and van der Waals force and, it makes a flexible matrix. Greater hydrophobic solute is more easily to bind to proteins. In order to get in a hydrophobic region close at proteins surface which hydrophobic molecule exists, it is thought that conformation of proteins changes. In this way, when life events is understood, it is to be important to understand life activity dynamically and multidimensionally. According to a base of the scientific logic mentioned above, the scientific interest in controlling quality of physiological activity is needless to say and, proposal of a new manner for prevention and treatment of various kinds of diseases is eagerness historically.

Though it is not necessary to do more than to read history of relationship between a man and diseases, a fighting to pathogenic microbacterial infection such as bacteria and virus, it is serious problems which needs a medical resolution. And, even though development of advanced medical technology, it is a serious problem that multiple organ failure accompanied with sepsis and disseminated intravascular coagulation causes to result in the death of human being (Hypotension—for clinician to understanding pathophysiology—Fujita Publ. by Koyama) <ref. 3>. Various kinds of pathogenic microbacteria such as *staphylococcus aureus, streptococcus, E. Coli*, acid-fast bacteria, mycete and virus usually exist on the living space of human being as origin of various infectious diseases. Up to this time, sanitatory administration to the living space of human being can have been turned into prevention of this pathogenic microbacterial and viral infection. Thus, lots of drugs are utilized in a treatment and prevention for infectious disease in living space of human being, by using disinfectant and/or bactericidal agents. As a result, lots of the fruits have been raised. However, while development of antibacterial agents is noticeable, application of drugs concurs at an appearance of a resistant strain and, a social administrative problem as well as difficulties of medical care has been raised. For example, it is an appearance of various kinds of multi-drug resistant strains which represent methitilin resistance *staphylococcus aureus* (<MRSA> with abbreviation). In order to show resistance to lots of betalactam group drugs in *staphylococcus aureus*, a treatment for infectious disease due to MRSA is difficult and, it becomes pathogenic organism such as opportunistic infection and postoperative infection in clinical practices and, an infected patient to this MRSA changes a serious illness and, he is easy to fall into sepsis and multiple organ failure. Thus, onset of untreatable infection due to MRSA is a serious social issue. An infection of *pseudomonas aeruginosa* is anxious for preventing secondary infection from burn injury as a complication. From a point of related view with cystic pulmonary fibrosis, recently, an approach to preventing this infection of *pseudomonas aeruginosa* is a great problem. Moreover, many interests are recently brought nearer to *helicobacter pylori* as a cause of peptic ulcer or abhorrent factor. In addition, infection of acid-fast bacteria and mycete is international problems as for an infectious complication whose acquired immune deficient syndrome (AIDS) is fatal. Therefore, it is an important international request that it is developed valid drugs on an infectious disease by virus, drugs which have potencies of antimicrobacterial effect to MRSA and/or acid-fast bacteria, drugs for *E. Coli* which is easy to cause sepsis, drugs which have potencies of antifungal effect.

And also, recently, opportunistic infection in daily living space (for example, air-conditioning contamination according to regionerae) and on surrounding in life behavior as well as in a hospital become serious problems and, bactericidal and/or sterilized agents is recognized again as a prevention countermeasure of bacteria contamination including opportunistic infection. An appearance of society which is populated by many aged generation has been appealed in the near future and, urgent technological development is expected a counterattack of medical care for the aged.

Generally, *staphylococcus aureus*, acid-fast bacteria, mycete and virus are easy to encounter an opportunity of an infection through respiratory system such as nasal cavity and pharynx, and through digestive tract. Conventional bactericidal and/or sterilized agents frequently depends on a physical manner by living space of human being and at surroundings in life behavior and, moreover, major administration route of drugs such as antibiotic is sometimes restricted in the way of oral administration, intravenous administration and/or direct administration to the infection focus and, there is some apprehensions and inconveniences to medical care specialists, a nursing volunteers and home helpers as well as patients them self. But, during a period which people is alive, we have to continue to come in contact with an external air through skin and respiratory system. Thus, it is expected to utilize room air which is living space for preventing or treating infectious diseases. Generally, in order that bacteria can obtain their resistant abilities by various genetic mechanism such as mutation, selection, character introduction, autotransduction of plasmid, bacterial infection can not be prevented completely by using of conventional simple substance which is chemically synthesized and, the chemotherapeutic agents without induction of being a resistant strain also have not supplied until the present. And, as an aim for an inhibition of a primary structure of the substances which consist of bacterial membrane, a few of drugs with antimicrobacterial effect has been applied abundantly. All the more, while developments of an administration manner of antibacterial agents are also important and are anticipated, additional development of new antibacterial, antifungal agents and/or and antiviral agents which affect on multi-dimensional structure is expected strongly. Moreover, for a marked increase in population on the earth, namely developing countries, it is important to propose a possible planning of birth control even in regarding with supplying foods and trusting of natural resource in the future. However, though a use of physical contraception such as condom and pessary is as a matter of course as for planning of birth control, ovulation control by use of a female sex hormone and operative contraception to both male and female is driven proposal internationally. In order to avoid to be damaged the heredity information of spermatozoa to suppress it's fertility, a new method of the contraception which can inhibit a movement ability of spermatozoa is also expected. On the other hand, in order to generate the function of living organism, multi-dimensional structure of substances as above-mentioned plays an important role. However, though it is expected that a substance with simple chemical structure can inhibit and/or block the function generated or induced by the multi-dimensional structure of biological substances, there is not proposal of such representative substance, which is little harm and safety, concerning life continuation as integrated whole body at the present. Not only proposal of such representative substances and several proofed efficiencies above mentioned is interest in academic events such as biology, chemistry and medicine, but it is sought that such a suggestion is hastily proposal in practical medical care.

Numerous daily materials, industrial and environmental materials are provided to develop at the present society by understanding, analyzing, manufacturing and improving physical property of low molecule substances and macromolecules substances and by utilizing their functional properties. But, by qualitatively advancing improvement of physical property of low molecule substances and macromolecules substances, an expectation is to propose a representative which makes function, efficiency, comfortableness and safety. For example, physical property of a macromolecules substance such as surface activity substance and polymerization substance is described briefly.

A magnitude of surface activity relates on criticality density for micell formation and solubilization. And, Krafft point is lower as a chain-like (rod-like) part with the substance is short. It is known that a value of criticality density of micell formation is greater as a chain-like (rod-like) part with the substance is short. According to each characteristic configuration of molecule in surface-active agents and/or surfactants, it can effectively produces bubbling formation, wetting, a fall of surface tension, emulsification (formation of emulsion), solubilization, formation of micelle detergency. In addition, in a case of substance with properties of water insoluble and strong hydrophilic, a less intermolecular force between it's molecule and broad wide spreading on the water surface, it is also known that a membrane with one molecular layer (single molecular film) is formed. If this single molecular film can be transferred on the surface of solid, a surface of hydrophobicity is obtained. For this reason, proposal of improving agents for surface active substances is that it is prospected in making thin film such as LB membrane. In addition, surface-active agents and/or surfactants has a potency of disinfection, stability in hard water. By utilizing these effect, surface-active agents and/or surfactants are blended cosmetics, cleansing creams, shampoos and rinses and, they are widely utilized in electrically charging preventive agents (antistatic agents) of plastics and fibers, softening agents of fibers, foaming, frothing, lathering or whipping agents of aerosol and tinction assistants. Thus, proposal of improving agents for surface active substances is prospected in many fields. Moreover, polyethylene is representative in various kinds of polymers. Polyethylene is a thermoplastic crystal which is repeated of —$CH_2CH_2$— and, it produces branches dependently on a manufacturing method resulting in decrease in crystallinity and rigidity as well as increase in transparence. In addition, polyethylene is added short chained branch (for example, ethyl branch and butyl branch) by pull out reaction (abstraction reaction) of hydrogen within molecule due to back-biting during polymerization resulting in low density and, branch (long chained branch) which is identical to main chain of the polymer is produced by pull out reaction (abstraction reaction) of hydrogen between molecules. Linear polyethylene (LLD polyethylene) has an intensity for impact force. In addition, medium density polyethylene (MD polyethylene) and ultra-low density polyethylene (VLD polyethylene) are used as improving or reforming agents of resins. Ultrahigh molecule weight polyethylene (UHMW polyethylene) is applied widely by the reason that it is superior to self-lubricating, shock resistance and wear resistance and/or abrasion resistance. In this way, it is expected to propose improving agents which can approve property of each substance in order to make arise a quality of macromolecules substances. Moreover, each polymer in macromolecules substances has a characteristic property itself. For example, ethylene/vinyl acetate copolymer is superior in springiness, elasticity, transparence, stout and heat seal. Polymer in methacrylic acid ester group among methacrylate resins and resins in acrylonitrile group is named generically with metacrylate resin and, they have widely utilized in materials for illumination, commercial advertising panel, car and train, electrical and/or optic materials, daily goods and so on by use of their superior properties such as surface luster, transparence and weather resistance. In addition, other physical properties of polymers is filmed-formation property, rubber-like property, mechanical stout, anti-creep, flexibility, thermoplasticity, thermal resistance, dimensional stability, phase transition, shock resistance, fluidability, surface luster, water resisting property and chemical resistance. Moreover, there are processability, printing, painting, deposition, secondary processing such as lamination, epibole, waterproof, separating, bubble-breaking, oxidation prevention, increasing viscosity, pyrogenetically consolidating property, gelatinization at ordinary temperature, thermal displacement, thermal resistance, alkali resistance, flexural strength, bending elasticity, tug strength, electric characteristics, adhesion, erosion- or rust-resistance, sliding property with thermal resistance, radiation resistance, poly-valenced metal ion capture ability (chelate ability), dispersibility, aggregation ability as another physical properties. Concerning our present social civilization life, these macromolecules substances are necessary and indispensable in our daily life. Thus, it is expected to provide more effective materials which are improved each physical property by combining with each physical property. Polyethylene glycol is one example of the macromolecules which is daily used in general. Application of polyethylene glycol is widely expanded into the manufacturing fields such as cream lotion in cosmetic industry, lubricant in metal processing and/or fiber industry, binder of tablet for pills in pharmaceutic industry and basic material for producing surface-active agents and/or surfactants and, moreover, it is also utilized flocculant for inorganic substances such as clay, resin reform agents (prohydration), thickeners, binders for ceramic, pulp dispersing agents and flocculants for pulp. Then, it is expected to be improved physical property of polyethylene glycol as more safety and effective materials.

Moreover, highly polymerized sodium polyethylene acrylic acid is permitted legally as food additive and/or cosmetics material. Thus, it is expected that a proposal of new technique and/or new substance can improve a physical property resulting from change in multi-dimensional structure (conformation) of this polyethylene acryl amide polymer.

In generating property of various types of fibers such as natural fibers in cellulose group, synthetic fibers in hydrocarbon group, synthetic fibers in polyvinyl alcohol group, acrylic synthetic fibers, polyamide synthetic fibers, aramide fibers, synthetic fibers in polyester group, fibers in polyurethane group and carbon fibers, each characteristic feature of those fibers is produced by their molecule configuration and their multi-dimensional structure. Moreover, each physical property of natural gum and synthetic rubber latex, which can produce rubber-like elasticity dependently on given temperature, is also changed by alteration of multi-dimensional structure. Collagen also takes three pairs of right winding spiral structure resulting from formation of left winding helix. Thus, the role of function of this collagen also differs by it's multi-dimensional structure. Generation of function corresponding to the aim and it's utilization is also expected by improving the multi-dimensional structure of collagen fibers.

Moreover, there are cosmetic pigments, agents in water-soluble coating materials, scale preventing agents, electroconductive treating agents, stabilizers for emulsion and polymerization, coating materials utilized paint film formation, coating materials of powder, coating materials for radiation consolidation, soluble non-dispersing coating materials and others as another uses of macromolecules. Those are also applied to housing materials, electricity products, motor vehicles, construction materials, furnitures and electric wire insulation mantles and so on. From such reasons, proposal of a new technique and/or a new substance to improve the physical property of these coating materials is prospected.

So, in order to extend utilization of macromolecules, appropriate adhesives is also necessary. To improve function of these adhesives and to efficiently utilize macromolecules substances is expected in various fields such as medical care system, transport system, communication system and constructions.

Moreover, composite materials of macromolecules with specific function is used. The specific function is optical transfer, polarity, recording medium for electronic machines, separating membrane, electrical conductivity, electrical conductivity with transparence, electricity conductivity related to optical radiation, vibration-damping, sound arresting, heat conductivity and so on. Additionally, composite materials of macromolecules with specific function has a possible potential to apply into tip materials such as module for separation, metallizing resins, impact-relaxation materials, vibration-damping conductive materials, optic fibers, magnetic recording medium, optical recording medium, rewritable optical disc. For this reason, a new technique and possible idea which can easily control the function of composite materials as well as change in configuration of the materials are expected in order to make function and performance better.

In addition, functional polymers which can cause a chemical change or a physical change by physical and chemical stimuli externally and which can produce a state change by interaction with a corresponding substance are generated by effects of reactable substrate with specific function which is introduced into main chains and/or side chains of macromolecules or it's precursor and by a proportional property and specific conformation of an additive. For example, there are materials for electricity, semiconductor related materials, photosensitive polymeric materials, recording materials, materials for liquid crystal display, tip materials, liquid crystal materials of macromolecules, optoelectronics materials, materials for thin films, photochromic materials, optical recording materials, optical tip materials, holographic recording materials, nonlinear optical tip materials, optical responding materials, sensor related materials and transducer related materials as functional polymer composites. Therefore, in order to make well generation, good efficiency and accurate stabilization of each functional property, it is expected to improve function of these polymers. In addition, an improvement of printed circuit board materials for the optical disc which needs property such as transparence, mechanical intensity and thermal resistance and of thin film materials such as the amorphic membrane which polymerized membrane is cross-linked tridimensionality is also expected. Moreover, as an applied example of macromolecules, there is also polymer with photochemistry reaction which causes a configuration change such as cross-linking, polymerization, polarity change, decomposition and depolymerization due to light. Thus, as well as improvement of chemical structure of these photosensitive functional polymers, it is also expected that proposal of a new technique and possible idea which can improve a physical property of materials by changing those conformation.

Moreover, there are also macromolecular substances which have been utilized for detergents, cosmetics and foodstuff. A substance with more useful physical property which results from improving conformation accompanied with generating functional property has been expected to make quality of life and environment better. Additionally, property of macromolecules is utilized as supporting materials in medical health care, then, it is also expected to propose useful and new biomaterials which have better fitness and adaptation to body by improving property of conventional biomaterials which is utilized macromolecules. In addition, there are also stabilizers which makes stability against heat and light, antioxidants (age resistors) which prevents progress of oxidation and ozonolysis, promoting agents which makes plasticity, elasticity and processability well and softener. Moreover, there are also flame retarders with fire-resistance, cross-linking agents, fillers, treating agents for fibers, oily agents, electrically charging preventive agents (antistatic agents), final forming agents for flexibility, final forming agents for polymers, additives for plastics, ultraviolet rays absorbents, optical stabilizers, lubricants, curing agents and/or vulcanizing agents, age resistors and softeners. In addition, there are also sclerosing agents and tackifiers, reinforcers, fillers, additives for adhesives, additives for coating materials, cosmetic pigments, solvents, consolidation accelerators, deterioration preventives, dispersing agents as a tool as additives of polymeric materials. Then, it is known well that those are used corresponding to each objective. By improving property of such additives which are used for these polymeric materials, it is expected to provide a new material which has useful functional property.

Moreover, there are various kind of macromolecules for using as detergents, cosmetics and foodstuff. Macromolecules in foodstuff as an example are representative substances such as polysaccharides, foodstuff proteins and macromolecules for gum. Macromolecules for gum, for example, have natural resins such as chicle, soruba and jelutong which contains polyethylene isoprene and which is utilized chewing gum as natural additives. In addition, there are vinyl acetate resin, polyisobutylene, polyethylene butene, isobutylene-isoprene rubber, styrene-butadiene rubber (SBR), polyethylene, terpene resin and so on as food additives. Macromolecules extracted from plants and/or animals as well as synthesized macromolecules are used in detergents and cosmetics. Thus, it is important that in the point of view at better quality of life itself as well as life space, physical property of macromolecular substances is improved it's conformation generating specific characteristic and function, resulting in being useful one. In addition, an example of utilizing a property of macromolecules as medical care aids materials is a dialysis membrane. As a material of a dialysis membrane, though natural macromolecules (celluloses, cellulose acetate fibers) and synthesized macromolecules (for example, polymethylmethacrylate, polyacrylonitrile, polysulfone, ethylene/vinyl alcohol copolymer) is general purposed, it is also expected to develop a useful and well adapting biomaterials by improving property of these conventional biomaterials. Moreover, prospected additives are antioxidants (or age resistors) which prevent an progress of oxidation and ozonolysis and stabilizers which make stability constant against heat and light. It is also expected to make each performance better by processing a new additive to promoting agents which makes plasticity and/or elasticity, softeners, flame retarders which is added flame-resisting, cross-linking agents (or curing agents and/or vulcanizing agents), fillers, treating agents for fibers, oily agents (for example, spinning oil), antistatic agent (for example, compounds with polyethylene glycol chain, surface-active agents and/or surfactants), final forming agents for flexibility, final forming agents for polymers or additives for plastics. Ultraviolet rays absorbents, optical stabilizers, lubricants, curing agents and/or vulcanizing agents, and age resistors are also important as additives. Softener has an effect as a lubricant in the intermolecular space of gum and has a potency of controlling dispersibility of other additives and, they play a role of increasing in volume of combination agents. In order to produce better physical property such as hardness, tug strength, modulus, anti-elasticity, friction resistance, wear resistance, tear resistance into carbon black and rubber goods, tackifiers and/or reinforcers frequently are added. In addition, fillers, additives for adhesives, additives for coating materials, cosmetic pigments, solvents, sclerosing agents, consolidation accelerators, deterioration preventives, dispersing agents and so on are used as additives of macromolecular materials according to each objective. It is expected to improve property of those additives for various kinds of macromolecular materials as above mentioned.

In conformity with a biological fact mentioned above, it is expected to provide a representative agent and/or drug with the following effects, that can inhibit or block the function generated by multi-dimensional structure of substances which consists of living organism; extracellular matrix, cell membrane, cytoskeleton, cytoplasm and components of intracellular organella such as enzymes, genes, antibody, proteins, sugars, lipids. Those agents and/or drugs are antibacterial agents, antifungal agent, antiviral agent, bactericidal and/or sterilized agents, anticancer drugs, anticoagulants and/or antifibrinolytic agents, blood coagulation and fibrinolysis blocking agents, inhibitory and/or blocking agents of antigen-antibody reaction, organ and/or tissue preservatives, food preservatives. In addition, those agents and/or drugs are also germination or maturation inhibitory agents of fruits and vegetables, antibacterial agents for plastic processing, antimicrobial coating materials, antimicrobial resin waxes, house holding electric instruments, agents for preventing of bacterial and fungal proliferation and/or infection of house furnishings and daily use goods, slime preventing agents for pulp and paper, cleaning agents on field of electronics, agents for preventing bacterial and fungal proliferation and/or infection on metal processing oil (metal working fluid), the agents for preventing bacterial and fungal proliferation and/or infection on the disposal of waste. Moreover, it was hoped for development of inhibitory agents and/or blocking agents of function due to bioactive substances such as enzymes, peptides and genes, spermatocidal agents or contraceptive agents for external use, thrombolytic agents, conformation altering agents of saccharide-chains, agents for preventing arteriosclerosis, metabolism (lipids, sugar, proteins) improving agents, agents for wound healing, epithelialization promoting agents, and inhibitors and/or blocking agents which are able to inhibit or block function generated by the multi-dimensional structure of substance which living organism has many kinds of substrates.

An objective of this invention is to resolve the problems mentioned above, and is to provide inhibitory or blocking agents of molecular generating and/or inducing functions, that can inhibit or block functions generated by the multi-dimensional structures of reactive substrates and have a simple chemical structure.

DISCLOSURE OF THE INVENTION

In order to complete the above-mentioned objective, the inventors carried out research and determined that the chemical compounds which are shown in the following general formulae (1-a), (1-b), (2), (3-a) and (3-b) or acid addition salt compounds thereof which are active provide the objective mentioned above.

The invention is the inhibitory or blocking agents of molecular generating and/or inducing functions which has the original molecular structure shown in general formula (1-a) (1-b). And, the compounds, the derivatives or those acid addition salt compounds provide antibacterial agents, antifungal agent, antiviral agent, bactericidal and/or sterilized agents, anticancer drugs, blood coagulation and fibrinolysis inhibitors and/or blocking agents, inhibitory and/or blocking agents of antigen-antibody reaction, organ and/or tissue preservatives, antiseptics and preservatives for foodstuffs, germination and maturation inhibitory agents for fruits and vegetables. In addition, the compounds, the derivatives or those acid addition salt compounds provide antibacterial agents for plastic processing, antimicrobial coating materials, antimicrobial resin waxes, agents for preventing of bacterial and fungal proliferation and/or infection of house holding electric instruments, daily use goods and house furnishings, slime preventing agents for papers and pulps, cleaning agents in field of electronics, agents for preventing bacterial and fungal proliferation and/or infection for metal processing oil (metal working fluid), agents for preventing bacterial and fungal proliferation and/or infection for the disposal of waste. In addition, the compounds, the derivatives or those acid addition salt compounds provide spermatocidal agents and/or contraceptive agents which aim to suppress fertility of spermatozoa, thrombolytic agents, conformation altering agents of saccharide-chains, agents for preventing arteriosclerosis, metabolism (lipids, sugar) improving agents, agents for wound healing, epithelialization promoting agents (including hair restoration effect), inhibitors and/or blocking agents which can control generation of function with bioactive substances (for example, enzymes, peptides, gene). In addition, the compounds, the derivatives or those acid addition salt compounds can inhibit and/or block function generated by multi-dimensional structure (conformation) of the substance which consist of a shape and function of living organism. Moreover, the compounds, the derivatives or those acid addition salt compounds provide chemical substances which can control, inhibit and/or block the function which is generated by multi-dimensional structure (conformation) with macromolecules substances and macromolecules composite materials as well as living organism. In addition, when halogen compounds such as halogenated alkali metals or halogenated alkali-earthy metals or halogenated zinc is added in the compounds which were provided by this invention, a reaction is able to be induced. Moreover, when gold colloid is added in the compounds which were provided by this invention, marking and/or labeling substances can be made and, it is also possible to use the compounds which were provided by this invention as dispersion (diffusion) preventives of tinction and printing dye, ink stabilizers or dye sticking agents. In addition, by using a color coupler such as dye with the compounds which were provided by this invention, coloring of the dye can be enhanced. When fragrant agents is used with the compounds which were provided by this invention, possible fragrance can be produced. In addition, the compounds, the derivatives or those acid addition salt compounds can be utilized as depolymerization agents, surface-active agents and/or surfactants, improving agents for surface active substances, phase transition agents, improving agents of phase transition, improving agents of microphase separation structure, plasticity and/or elasticity promoting agents, plasticity and/or elasticity improving agents (plasticizers), copolymerization agents, copolymerization improving agents, improving agents of fluorescent wavelength of colorants, polymerization regulators, improving agents of polymerization adjustment, stabilizers, stabilization improving agents, antioxidants, oxidation preventing agents, agents for improving crystallized materials and/or amorphous materials, fluidability improving agents, flexibility promoters, improving agents for changing flexibility, alterable agents of excitation wavelength, fluorescent wavelength and excitation wavelength of pigmentums, coating materials and cosmetic pigments. And, it is also possible to utilize the compounds, the derivatives or those acid addition salt compounds as the following improving agents. Those are agents which can improve physical property of low molecule substances, agents which can improve function of low molecule substances, agents which can improve physical property of macromolecules substance, agents which can improve function of macromolecules substances, and agents which can improve physical property of macromolecules composite materials and functional macromolecules composite materials.

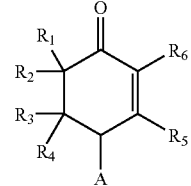

General Formula 1-a

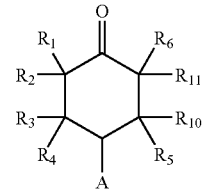

General Formula 1-b

However, in the formula,
(i) $R_1$, $R_2$, $R_3$, $R_4$, $R_5$, $R_6$, $R_{10}$ and $R_{11}$ represents independently hydrogen atom; halogen atom; C1-C6 alkyl group; amidino group; C3-C8 cycloalkyl group; C1-C6 alkoxy C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group;

(ii) A represents hydrogen atom or

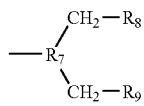

(wherein
R7 represents C1-C6 alkyl group; sulfide group or phosphate group;
R8 and R9 represent independently hydrogen atom; halogen atom; straight or branched C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group;
(iii) one or more of R1, R2, R3 and R4, and/or one or more of R5, R6, R10 and R11 may be substituted or non-substituted cyclopentyl group; substituted or non-substituted cyclohexyl group; or substituted or non-substituted naphthyl group;
(iv) R5, R6, R10 and R11 may form a ring by binding with another condensation polycyclic hydrocarbon compound or heterocyclic compound;
(v) one or more of R3, R4, R5, R6, R10 and R11 may be substituted by one or more of substituents selected from the group consisting of halogen atom, cyano group, protected or non-protected carboxyl group, protected or non-protected hydroxyl group, protected or non-protected amino group, C1-C6 alkyl group, C1-C6 alkoxy group, C1-C7 alkoxy carbonyl group, aryl group, C3-C6 cycloalkyl group, C1-C6 acylamino group, C1-C6 acyloxy group, C2-C6 alkenyl group, C1-C6 trihalogenoalkyl group, C1-C6 alkylamino group, and C1-C6 dialkylamino group;
(vi) R2 and/or R5 may be substituted by one or more substituents selected from the group consisting of halogen atom, C1-C6 alkyl group, protected or non-protected carboxyl group, protected or non-protected hydroxyl group, protected or non-protected amino group, protected or non-protected C1-C6 alkylamino group, protected or non-protected C1-C6 aminoalkyl group, protected or non-protected C1-C6 alkylamino C1-C6 alkyl group, protected or non-protected hydroxyalkyl group, and C3-C6 cycloalkylamino group;
(vii) when one or more of R3, R4, R5, R6, R10 and R11 are alkyl groups, terminal end(s) of the alkyl group(s) may be substituted by C3-C8 cycloalkyl group).

The aryl group in (i), (ii) and (v) may be phenyl, tollyl, xylyl or naphthyl group. The substituted cyclopentyl group in (iii) may be cyclopentylamino group or cyclopentylcarbinol group, the substituted cyclohexyl group in (iii) may be cyclohexylamino group, cyclohexylaldehyde group or cyclohexyl acetic acid group, and the substituted naphthyl group in (iii) may be naphthylamino group or naphthylamino sulfonic acid group. The condensation polycyclic hydrocarbon compound in (iv) may be pentalene, indene, naphthalene, azulene, heptalene, biphenylene, indacene, acenaphthylene, fluorene, phenalene, phenanthrene, anthracene, pentacene, hexacene, dibenzophenanthrene, 1H-cyclopentacyclooctene or benzocyclooctene, and the heterocyclic compound may be furan, thiophene, pyrrole, γ-pyran, γ-thiopyran, pyridine, thiazole, imidazole pyrimidine, indole or quinoline.

The invention is the inhibitory or blocking agents of molecular generating and/or inducing function which has the original molecular structure shown in general formula (2). And, the compounds, the derivatives or those acid addition salt compounds with effective integents provide antibacterial agents, antifungal agent, antiviral agent, bactericidal and/or sterilized agents, anticancer drugs, blood coagulation and fibrinolysis inhibitors and/or blocking agents, inhibitory and/or blocking agents of antigen-antibody reaction, organ and/or tissue preservatives, antiseptics and preservatives for foodstuffs, germination and/or maturation inhibitory agents for fruits and vegetables, antibacterial agents for plastic processing, antimicrobial coating materials, antimicrobial resin waxes, agents for preventing of bacterial and fungal proliferation and/or infection of house holding electric instruments, daily use goods and house furnishings, slime preventing agents for papers and pulps, cleaning agents in field of electronics, agents for preventing bacterial and fungal proliferation and/or infection for metal processing oil (metal working fluid), agents for preventing bacterial and fungal proliferation and/or infection for the disposal of waste, spermatocidal agents and/or contraceptive agents which aim to suppress fertility of spermatozoa, thrombolytic agents, conformation altering agents of saccharide-chains, agents for preventing arteriosclerosis, metabolism (lipids, sugar) improving agents, agents for wound healing, epithelization promoting agents (including hair restoration effect), inhibitors and/or blocking agents which can control generation of function with bioactive substances (for example, enzymes, peptides, genes). In addition, the compounds, the derivatives or those acid addition salt compounds with effective integents can inhibit and/or block function generated by multi-dimensional structure (conformation) of the substance which consist of a shape and function of living organism. Moreover, the compounds, the derivatives or those acid addition salt compounds with effective integents provide chemical substances which can control, inhibit and/or block the function which is generated by multi-dimensional structure (conformation) with macromolecules substances and macromolecules composite materials as well as living organism. In addition, when halogen compounds such as halogenated alkali metals or halogenated alkali-earthy metals or halogenated zinc is added in the compounds which were provided by this invention, a reaction is able to be induced. Moreover, when gold colloid is added in the compounds which were provided by this invention, marking and/or labeling substances can be made and, it is also possible to use the compounds which were provided by this invention as dispersion (diffusion) preventives of tinction and printing dye, ink stabilizers or dye sticking agents. In addition, by using together a color coupler such as dye with the compounds which were provided in this invention, coloring of the dye can be enhanced. When fragrant agents is used with the compounds which were provided by this invention, possible fragrance can be produced. In addition, the compounds, the derivatives or those acid addition salt compounds can be utilized as depolymerization agents, surface-active agents and/or surfactants, improving agents for surface active substances, phase transition agents, improving agents of phase transition, improving agents of microphase separation structure, plasticity and/or elasticity promoting agents, plasticity and/or elasticity improving agents (plasticizers), copolymerization agents, copolymerization improving agents, polymerization regulators, improving agents of polymerization adjustment, stabilizers, stabilization improving agents, antioxidants, oxidation preventing agents, improving agents of crystallized materials and/or amorphous materials, fluidability improving agents, flexibility promoters, improving agents for changing flexibility, improving agents of fluorescent wavelength and excitation wavelength of pigmentums, coating materials, cosmetic pigments and colorants, modulating agents of excitation wavelength and fluorescent wavelength of pigmentums, coating materials, cosmetic pigments and colorants. And, it is also possible to utilize the compounds, the derivatives or those acid addition salt compounds as the following improving agents. Those are agents which can improve physical property of low molecule substances, agents which can improve function of low molecule substances, agents which can improve physical property of macromolecules substance, agents which can improve function of macromolecules substances, agents which can improve physical property of macromolecules composite materials and functional macromolecules composite materials.

General Formula 2

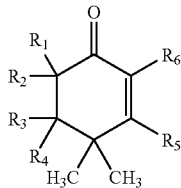

wherein
(i) R1, R2, R3, R4, R5 and R6 represent independently hydrogen atom; halogen atom; C1-C6 alkyl group; amidino group; C3-C8 cycloalkyl group; C1-C6 alkoxy C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group;
(ii) one or more of R1, R2, R3 and R4, and/or one or more of R5 and R6 may be substituted or non-substituted cyclopentyl group; substituted or non-substituted cyclohexyl group; or substituted or non-substituted naphthyl group;
(iii) R5 and R6 may form a ring by binding with another condensation polycyclic hydrocarbon compound or heterocyclic compound;
(iv) one or more of R3, R4, R5 and R6 may be substituted by one or more of substituents selected from the group consisting of halogen atom, cyano group, protected or non-protected carboxyl group, protected or non-protected hydroxyl group, protected or non-protected amino group, C1-C6 alkyl group, C1-C6 alkoxy group, C1-C7 alkoxy carbonyl group, aryl group, C3-C6 cycloalkyl group, C1-C6 acylamino group, C1-C6 acyloxy group, C2-C6 alkenyl group, C1-C6 trihalogenoalkyl group, C1-C6 alkylamino group, and C1-C6 dialkylamino group;
(v) R2 and/or R5 may be substituted by one or more substituents selected from the group consisting of halogen atom, C1-C6 alkyl group, protected or non-protected carboxyl group, protected or non-protected hydroxyl group, protected or non-protected amino group, protected or non-protected C1-C6 alkylamino group, protected or non-protected C1-C6 aminoalkyl group, protected or non-protected C1-C6 alkylamino C1-C6 alkyl group, protected or non-protected hydroxyalkyl group, and C3-C6 cycloalkylamino group;
(vi) when one or more of R3, R4, R5 and R6 are alkyl groups, terminal end(s) of the alkyl group(s) may be substituted by C3-C8 cycloalkyl group).

The aryl group in (i) and (iv) may be phenyl, tollyl, xylyl or naphthyl group. The substituted cyclopentyl group in (ii) may be cyclopentylamino group or cyclopentylcarbinol group, the substituted cyclohexyl group in (ii) may be cyclohexylamino group, cyclohexylaldehyde group or cyclohexyl acetic acid group, and the substituted naphthyl group in (ii) may be naphthylamino group or naphthylamino sulfonic acid group. The condensation polycyclic hydrocarbon compound in (iii) may be pentalene, indene, naphthalene, azulene, heptalene, biphenylene, indacene, acenaphthylene, fluorene, phenalene, phenanthrene, anthracene, pentacene, hexacene, dibenzophenanthrene, 1H-cyclopentacyclooctene or benzocyclooctene, and the heterocyclic compound may be furan, thiophene, pyrrole, γ-pyran, γ-thiopyran, pyridine, thiazole, imidazole pyrimidine, indole or quinoline.

The invention is the inhibitory or blocking agents of molecular generating and/or inducing functions which has the original molecular structure shown in general formula (3-a) (3-b). And, the compounds, the derivatives or those acid addition salt compounds with effective integents provide antibacterial agents, antifungal agent, antiviral agent, bactericidal and/or sterilized agents, anticancer drugs, blood coagulation and fibrinolysis inhibitors and/or blocking agents, inhibitory and/or blocking agents of antigen-antibody reaction, organ and/or tissue preservatives, antiseptics and preservatives for foodstuffs, germination and/or maturation inhibitory agents for fruits and vegetables, antibacterial agents for plastic processing, antimicrobial coating materials, antimicrobial resin waxes, agents for preventing of bacterial and fungal proliferation and/or infection of house holding electric instruments, daily use goods and house furnishings, slime preventing agents for papers and pulps, cleaning agents in field of electronics, agents for preventing bacterial and fungal proliferation and/or infection for metal processing oil (metal working fluid), agents for preventing bacterial and fungal proliferation and/or infection for the disposal of waste, spermatocidal agents and/or contraceptive agents which aim to suppress fertility of spermatozoa, thrombolytic agents, conformation altering agents of saccharide-chains, agents for preventing arteriosclerosis, metabolism (lipids, sugar) improving agents, agents for wound healing, epithelialization promoting agents (including hair restoration effect), inhibitors and/or blocking agents which can control generation of function with bioactive substances (for example, enzymes, peptides, gene). In addition, the compounds, the derivatives or those acid addition salt compounds can inhibit and/or block function generated by multi-dimensional structure (conformation) of the substance which consist of a shape and function of living organism. Moreover, the compounds, the derivatives or those acid addition salt compounds provide chemical substances which can control, inhibit and/or block the function which is generated by multi-dimensional structure (conformation) with macromolecules substances and macromolecules composite materials as well as living organism. In addition, when halogen compounds such as halogenated alkali metals or halogenated alkali-earthy metals or halogenated zinc is added in the compounds which were provided by this invention, a reaction is able to be induced. Moreover, when gold colloid is added in the compounds which were provided by this invention, marking and/or labeling substances can be made and, it is also possible to use the compounds which were provided by this invention as dispersion (diffusion) preventives of tinction and printing dye, ink stabilizers or dye sticking agents. In addition, by using a color coupler such as dye with the compounds which were provided by this invention, coloring of the dye can be enhanced. When fragrant agents is used with the compounds which were provided in this invention, possible fragrance can be produced. In addition, the compounds, the derivatives or those acid addition salt compounds can be utilized as depolymerization agents, surface-active agents and/or surfactants, improving agents for surface active substances, phase transition agents, improving agents of phase transition, improving agents of microphase separation structure, plasticity and/or elasticity promoting agents, plasticity and/or elasticity improving agents (plasticizers), copolymerization agents, copolymerization improving agents, polymerization regulators, improving agents of polymerization adjustment, stabilizers, stabilization improving agents, antioxidants, oxidation preventing agents, improving agents of crystallized materials and/or amorphous materials, fluidability improving agents, flexibility promoters, improving agents for changing flexibility, improving agents of fluorescent wavelength and excitation wavelength of pigmentums, coating materials, cosmetic pigments and colorants, alterable agents of fluorescent wavelength and excitation wavelength of pigmentums, coating materials, cosmetic pigments and colorants. And, it is also possible to utilize the compounds, the derivatives or those acid addition salt compounds as the following improving agents. Those are agents which can improve physical property of low molecule substances, agents which can improve function of low molecule substances, agents which can improve physical property of macromolecules substance, agents which can improve function of macromolecules substances, agents which can improve physical property of macromolecules composite materials and functional macromolecules composite materials.

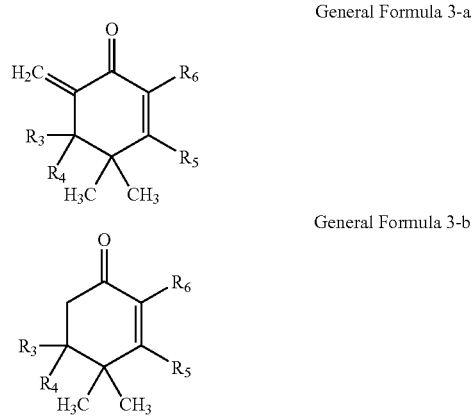

General Formula 3-a

General Formula 3-b wherein
(i) R3, R4, R5 and R6 represent independently hydrogen atom; halogen atom; C1-C6 alkyl group; amidino group; C3-C8 cycloalkyl group; C1-C6 alkoxy C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group;
(ii) one or more of R3 and R4, and/or one or more of R5 and R6 may be substituted or non-substituted cyclopentyl group; substituted or non-substituted cyclohexyl group; or substituted or non-substituted naphthyl group;
(iii) R5 and R6 may form a ring by binding with another condensation polycyclic hydrocarbon compound or heterocyclic compound;
(iv) one or more of R3, R4, R5 and R6 may be substituted by one or more of substituents selected from the group consisting of halogen atom, cyano group, protected or non-protected carboxyl group, protected or non-protected hydroxyl group, protected or non-protected amino group, C1-C6 alkyl group, C1-C6 alkoxy group, C1-C7 alkoxy carbonyl group, aryl group, C3-C6 cycloalkyl group, C1-C6 acylamino group, C1-C6 acyloxy group, C2-C6 alkenyl group, C1-C6 trihalogenoalkyl group, C1-C6 alkylamino group, and C1-C6 dialkylamino group;
(v) R5 may be substituted by one or more substituents selected from the group consisting of halogen atom, C1-C6 alkyl group, protected or non-protected carboxyl group, protected or non-protected hydroxyl group, protected or non-protected amino group, protected or non-protected C1-C6 alkylamino group, protected or non-protected C1-C6 aminoalkyl group, protected or non-protected C1-C6 alkylamino C1-C6 alkyl group, protected or non-protected hydroxyalkyl group, and C3-C6 cycloalkylamino group;
(vi) when one or more of R3, R4, R5 and R6 are alkyl groups, terminal end(s) of the alkyl group(s) may be substituted by C3-C8 cycloalkyl group).

The aryl group in (i) and (iv) may be phenyl, tollyl, xylyl or naphthyl group. The substituted cyclopentyl group in (ii) may be cyclopentylamino group or cyclopentylcarbinol group, the substituted cyclohexyl group in (ii) may be cyclohexylamino group, cyclohexylaldehyde group or cyclohexyl acetic acid group, and the substituted naphthyl group in (ii) may be naphthylamino group or naphthylamino sulfonic acid group. The condensation polycyclic hydrocarbon compound in (iii) may be pentalene, indene, naphthalene, azulene, heptalene, biphenylene, indacene, acenaphthylene, fluorene, phenalene, phenanthrene, anthracene, pentacene, hexacene, dibenzophenanthrene, 1H-cyclopentacyclooctene or benzocyclooctene, and the heterocyclic compound may be furan, thiophene, pyrrole, γ-pyran, γ-thiopyran, pyridine, thiazole, imidazole pyrimidine, indole or quinoline.

The invention in a fourth aspect provides antibacterial agents, antifungal agents, antiviral agents, bactericidal and/or sterilized agents, anticancer drugs, anticoagulants and/or antifibrinolytic agents, blood coagulation and/or fibrinolysis blocking agents, inhibitory agents of antigen-antibody reaction, preservatives for tissues and/or organs, and antiseptics and preservatives by utilizing effects on change in conformation, thermodynamic effect, phase transition effect, flexibility changing effect, depolymerization effect, improving effect of macromolecules property, chemical kinetic effect, reduction effect, effect as free radical scavengers, desulfurization effect, antioxidant effect, nucleophilic and electrophilic effects according to orbital dynamics of molecules and/or hydrophobic effect, which are inhibitory or blocking agents of molecular generating and/or inducing functions in claims 1-11.

The invention in a fifth aspect provides labeled regents which can detect a targeted position of generating function of molecule, utilizing effect on specific regions due to inhibitory or blocking agents of molecular generating and/or inducing functions in the first to third aspects, and having a labeled substance at least in one substituent.

The invention in a sixth aspect provides reductants, free radical scavengers and desufude agents utilizing inhibitory or blocking agents of molecular generating and/or inducing functions in the first to third aspects.

The invention in a seventh aspect provides depolymerization agents, improving agents for surface active substances, spermatocidal agents and/or contraceptive agents for external use, thrombolytic agents, conformation altering agents of saccharide-chains, agents for preventing arteriosclerosis, metabolism (lipids, sugar) improving agents, agents for wound healing, epithelialization promoting agents, phase transition agents, improving agents of phase transition, improving agents of microphase separation structure, plasticity and/or elasticity promoting agents, plasticity and/or elasticity improving agents (plasticizers), copolymerization agents, copolymerization improving agents, polymerization regulators, improving agents of polymerization adjustment, stabilizers, stabilization improving agents, antioxidants, oxidation preventing agents, improving agents of crystallized materials and/or amorphous materials, fluidability improving agents, flexibility promoters (softers), improving agents for changing flexibility (softner improving agents), improving agents of excitation wavelength and fluorescent wavelength of colorants, pigmentums, coating materials and cosmetic pigments, and alterable agents of excitation wavelength and fluorescent wavelength of pigmentums, coating materials and cosmetic pigments, agents which can improve physical property of low molecule substances, agents which can improve function of low molecule substances, agents which can improve physical property of macromolecules substance, agents which can improve function of macromolecules substances, agents which can improve physical property of macromolecules composite materials and functional macromolecules composite materials.

In the present specification, unless otherwise specified, the term "halogen atom" means, for example, fluorine atom, chlorine atom, bromine atom or iodine atom; the term "alkyl group" means C1-10 alkyl group such as methyl group, ethyl group, n-propyl group, isopropyl group, n-butyl group, isobutyl group, sec-butyl group, tort-butyl group, benzyl group, hexyl group, octyl group or the like; the term "lower alkyl group" means C1-5 alkyl group among the alkyl groups mentioned above; the term "alkoxy group" means —O-alkyl group (alkyl group is C1-10 alkyl group mentioned above); the term "lower alkylamino group" means C1-5 alkylamino group such as methylamino group, ethylamino group, propylamino group or the like; the term "di-lower alkylamino group" means C1-5 dialkylamino group such as dimethylamino group; the term "lower alkenyl group" means C2-5 alkenyl group such as vinyl group, allyl group, 1-propenyl group, 1-butenyl group or the like; the term "cycloalkyl group" means C3-6 cycloalkyl group such as cyclopropyl, cyclobutyl, cyclopentyl, cyclohexyl or the like; the term "aryl group" means, for example, phenyl group or naphthyl group; the term "alkoxy carbonyl group" means —COO-alkyl group (alkyl group means C1-10 alkyl group above mentioned); the term "hydroxy lower alkyl group" means hydroxy-C1-5 alkyl group such as hydroxy methyl group, hydroxy ethyl group, hydroxy propyl group or the like; the term "amino lower alkyl group" means amino C1-5 alkyl group such as aminomethyl group, aminoethyl group, aminopropyl group or the like; the term "lower alkylamino lower alkyl group" means C1-5 alkylamino C1-5 alkyl group such as methylaminomethyl group, ethylaminomethyl group, ethylaminoethyl group or the like; the term "di-lower alkylamino lower alkyl group" means C1-5 dialkylamino C1-5 alkyl group such as dimethylaminomethyl group or diethylaminomethyl group; the term "cyclic amino group" means cyclic amino group with 4-10 membered ring such as piperazinyl group, morpholinyl group, 1,4-diazabicyclo (3,2,1) octyl group or the like; the term "cyclic amino lower alkyl group" means C1-5 alkyl group attached to cyclic amino group with 4-6 membered ring such as 1-piperazinylmethyl group, 1-pyrrolidinylmethyl group, 1-azethydinylmethyl group, 1-morpholinylmethyl group or the like; the term "acylamino group" means C1-4 acylamino group such as formylamino group, acetylamino group, propionylamino group, butyrylamino group or the like; the term "acyloxy group" means C1-4 acyloxy group such as formyloxy group, acetyloxy group, propionyloxy group, butyryloxy group or the like; the term "trihalogeno-lower alkyl group" means trihalogeno C1-5 alkyl group such as trichloromethyl group, trifluoromethyl group or the like; the term "heterocyclic group" means 5 membered ring, 6 membered ring or those condensation rings (such as furyl, propyl, thienyl, oxazolyl, imidazolyl, thiazolyl, 1-pyrrolinyl, benzofuryl, benzothiazolyl, pyridyl, quinolyl, pyrimidinyl or morpholinyl group as an example) which has one or more atoms selected from the group consisting of oxygen atom, nitrogen atom and sulfate atom.

The alkyl group represented by R3, R4, R5, R6, R10 or R11 in each general formula may be either straight or branched alkyl group such as, for example, methyl group, ethyl group, propyl group, isopropyl group, butyl isobutyl group, sec-butyl group, 1-butyl group, pentyl group, isopentyl group, neopentyl group or hexyl group which are lower alkyl groups (C1-4). In addition, terminal end of these alkyl groups can be bound to lower cycloalkyl group (C3-4) such as cyclopropyl methyl group, cyclobutyl ethyl group, cyclopentyl methyl group or the like.

Lower cycloalkyl groups (C3-4) included in the cycloalkyl group represented by R3, R4, R5, R6, R10 and R11 in each general formula may be, for example, cyclopropyl group, cyclobutyl group, cyclopentyl group or cyclohexyl group. The alkoxyalkyl group may be, for example, ethyl group, methyl group, methoxyethyl group, ethoxyethyl group, propoxyethyl group, isopropoxyethyl group, butoxyethyl group, methoxypropyl group, 2-ethoxy-1-methyl ethyl group or the like.

Straight or branched alkylene group represented by R3, R4, R5, R6, R10 or R11 in each general formula may be, for example, methylene group, ethylene group, trimethylene group, tetramethylene group, 1,2-dimethylethylene group or the like.

Each substituent of R3, R4, R5, R6, R10 and R11 in each general formula or the methylene group in the general formula 3-a may be at least one substituent selected from the group consisting of halogen atom, cyano group, protected or non-protected carboxyl group, protected or non-protected hydroxyl group, protected or non-protected amino group, alkyl group, alkoxy group, alkoxy carbonyl group, aryl group, cycloalkyl group, acylamino group, acyloxy group, lower alkenyl group, trihalogeno-lower alkyl group, lower alkylamino group, di-lower alkylamino group and the like; R2 and/or R5 may be substituted by at least one substituent selected from the group consisting of halogen atom, lower alkyl group, protected or non-protected carboxyl group, protected or non-protected hydroxyl group, protected or non-protected amino group, protected or non-protected lower alkylamino group, protected or non-protected amino lower alkyl group, protected or non-protected lower alkylamino lower alkyl group, protected or non-protected hydroxy lower alkyl group, di-lower alkylamino group, di-lower alkylamino lower alkyl group or cyclic amino lower alkyl group.

Examples of the protecting substituents of carboxyl group include pharmaceutically acceptable protecting groups of carboxyl group, such as an ester-forming group which is easily detached in an organism.

Moreover, protecting substituent of amino group, amino lower alkyl group, lower alkylamino group, and lower alkylamino lower alkyl group may be a pharmaceutically acceptable amino-protecting group which is easily detached in an organism.

In addition, protecting substituent of hydroxyl group and hydroxy lower alkyl group may be a pharmaceutically acceptable protecting group of hydroxyl group which is easily detached in an organism.

Though halogen compounds can be added to the compositions according to this invention, it is necessary to give heed to an existence of toxicity which the combined compounds may have. By adding halogen compounds, coloring due to light can be prevented. Halogen compounds which can be applied to the compositions according to this invention, for example, are halogenated alkali metals such as potassium bromide, sodium bromide, potassium chloride, sodium chloride, potassium iodide and sodium iodide, and halogenated alkaline-earth metal such as calcium bromide, magnesium bromide, calcium chloride and magnesium chloride, and halogenated zinc such as zinc bromide and zinc chloride.

In addition, in the present specification, unless otherwise specified, or except for the case which is clear from a context, the term "alkyl group" includes straight alkyl group as well as branched one. Similarly, the alkyl group in "alkoxy group", "aralkyl group" and "alkylamino group" which has alkyl group includes straight alkyl group as well as branched one. "Cycloalkyl group" is also similar to the above, and includes branched groups such as ethyl cyclopentyl group and methyl cyclohexyl group.

The compounds provided in this invention can be directly applied on the surface of infected wound such as burn and decubitus. And, those can be used by combining with the carrier substances which are allowable on pharmaceutic use. In addition, when it is applied to living space, environment and at industry, those can be used during and/or after manufacturing step of materials according to the objective. Though it is not restricted to representative applications, it is also possible to be added those compounds on any manufacturing steps of surface processing by attaching, painting or spraying as agents to prevent bacterial and fungal proliferation and/or infection for construction materials, furnitures, lavatory goods, bathtub supplies, washing supplies, house holding electric instruments and/or daily use goods. Moreover, when those compounds are utilized in a thread kneading and/or later processing concerning any step of manufacturing fibers and these materials, effect of preventing bacterial and fungal proliferation and/or infection and an anti-allergic effect can be gained. An effect of the objective which is shown by claims can be made by using seats and film materials.

The carrier substances which is allowable on pharmaceutic use are given the carrier substances which is allowable biologically, such as polyoxyalkylenealkyl ether, polyoxyethylene sorbitan fatty acid ester, polyvinylpyrrolidone, hydrocarbon, paraffin, alcohol, polyvalent alcohol, alcohol ester, polyalcohol ester, fatty acid and metal salts of fatty acid. Moreover, chitosan, polyethylene glycol, polyethylene glycerin fatty acid ester (caprylic acid, capric acid, lauric acid) can be exemplified.

In addition, when the compounds mentioned in this invention are used as combined substances with the carrier substances which are allowable on pharmaceutic use, these can be applied in many kinds of the generally known agent types such as cream agents, ointments, pastes, poultices, milky lotions, suspensions, liniments, lotions, aerosol agents, solutions and tapes corresponding to prospected treatments. Also, it is allowed to add solvent supporting agents, isotonic changing agents, pH adjusters, deodorants, antiseptics or odorants in the compounds mentioned in this invention. It is also possible to be added those compounds on any manufacturing steps of surface processing by attaching, painting or spraying as agents to prevent bacterial and fungal proliferation and/or infection for construction materials, furnitures, lavatory goods, bathtub supplies, washing supplies, house holding electric instruments and/or daily use goods. Moreover, when those compounds are utilized in the thread kneading and/or later processing concerning any step of manufacturing fibers and these materials, effect of preventing bacterial and fungal proliferation and/or infection and an anti-allergic effect can be gained. An effect of the objective can be made as wall papers and filters by using seat and film material. When it is used as spermatocidal agents and contraceptive agents for external use, it is also possible to process surface of contraceptive possession such as condoms as well as ointments and creams.

Below, details of this invention are explained. Inhibitory or blocking agents of functions generated by multi-dimensional structure which are used by this invention can be completed above-mentioned objectives by use of the compounds alone, and can be utilized together with acid addition salts, emulsifiers, ester agents or polymerization agents, unless electric charge distribution and electric charge density of molecule are changed drastically. It can be used in the following form as an example; acid addition salts of the compounds which are provided in chemical formula (1-a), (1-b), (2), (3-a) and (3-b) mentioned above are non-toxic salts which are allowable pharmaceutically and, those are inorganic acids such as hydrochloric acid, hydrobromic acid, phosphoric acid or sulfuric acid and organic acids such as acetic acid, citric acid, tartaric acid, lactic acid, succinic acid, fumaric acid, maleic acid or methasulfonic acid.

Concerning chemical formula (1-a) of this invention, the following compounds in chemical formula (1-a) can be given as representatives. But, it is not restricted this invention by the definitive representatives. Concretely, as alkanes which all of R1, R2, R3, R4, R5, R6, R8 and R9 are hydrogen atom and R7 is non-cyclic hydrocarbon, for example, the following compounds are represented.

(1) 4-isopropyl-2-cyclohexen-1-one (2) 4-isobutyl-2-cyclohexen-1-one (3) 4-isopentyl-2-cyclohexen-1-one (4) 4-isohexyl-2-cyclohexen-1-one and so on.

Moreover, as amine-hydrazines which all of R1, R2, R3, R4, R5, R6, R8 and R9 are hydrogen atom and R7 is nitrogen atom, for example, (5) 4-dimethylamino-2-cyclohexen-1-one (6) 4-dimethylhydrazono-2-cyclohexen-1-one (7) 4-isopropylidenehydrazino-2-cyclohexen-1-one and so on, and those acid addition salts are exemplified.

As phosphines and those analogs which all of R1, R2, R3, R4, R5, R6, R8 and R9 are hydrogen atom and R7 is phosphorus, arsenic or antimony, for example, (8) 4-dimethylphosphinetolyl-2-cyclohexen-1-one (9) 4-dimethylallylidenetolyl-2-cyclohexen-1-one

(10) 4-dimethylstibinetolyl-2-cyclohexen-1-one

(11) 4-dimethylbismuthinetriyl-2-cyclohexen-1-one and so on, and those acid addition salts are exemplified.

As sulfide compounds which all of R1, R2, R3, R4, R5, R6, R8 and R9 are hydrogen atom and R7 is sulfate, for example,
(12) 4-isopropanesulfo-2-cyclohexen-1-one
(13) 4-isopropanesulfino-2-cyclohexen-1-one
(14) 4-isopropanesulfeno-2-cyclohexen-1-one and so on, and those acid addition salts are exemplified.

Concerning chemical formula (1-b) of this invention, the following compounds in chemical formula (1-b) can be given as representatives. But, it is not restricted this invention by the definitive representatives. Concretely, as alkanes which all of R1, R2, R3, R4, R5, R6, R8, R9, R10 and R11 are hydrogen atom and R7 is non-cyclic hydrocarbon, for example, the following compounds are represented.
(1) 4-isopropyl-cyclohexane-1-one
(2) 4-isobutyl-cyclohexane-1-one
(3) 4-isopentyl-cyclohexane-1-one
(4) 4-isohexyl-cyclohexane-1-one and so on.

As amine-hydrazines which all of R1, R2, R3, R4, R5, R6, R8, R9, R10 and R11 are hydrogen atom and R7 is nitrogen atom, for example, the following compounds are represented.
(5) 4-dimethylamino-cyclohexane-1-one
(6) 4-dimethylhydrazono-cyclohexane-1-one
(7) 4-isopropylidenehydrazino-cyclohexane-1-one and so on.

As phosphines and analogs which all of R1, R2, R3, R4, R5, R6, R8, R9, R10 and R11 are hydrogen atom and R7 is phosphorus, arsenic or antimony, for example, the following compounds are represented.
(8) 4-dimethylphosphinetriyl-cyclohexane-1-one
(9) 4-dimethylarsinetriyl-cyclohexane-1-one
(10) 4-dimethylstibinetriyl-cyclohexane-1-one
(11) 4-dimethylbismuthinetriyl-cyclohexane-1-one and so on.

As sulfide compounds which all of R1, R2, R3, R4, R5, R6, R8, R9, R10 and R11 are hydrogen atom and R7 is sulfate, for example,
(12) 4-isopropanesulfo-cyclohexane-1-one
(13) 4-isopropanesulfino-cyclohexane-1-one
(14) 4-isopropanesulfeno-cyclohexane-1-one and so on, and those acid addition salts are exemplified.

Concerning chemical formula (2) of this invention, the following compounds in chemical formula (2) can be given as representatives. But, it is not restricted this invention by the definitive representatives. Concretely, as alkanes which all of R3, R4, R5 and R6 are hydrogen atom and R1 and/or R2 are alkyl groups of non-cyclic saturated hydrocarbon, for example,
(15) 4,4,6-trimethyl-2-cyclohexen-1-one
(16) 4,4-dimethyl-6-ethyl-2-cyclohexen-1-one
(17) 4,4-dimethyl-6-propyl-2-cyclohexen-1-one
(18) 4,4-dimethyl-6-isopropyl-2-cyclohexen-1-one
(19) 6-butyl-4,4-dimethyl-2-cyclohexen-1-one
(20) 4,4-dimethyl-6-isobutyl-2-cyclohexen-1-one
(21) 6-benzyl-4,4-dimethyl-2-cyclohexen-1-one
(22) 4,4-dimethyl-6-hexyl-2-cyclohexen-1-one
(23) 4,4-dimethyl-6-octyl-2-cyclohexen-1-one and so on, and those acid addition salts are exemplified.

Moreover, when all of R3, R4, R5 and R6 are hydrogen atoms and R1 and/or R2 are alkoxy groups of heterocyclic compounds, for example,
(24) 6-pentyloxy-4,4-dimethyl-2-cyclohexen-1-one
(25) 4,4-dimethyl-6-hexyloxy-2-cyclohexen-1-one and so on, and those acid addition salts are exemplified.

When all of R3, R4, R5, R6 are hydrogen atoms and R1 and/or R2 are lower alkylamino group of amines, for example,
(26) 4,4-dimethyl-6-methylamino-2-cyclohexen-1-one
(27) 4,4-dimethyl-6-ethylamino-2-cyclohexen-1-one
(28) 4,4-dimethyl-6-propylamino-2-cyclohexen-1-one
(29) 4,4-dimethyl-6-dimethylamino-2-cyclohexen-1-one and so on, and those acid addition salts are exemplified.

Moreover, when all of R3, R4, R5 and R6 are hydrogen atoms and R1 and/or R2 are alkenyl groups of non-cyclic unsaturation hydrocarbon, for example,
(30) 6-vinyl-4,4-dimethyl-2-cyclohexen-1-one
(31) 6-allyl-4,4-dimethyl-2-cyclohexen-1-one
(32) 4,4-dimethyl-6-isopropenyl-2-cyclohexen-1-one and so on, and those acid addition salts are exemplified.

Moreover, when all of R3, R4, R5 and R6 are hydrogen atoms and R1 and/or R2 are cycloalkyl group of monocyclic hydrocarbon, for example,
(32) 6-cyclopropyl-4,4-dimethyl-2-cyclohexen-1-one
(32) 6-cyclobutyl-4,4-dimethyl-2-cyclohexen-1-one
(32) 6-cyclopentyl-4,4-dimethyl-2-cyclohexen-1-one
(32) 6-cyclohexyl-4,4-dimethyl-2-cyclohexen-1-one and so on, and those acid additions are exemplified.

Moreover, when all of R3, R4, R5 and R6 are hydrogen atoms and R1 and/or R2 are allyl group of aromatic hydrocarbon 1 valence group, for example,
(32) 4,4-dimethyl-6-phenyl-2-cyclohexen-1-one
(32) 4,4-dimethyl-6-naphthyl-2-cyclohexen-1-one and so on, and those acid addition salts are exemplified.

All of R3, R4, R5 and R6 may be hydrogen atoms and R1 and/or R2 may be alkoxy carbonyl groups as ester. In addition, when all of R3, R4, R5 and R6 are hydrogen atoms and R1 and/or R2 are hydroxy lower alkyl group, for example,
(33) 4,4-dimethyl-6-hydroxymethyl-2-cyclohexen-1-one
(34) 4,4-dimethyl-6-hydroxyethyl-2-cyclohexen-1-one
(35) 4,4-dimethyl-6-hydroxypropyl-2-cyclohexen-1-one and so on, and those acid addition salts are exemplified.

Moreover, when all of R3, R4, R5 and R6 are hydrogen atoms and R1 and/or R2 are amino lower alkyl group, for example,
(36) 6-aminomethyl-4,4-dimethyl-2-cyclohexen-1-one
(37) 6-aminoethyl-4,4-dimethyl-2-cyclohexen-1-one
(38) 6-aminopropyl-4,4-dimethyl-2-cyclohexen-1-one and so on, and those acid addition salts are exemplified.

Moreover, when all of R3, R4, R5 and R6 are hydrogen atoms and R1 and/or R2 are lower alkylamino lower alkyl group, for example,
(39) 4,4-dimethyl-6-methylaminomethyl-2-cyclohexen-1-one
(40) 4,4-dimethyl-6-ethylaminomethyl-2-cyclohexen-1-one
(41) 4,4-dimethyl-6-ethylaminoethyl-2-cyclohexen-1-one so on, and those acid addition salts are exemplified.

Moreover, when all of R3, R4, R5 and R6 are hydrogen atoms and R1 and/or R2 are di-lower alkylamino lower alkyl group, for example,
(42) 4,4-dimethyl-6-dimethylaminomethyl-2-cyclohexen-1-one
(43) 4,4-dimethyl-6-diethylaminomethyl-2-cyclohexen-1-one and so on, and those acid addition salts are exemplified.

Moreover, when all of R3, R4, R5 and R6 are hydrogen atoms and R1 and/or R2 are cyclic amino groups, for example,
(44) 4,4-dimethyl-6-piperazinyl-2-cyclohexen-1-one
(45) 4,4-dimethyl-6-morpholinyl-2-cyclohexen-1-one and so on, and those acid addition salts are exemplified.

Moreover, when all of R3, R4, R5 and R6 are hydrogen atoms and R1 and/or R2 are cyclic amino lower alkyl group, for example,
(46) 4,4-dimethyl-6-piperazinylethyl-2-cyclohexen-1-one
(47) 4,4-dimethyl-6-pyrrolinylmethyl-2-cyclohexen-1-one
(48) 6-azethydinylmethyl-4,4-dimethyl-2-cyclohexen-1-one
(49) 4,4-dimethyl-6-morpholinylmethyl-2-cyclohexen-1-one, and so on, and those acid addition salts are exemplified.

Moreover, when all of R3, R4, R5 and R6 are hydrogen atoms and R1 and/or R2 are acylamino group of monoacylamin group, for example,
(50) 4,4-dimethyl-6-formylamino-2-cyclohexen-1-one
(51) 6-acetylamino-4,4-dimethyl-2-cyclohexen-1-one
(52) 4,4-dimethyl-6-propionylamino-2-cyclohexen-1-one
(53) 6-butyrylamino-4,4-dimethyl-2-cyclohexen-1-one and so on, and those acid addition salts are exemplified.

Moreover, when all of R3, R4, R5 and R6 are hydrogen atoms and R1 and/or R2 are acyloxy group of ester, for example,
(54) 4,4-dimethyl-6-formyloxy-2-cyclohexen-1-one
(55) 6-acetyloxy-4,4-dimethyl-2-cyclohexen-1-one
(56) 4,4-dimethyl-6-propionyloxy-2-cyclohexen-1-one
(57) 6-butyryloxy-4,4-dimethyl-2-cyclohexen-1-one and so on, and those acid addition salts are exemplified.

Moreover, when all of R3, R4, R5 and R6 are hydrogen atoms and R1 and/or R2 are trihalogeno lower alkyl group, for example,
(58) 4,4-dimethyl-6-trichloromethyl-2-cyclohexen-1-one
(59) 4,4-dimethyl-6-trifluoromethyl-2-cyclohexen-1-one and so on, and those acid addition salts are exemplified.

Moreover, when all of R3, R4, R5 and R6 are hydrogen atoms and R1 and/or R2 are polycyclic group, for example,
(60) 4,4-dimethyl-6-furyl-2-cyclohexen-1-one
(61) 4,4-dimethyl-6-propyl-2-cyclohexen-1-one
(62) 4,4-dimethyl-6-thienyl-2-cyclohexen-1-one
(63) 4,4-dimethyl-6-isoxazolyl-2-cyclohexen-1-one
(64) 4,4-dimethyl-6-imidazolyl-2-cyclohexen-1-one
(65) 4,4-dimethyl-6-thiazolyl-2-cyclohexen-1-one
(66) 4,4-dimethyl-6-pyrrolinyl-2-cyclohexen-1-one
(67) 6-benzofuryl-4,4-dimethyl-2-cyclohexen-1-one
(68) 6-benzothiazolyl-4,4-dimethyl-2-cyclohexen-1-one
(69) 6-pyridyl-4,4-dimethyl-2-cyclohexen-1-one
(70) 4,4-dimethyl-6-quinolyl-2-cyclohexen-1-one
(71) 4,4-dimethyl-6-pyrimidinyl-2-cyclohexen-1-one
(72) 4,4-dimethyl-6-morpholinyl-2-cyclohexen-1-one and so on, and those acid addition salts are exemplified.

Concerning this invention, in the compounds provided by chemical formula (3-a), the compound which all of substituent R3, R4, R5 are R6 in chemical formula (3-a) are hydrogen atoms represents 4,4-dimethyl-6-methylene-2-cyclohexen-1-one, which is termed as Yoshixol. And, as other representatives, the following compounds can be given as representatives. But, it is not restricted this invention by the definitive representatives. Concretely, for example, when all of substituent R3 and/or R4 are alkyl group of non-cyclic saturated hydrocarbon,
(73) 6-methylene-4,4,5-trimethyl-2-cyclohexen-1-one
(74) 4,4-dimethyl-5-ethyl-6-methylene-2-cyclohexen-1-one
(75) 4,4-dimethyl-5-propyl-6-methylene-2-cyclohexen-1-one
(76) 4,4-dimethyl-5-isopropyl-6-methylene-2-cyclohexen-1-one
(77) 5-butyl-4,4-dimethyl-6-methylene-2-cyclohexen-1-one
(78) 4,4-dimethyl-5-isobutyl-6-methylene-2-cyclohexen-1-one
(79) 5-benzyl-4,4-dimethyl-6-methylene-2-cyclohexen-1-one
(80) 4,4-dimethyl-5-hexyl-6-methylene-2-cyclohexen-1-one
(81) 4,4-dimethyl-5-octyl-6-methylene-2-cyclohexen-1-one and so on, and those acid addition salts are exemplified.

For example, when substituent R3 and/or R4 are alkoxy group of heterocyclic compound,
(82) 5-pentyloxy-4,4-dimethyl-6-methylene-2-cyclohexen-1-one
(83) 4,4-dimethyl-5-hexyloxy-6-methylene-2-cyclohexen-1-one and so on, and those acid addition salts are exemplified.

For example, when substituent R3 and/or R4 are lower alkylamino group of amines,
(84) 4,4-dimethyl-5-methylamino-6-methylene-2-cyclohexen-1-one
(85) 4,4-dimethyl-5-ethylamino-6-methylene-2-cyclohexen-1-one
(86) 4,4-dimethyl-5-propylamino-6-methylene-2-cyclohexen-1-one
(87) 4,4-dimethyl-5-dimethylamino-6-methylene-2-cyclohexen-1-one and so on, and those acid addition salts are exemplified. For example, when substituent R3 and/or R4 are alkenyl group of non-cyclic unsaturation hydrocarbon,
(88) 5-vinyl-4,4-dimethyl-6-methylene-2-cyclohexen-1-one
(89) 5-allyl-4,4-dimethyl-6-methylene-2-cyclohexen-1-one
(90) 4,4-dimethyl-5-isopropenyl-6-methylene-2-cyclohexen-1-one and so on, and those acid addition salts are exemplified.

For example, when substituent R3 and/or R4 are cycloalkyl group of monocyclic hydrocarbon,
(91) 5-cyclopropyl-4,4-dimethyl-6-methylene-2-cyclohexen-1-one
(92) 5-cyclobutyl-4,4-dimethyl-6-methylene-2-cyclohexen-1-one
(93) 5-cyclopentyl-4,4-dimethyl-6-methylene-2-cyclohexen-1-one
(94) 5-cyclohexyl-4,4-dimethyl-6-methylene-2-cyclohexen-1-one and so on, and those acid addition salts are exemplified.

For example, when substituent R3 and/or R4 are allyl group of aromatic hydrocarbon 1 valence group,
(95) 4,4-dimethyl-5-phenyl-6-methylene-2-cyclohexen-1-one
(96) 4,4-dimethyl-5-naphthyl-6-methylene-2-cyclohexen-1-one and so on, and those acid addition salts are exemplified.

Substituent R3, R4 are sometimes alkoxy carbonyl group aromatic hydrocarbon 1 valence group allyl group of ester.
(98) 4,4-dimethyl-5-hydroxy methyl-6-methylene-2-cyclohexen-1-one
(99) 4,4-dimethyl-5-hydroxy ethyl-6-methylene-2-cyclohexen-1-one
(100) 4,4-dimethyl-5-hydroxy propyl-6-methylene-2-cyclohexen-1-one and so on, and those acid addition salts are exemplified.

For example, when substituent R3 and/or R4 are amino lower alkyl group,
(101) 5-aminomethyl-4,4-dimethyl-6-methylene-2-cyclohexen-1-one
(102) 5-aminoethyl-4,4-dimethyl-6-methylene-2-cyclohexen-1-one
(103) 5-aminopropyl-4,4-dimethyl-6-methylene-2-cyclohexen-1-one and so on, and those acid addition salts are exemplified.

For example, when substituent R3 and/or R4 are lower alkylamino lower alkyl group,
- (104) 4,4-dimethyl-5-methylaminomethyl-6-methylene-2-cyclohexen-1-one
- (105) 4,4-dimethyl-5-ethylaminomethyl-6-methylene-2-cyclohexen-1-one
- (106) 4,4-dimethyl-5-ethylaminoethyl-6-methylene-2-cyclohexen-1-one and so on, and those acid addition salts are exemplified.

For example, when-substituent R3 and/or R4 are di-lower alkylamino lower alkyl group,
- (107) 4,4-dimethyl-5-dimethylaminomethyl-6-methylene-2-cyclohexen-1-one
- (108) 4,4-dimethyl-5-diethylaminomethyl-6-methylene-2-cyclohexen-1-one and so on, and those acid addition salts are exemplified.

For example, when substituent R3 and/or R4 are cyclic amino groups,
- (109) 4,4-dimethyl-5-piperazinyl-6-methylene-2-cyclohexen-1-one
- (110) 4,4-dimethyl-5-morpholinyl-6-methylene-2-cyclohexen-1-one and so on, and those acid addition salts are exemplified.

For example, when substituent R3 and/or R4 are cycloamino lower alkyl group,
- (111) 4,4-dimethyl-5-piperazinyl ethyl-6-methylene-2-cyclohexen-1-one
- (112) 4,4-dimethyl-5-pyrrolinyl methyl-6-methylene-2-cyclohexen-1-one
- (113) 5-azethydinylmethyl-4,4-dimethyl-6-methylene-2-cyclohexen-1-one
- (114) 4,4-dimethyl-5-morpholinylmethyl-6-methylene-2-cyclohexen-1-one and so on, and those acid addition salts are exemplified.

For example, when substituent R3 and/or R4 are acylamino group of monoacylamin group,
- (115) 4,4-dimethyl-5-formylamino-6-methylene-2-cyclohexen-1-one
- (116) 5-acetylamino-4,4-dimethyl-6-methylene-2-cyclohexen-1-one
- (117) 4,4-dimethyl-5-propionylamino-6-methylene-2-cyclohexen-1-one
- (118) 5-butyrylamino-4,4-dimethyl-6-methylene-2-cyclohexen-1-one and so on, and those acid addition salts are exemplified. For example, when substituent R3 and/or R4 are acyloxy group of ester,
- (119) 4,4-dimethyl-5-formyloxy-6-methylene-2-cyclohexen-1-one
- (120) 5-acetyloxy-4,4-dimethyl-6-methylene-2-cyclohexen-1-one
- (121) 4,4-dimethyl-5-propionyloxy-6-methylene-2-cyclohexen-1-one
- (122) 5-butyryloxy-4,4-dimethyl-6-methylene-2-cyclohexen-1-one and so on, and those acid addition salts are exemplified.

For example, when substituent R3 and/or R4 are trihalogeno lower alkyl group,
- (123) 4,4-dimethyl-5-trichloromethyl-6-methylene-2-cyclohexen-1-one
- (124) 4,4-dimethyl-5-trifluoromethyl-6-methylene-2-cyclohexen-1-one and so on, and those acid addition salts are exemplified.

For example, when substituent R3 and/or R4 are polycyclic group,
- (125) 4,4-dimethyl-5-furyl-6-methylene-2-cyclohexen-1-one
- (126) 4,4-dimethyl-5-propyl-6-methylene-2-cyclohexen-1-one
- (127) 4,4-dimethyl-5-thienyl-6-methylene-2-cyclohexen-1-one
- (128) 4,4-dimethyl-5-isoxazolyl-6-methylene-2-cyclohexen-1-one
- (129) 4,4-dimethyl-5-imidazolyl-6-methylene-2-cyclohexen-1-one
- (130) 4,4-dimethyl-5-thiazolyl-6-methylene-2-cyclohexen-1-one
- (131) 4,4-dimethyl-5-pyrrolinyl-6-methylene-2-cyclohexen-1-one
- (132) 5-benzofuryl-4,4-dimethyl-6-methylene-2-cyclohexen-1-one
- (133) 5-benzothiazolyl-4,4-dimethyl-6-methylene-2-cyclohexen-1-one
- (134) 5-pyridyl-4,4-dimethyl-6-methylene-2-cyclohexen-1-one
- (135) 4,4-dimethyl-5-quinolyl-6-methylene-2-cyclohexen-1-one
- (136) 4,4-dimethyl-5-pyrimidinyl-6-methylene-2-cyclohexen-1-one
- (137) 4,4-dimethyl-5-morpholinyl-6-methylene-2-cyclohexen-1-one and so on, and those acid addition salts are exemplified. For example, when substituent R5 is alkyl group of non-cyclic saturated hydrocarbon,
- (138) 3,4,4-trimethyl-6-methylene-2-cyclohexen-1-one
- (139) 4,4-dimethyl-3-ethyl-6-methylene-2-cyclohexen-1-one
- (140) 4,4-dimethyl-6-methylene-3-propyl-2-cyclohexen-1-one
- (141) 4,4-dimethyl-3-isopropyl-6-methylene-2-cyclohexen-1-one
- (142) 3-butyl-4,4-dimethyl-6-methylene-2-cyclohexen-1-one
- (143) 4,4-dimethyl-3-isobutyl-6-methylene-2-cyclohexen-1-one
- (144) 3-benzyl-4,4-dimethyl-6-methylene-2-cyclohexen-1-one
- (145) 4,4-dimethyl-3-hexyl-6-methylene-2-cyclohexen-1-one
- (146) 4,4-dimethyl-6-methylene-3-octyl-2-cyclohexen-1-one and so on, and those acid addition salts are exemplified.

For example, when substituent R5 is alkoxy group of heterocyclic compound,
- (147) 3-pentyloxy-4,4-dimethyl-6-methylene-2-cyclohexen-1-one
- (148) 4,4-dimethyl-3-hexyloxy-6-methylene-2-cyclohexen-1-one and so on, and those acid addition salts are exemplified.

For example, when substituent R5 is lower alkylamino group of amine group,
- (149) 4,4-dimethyl-3-methylamino-6-methylene-2-cyclohexen-1-one
- (150) 4,4-dimethyl-3-ethylamino-6-methylene-2-cyclohexen-1-one
- (151) 4,4-dimethyl-6-methylene-3-propylamino-2-cyclohexen-1-one
- (152) 4,4-dimethyl-3-dimethylamino-6-methylene-2-cyclohexen-1-one and so on, and those acid addition salts are exemplified.

For example, when substituent R5 is alkenyl group of non-cyclic unsaturation hydrocarbon,
(153) 3-vinyl-4,4-dimethyl-6-methylene-2-cyclohexen-1-one
(154) 3-allyl-4,4-dimethyl-6-methylene-2-cyclohexen-1-one
(155) 4,4-dimethyl-3-isopropenyl-6-methylene-2-cyclohexen-1-one and so on, and those acid addition salts are exemplified. For example, when substituent R5 is cycloalkyl group of monocyclic hydrocarbon,
(156) 3-cyclopropyl-4,4-dimethyl-6-methylene-2-cyclohexen-1-one
(157) 3-cyclobutyl-4,4-dimethyl-6-methylene-2-cyclohexen-1-one
(158) 3-cyclopentyl-4,4-dimethyl-6-methylene-2-cyclohexen-1-one
(159) 3-cyclohexyl-4,4-dimethyl-6-methylene-2-cyclohexen-1-one and so on, and those acid addition salts are exemplified. For example, when substituent R5 is allyl group of aromatic hydrocarbon 1 valence group,
(160) 4,4-dimethyl-3-phenyl-6-methylene-2-cyclohexen-1-one
(161) 4,4-dimethyl-6-methylene-3-naphthyl-2-cyclohexen-1-one and so on, and those acid addition salts are exemplified.

Substituent R5 is alkoxy carbonyl group and the compound becomes ester. For example, when substituent R5 is hydroxy lower alkyl group,
(163) 4,4-dimethyl-3-hydroxy methyl-6-methylene-2-cyclohexen-1-one
(164) 4,4-dimethyl-3-hydroxy ethyl-6-methylene-2-cyclohexen-1-one
(165) 4,4-dimethyl-3-hydroxy propyl-6-methylene-2-cyclohexen-1-one and so on, and those acid addition salts are exemplified.

For example, when substituent R5 is an amino lower alkyl group,
(166) 3-aminomethyl-4,4-dimethyl-6-methylene-2-cyclohexen-1-one
(167) 3-aminoethyl-4,4-dimethyl-6-methylene-2-cyclohexen-1-one
(168) 3-aminopropyl-4,4-dimethyl-6-methylene-2-cyclohexen-1-one and so on, and those acid addition salts are exemplified. For example, when substituent R5 is a lower alkylamino lower alkyl group,
(169) 4,4-dimethyl-3-methylaminomethyl-6-methylene-2-cyclohexen-1-one
(170) 4,4-dimethyl-3-ethylaminomethyl-6-methylene-2-cyclohexen-1-one
(171) 4,4-dimethyl-3-ethylaminoethyl-6-methylene-2-cyclohexen-1-one and so on, and those acid addition salts are exemplified.

For example, when substituent R5 is a lower alkylamino lower alkyl group,
(172) 3-dimethylaminomethyl-4,4-dimethyl-6-methylene-2-cyclohexen-1-one
(173) 3-diethylaminomethyl-4,4-dimethyl-6-methylene-2-cyclohexen-1-one and so on, and those acid addition salts are exemplified.

For example, when substituent R5 is cyclic amino group,
(174) 4,4-dimethyl-6-methylene-3-piperazinyl-2-cyclohexen-1-one
(175) 4,4-dimethyl-6-methylene-3-morpholinyl-2-cyclohexen-1-one and so on, and those acid addition salts are exemplified. For example, when substituent R5 is cyclic amino lower alkyl group,
(176) 4,4-dimethyl-6-methylene-3-piperazinyl ethyl-2-cyclohexen-1-one
(177) 4,4-dimethyl-6-methylene-3-pyrrolinyl methyl-2-cyclohexen-1-one
(178) 3-azethydinylmethyl-4,4-dimethyl-6-methylene-2-cyclohexen-1-one
(179) 4,4-dimethyl-6-methylene-3-morpholinylmethyl-2-cyclohexen-1-one and so on, and those acid addition salts are exemplified.

For example, when substituent R5 is acylamino group of monoacylamin,
(180) 4,4-dimethyl-3-formylamino-6-methylene-2-cyclohexen-1-one
(181) 3-acetylamino-4,4-dimethyl-6-methylene-2-cyclohexen-1-one
(182) 4,4-dimethyl-6-methylene-3-propionylamino-2-cyclohexen-1-one
(183) 3-butyrylamino-4,4-dimethyl-6-methylene-2-cyclohexen-1-one and so on, and those acid addition salts are exemplified. For example, when substituent R5 is acyloxy group of ester,
(184) 4,4-dimethyl-3-formyloxy-6-methylene-2-cyclohexen-1-one
(185) 3-acetyloxy-4,4-dimethyl-6-methylene-2-cyclohexen-1-one
(186) 4,4-dimethyl-6-methylene-3-propionyloxy-2-cyclohexen-1-one
(187) 3-butyryloxy-4,4-dimethyl-6-methylene-2-cyclohexen-1-one and so on, and those acid addition salts are exemplified. For example, when substituent R5 is a trihalogeno lower alkyl group,
(188) 4,4-dimethyl-6-methylene-3-trichloromethyl-2-cyclohexen-1-one
(189) 4,4-dimethyl-6-methylene-3-trifluoromethyl-2-cyclohexen-1-one and so on, and those acid addition salts are exemplified.

For example, when substituent R5 is polycyclic group,
(190) 4,4-dimethyl-3-furyl-6-methylene-2-cyclohexen-1-one
(191) 4,4-dimethyl-6-methylene-3-propyl-2-cyclohexen-1-one
(192) 4,4-dimethyl-6-methylene-3-thienyl-2-cyclohexen-1-one
(193) 4,4-dimethyl-3-isoxazolyl-6-methylene-2-cyclohexen-1-one
(194) 4,4-dimethyl-3-imidazolyl-6-methylene-2-cyclohexen-1-one
(195) 4,4-dimethyl-6-methylene-3-thiazolyl-2-cyclohexen-1-one
(196) 4,4-dimethyl-6-methylene-3-pyrrolinyl-2-cyclohexen-1-one,
(197) 3-benzofuryl-4,4-dimethyl-6-methylene-2-cyclohexen-1-one
(198) 3-benzothiazolyl-4,4-dimethyl-6-methylene-2-cyclohexen-1-one
(199) 3-pyridyl-4,4-dimethyl-6-methylene-2-cyclohexen-1-one
(200) 4,4-dimethyl-6-methylene-3-quinolyl-2-cyclohexen-1-one
(201) 4,4-dimethyl-6-methylene-3-pyrimidinyl-2-cyclohexen-1-one
(202) 4,4-dimethyl-6-methylene-3-morpholinyl-2-cyclohexen-1-one and so on, and those acid addition salts are exemplified. For example, when substituent R6 is alkyl group of non-cyclic saturated hydrocarbon,
(203) 6-methylene-2,4,4-trimethyl-2-cyclohexen-1-one (204) 4,4-dimethyl-2-ethyl-6-methylene-2-cyclohexen-1-one
(205) 4,4-dimethyl-6-methylene-2-propyl-2-cyclohexen-1-one
(206) 4,4-dimethyl-2-isopropyl-6-methylene-2-cyclohexen-1-one
(207) 2-butyl-4,4-dimethyl-6-methylene-2-cyclohexen-1-one
(208) 4,4-dimethyl-2-isobutyl-6-methylene-2-cyclohexen-1-one
(209) 2-benzyl-4,4-dimethyl-6-methylene-2-cyclohexen-1-one
(210) 4,4-dimethyl-2-hexyl-6-methylene-2-cyclohexen-1-one
(211) 4,4-dimethyl-6-methylene-2-octyl-2-cyclohexen-1-one and so on, and those acid addition salts are exemplified.

For example, when substituent R6 is alkoxy group of heterocyclic compound,
(212) 2-pentyloxy-4,4-dimethyl-6-methylene-2-cyclohexen-1-one
(213) 4,4-dimethyl-2-hexyloxy-6-methylene-2-cyclohexen-1-one and so on, and those acid addition salts are exemplified.

For example, when substituent R6 is a lower alkylamino group of amines,
(214) 4,4-dimethyl-2-methylamino-6-methylene-2-cyclohexen-1-one
(215) 4,4-dimethyl-2-ethylamino-6-methylene-2-cyclohexen-1-one
(216) 4,4-dimethyl-6-methylene-2-propylamino-2-cyclohexen-1-one
(217) 2-dimethylamino-4,4-dimethyl-6-methylene-2-cyclohexen-1-one and so on, and those acid addition salts are exemplified.

For example, when substituent R6 is alkenyl group of noncyclic saturated hydrocarbon,
(218) 2-vinyl-4,4-dimethyl-6-methylene-2-cyclohexen-1-one
(219) 2-allyl-4,4-dimethyl-6-methylene-2-cyclohexen-1-one
(220) 4,4-dimethyl-2-isopropenyl-6-methylene-2-cyclohexen-1-one and so on, and those acid addition salts are exemplified. For example, when substituent R6 is cycloalkyl group of monocyclic hydrocarbon,
(221) 2-cyclopropyl-4,4-dimethyl-6-methylene-2-cyclohexen-1-one
(222) 2-cyclobutyl-4,4-dimethyl-6-methylene-2-cyclohexen-1-one
(223) 2-cyclopentyl-4,4-dimethyl-6-methylene-2-cyclohexen-1-one
(224) 2-cyclohexyl-4,4-dimethyl-6-methylene-2-cyclohexen-1-one and so on, and those acid addition salts are exemplified. For example, when substituent R6 is allyl group of aromatic hydrocarbon 1 valence group,
(225) 4,4-dimethyl-2-phenyl-6-methylene-2-cyclohexen-1-one
(226) 4,4-dimethyl-6-methylene-2-naphthyl-2-cyclohexen-1-one and so on, and those acid addition salts are exemplified.

Substituent R6 is alkoxy carbonyl group resulting in ester. For example, when substituent R6 is a hydroxy lower alkyl group,
(228) 4,4-dimethyl-2-hydroxy methyl-6-methylene-2-cyclohexen-1-one
(229) 4,4-dimethyl-2-hydroxy ethyl-6-methylene-2-cyclohexen-1-one
(230) 4,4-dimethyl-2-hydroxy propyl-6-methylene-2-cyclohexen-1-one and so on, and those acid addition salts are exemplified.

For example, when substituent R6 is an amino lower alkyl group,
(231) 2-aminomethyl-4,4-dimethyl-6-methylene-2-cyclohexen-1-one
(232) 2-aminoethyl-4,4-dimethyl-6-methylene-2-cyclohexen-1-one
(233) 2-aminopropyl-4,4-dimethyl-6-methylene-2-cyclohexen-1-one and so on, and those acid addition salts are exemplified. For example, when substituent R6 is a lower alkylamino lower alkyl group,
(234) 4,4-dimethyl-2-methylaminomethyl-6-methylene-2-cyclohexen-1-one
(235) 4,4-dimethyl-2-ethylaminomethyl-6-methylene-2-cyclohexen-1-one
(236) 4,4-dimethyl-2-ethylaminoethyl-6-methylene-2-cyclohexen-1-one and so on, and those acid addition salts are exemplified.

For example, when substituent R6 is a di-lower alkylamino lower alkyl group,
(237) 2-dimethylaminomethyl-4,4-dimethyl-6-methylene-2-cyclohexen-1-one
(238) 2-diethylaminomethyl-4,4-dimethyl-6-methylene-2-cyclohexen-1-one and so on, and those acid addition salts are exemplified.

For example, when substituent R6 is cyclic amino group,
(239) 4,4-dimethyl-6-methylene-2-piperazinyl-2-cyclohexen-1-one
(240) 4,4-dimethyl-6-methylene-2-morpholinyl-2-cyclohexen-1-one and so on, and those acid addition salts are exemplified. For example, when substituent R6 is a cyclic amino lower alkyl group,
(241) 4,4-dimethyl-6-methylene-2-piperazinyl ethyl-2-cyclohexen-1-one
(242) 4,4-dimethyl-6-methylene-2-pyrrolinyl methyl-2-cyclohexen-1-one
(243) 2-azethydinylmethyl-4,4-dimethyl-6-methylene-2-cyclohexen-1-one
(244) 4,4-dimethyl-6-methylene-2-morpholinylmethyl-2-cyclohexen-1-one and so on, and those acid addition salts are exemplified.

For example, when substituent R6 is acylamino group of monoacylamin,
(245) 4,4-dimethyl-2-formylamino-6-methylene-2-cyclohexen-1-one
(246) 2-acetylamino-4,4-dimethyl-6-methylene-2-cyclohexen-1-one
(247) 4,4-dimethyl-6-methylene-2-propionylamino-2-cyclohexen-1-one
(248) 2-butyrylamino-4,4-dimethyl-6-methylene-2-cyclohexen-1-one and so on, and those acid addition salts are exemplified. For example, when substituent R6 is acyloxy group of ester,
(249) 4,4-dimethyl-2-formyloxy-6-methylene-2-cyclohexen-1-one
(250) 2-acetyloxy-4,4-dimethyl-6-methylene-2-cyclohexen-1-one
(251) 4,4-dimethyl-6-methylene-2-propionyloxy-2-cyclohexen-1-one
(252) 2-butyryloxy-4,4-dimethyl-6-methylene-2-cyclohexen-1-one and so on, and those acid addition salts are exemplified. For example, when substituent R6 is a trihalogeno lower alkyl group, (253) 4,4-dimethyl-6-methylene-2-trichloromethyl-2-cyclohexen-1-one
(254) 4,4-dimethyl-6-methylene-2-trifluoromethyl-2-cyclohexen-1-one and so on, and those acid addition salts are exemplified. For example, when substituent R6 is polycyclic group,
(255) 4,4-dimethyl-2-furyl-6-methylene-2-cyclohexen-1-one
(256) 4,4-dimethyl-6-methylene-2-propyl-2-cyclohexen-1-one
(257) 4,4-dimethyl-6-methylene-2-thienyl-2-cyclohexen-1-one
(258) 4,4-dimethyl-2-isoxazolyl-6-methylene-2-cyclohexen-1-one
(259) 4,4-dimethyl-2-imidazolyl-6-methylene-2-cyclohexen-1-one
(260) 4,4-dimethyl-6-methylene-2-thiazolyl-2-cyclohexen-1-one
(261) 4,4-dimethyl-6-methylene-2-pyrrolinyl-2-cyclohexen-1-one
(262) 2-benzofuryl-4,4-dimethyl-6-methylene-2-cyclohexen-1-one
(263) 2-benzothiazolyl-4,4-dimethyl-6-methylene-2-cyclohexen-1-one
(264) 2-pyridyl-4,4-dimethyl-6-methylene-2-cyclohexen-1-one
(265) 4,4-dimethyl-6-methylene-2-quinolyl-2-cyclohexen-1-one
(267) 4,4-dimethyl-6-methylene-2-pyrimidinyl-2-cyclohexen-1-one
(268) 4,4-dimethyl-6-methylene-2-morpholinyl-2-cyclohexen-1-one and so on, and those acid addition salts are exemplified. For example, when R5 and/or R6 in chemical formula (3-a) are bond substituent such as condensation polycyclic hydrocarbons and heterocyclic compounds,
(269) 5H-4-dimethyl-6-methylene-7-oxo-indene
(270) 4-dimethyl-2-methylene-1-oxo-tetralin
(271) 3H-4-dimethyl-2-methylene-1-oxo-anthracene
(272) 5H-4-dimethyl-6-methylene-7-oxo-benzothiophene
(273) 5H-4-dimethyl-6-methylene-7-oxo-benzofuran
(274) 5H-4-dimethyl-6-methylene-7-oxo-indole
(275) 6H-5-dimethyl-7-methylene-8-oxo-quinoline
(276) 6H-5-dimethyl-7-methylene-8-oxo-quinoxaline
(277) 6H-5-dimethyl-7-methylene-8-oxo-cinnoline
(278) 5H-5-dimethyl-7-methylene-8-oxo-1,4 dithianaphthalene
(279) 3H-4-dimethyl-2-methylene-1-oxo-thianthrene and so on, and those acid addition salts are exemplified.

Concerning this invention, in the compounds provided by chemical formula (3-b), the compound which all of substituent R3, R4, R5 are R6 in chemical formula (3-b) are hydrogen atoms represents 4,4-dimethyl-2-cyclohexen-1-one. And, as other representatives, the following compounds can be given as representatives. But, it is not restricted this invention by the definitive representatives.

Concretely, when all of substituent R3 and/or R4 are alkyl group of non-cyclic saturated hydrocarbon,
(280) 4,4,5-trimethyl-2-cyclohexen-1-one
(281) 4,4-dimethyl-5-ethyl-2-cyclohexen-1-one
(282) 4,4-dimethyl-5-propyl-2-cyclohexen-1-one
(283) 4,4-dimethyl-5-isopropyl-2-cyclohexen-1-one
(284) 5-butyl-4,4-dimethyl-2-cyclohexen-1-one
(285) 4,4-dimethyl-5-isobutyl-2-cyclohexen-1-one
(286) 5-benzyl-4,4-dimethyl-2-cyclohexen-1-one
(287) 4,4-dimethyl-5-hexyl-2-cyclohexen-1-one
(288) 4,4-dimethyl-5-octyl-2-cyclohexen-1-one and so on, and those acid addition salts are exemplified.

For example, when substituent R3 and/or R4 are alkoxy groups of heterocyclic compound,
(289) 5-pentyloxy-4,4-dimethyl-2-cyclohexen-1-one
(290) 4,4-dimethyl-5-hexyloxy-2-cyclohexen-1-one and so on, and those acid addition salts are exemplified. For example, when substituent R3 and/or R4 are lower alkylamino group of amines,
(291) 4,4-dimethyl-5-methylamino-2-cyclohexen-1-one
(292) 4,4-dimethyl-5-ethylamino-2-cyclohexen-1-one
(293) 4,4-dimethyl-5-propylamino-2-cyclohexen-1-one
(294) 4,4-dimethyl-5-dimethylamino-2-cyclohexen-1-one and so on, and those acid addition salts are exemplified.

For example, when substituent R3 and/or R4 are alkenyl group of non-cyclic unsaturation hydrocarbon,
(295) 5-vinyl-4,4-dimethyl-2-cyclohexen-1-one
(296) 5-allyl-4,4-dimethyl-2-cyclohexen-1-one
(297) 4,4-dimethyl-5-isopropenyl-2-cyclohexen-1-one and so on, and those acid addition salts are exemplified.

For example, when substituent R3 and/or R4 are cycloalkyl group of monocyclic hydrocarbon,
(298) 5-cyclopropyl-4,4-dimethyl-2-cyclohexen-1-one
(299) 5-cyclobutyl-4,4-dimethyl-2-cyclohexen-1-one
(300) 5-cyclopentyl-4,4-dimethyl-2-cyclohexen-1-one
(301) 5-cyclohexyl-4,4-dimethyl-2-cyclohexen-1-one and so on, and those acid addition salts are exemplified.

For example, when substituent R3 and/or R4 are allyl group of aromatic hydrocarbon 1 valence group,
(302) 4,4-dimethyl-5-phenyl-2-cyclohexen-1-one
(303) 4,4-dimethyl-5-naphthyl-2-cyclohexen-1-one and so on, and those acid addition salts are exemplified. Substituent R3 and/or R4 are sometimes alkoxy carbonyl aromatic hydrocarbon 1 valence group and/or allyl group of ester.
(305) 4,4-dimethyl-5-hydroxy methyl-2-cyclohexen-1-one
(306) 4,4-dimethyl-5-hydroxy ethyl-2-cyclohexen-1-one
(307) 4,4-dimethyl-5-hydroxy propyl-2-cyclohexen-1-one and so on, and those acid addition salts are exemplified.

For example, when substituent R3 and/or R4 are amino lower alkyl group,
(308) 5-aminomethyl-4,4-dimethyl-2-cyclohexen-1-one
(309) 5-aminoethyl-4,4-dimethyl-2-cyclohexen-1-one
(310) 5-aminopropyl-4,4-dimethyl-2-cyclohexen-1-one and so on, and those acid addition salts are exemplified.

For example, when substituent R3 and/or R4 are lower alkylamino lower alkyl group,
(311) 4,4-dimethyl-5-methylaminomethyl-2-cyclohexen-1-one
(312) 4,4-dimethyl-5-ethylaminomethyl-2-cyclohexen-1-one
(313) 4,4-dimethyl-5-ethylaminoethyl-2-cyclohexen-1-one and so on, and those acid addition salts are exemplified.

For example, when substituent R3 and/or R4 are di-lower alkylamino lower alkyl group,
(314) 4,4-dimethyl-5-dimethylaminomethyl-2-cyclohexen-1-one
(315) 4,4-dimethyl-5-diethylaminomethyl-2-cyclohexen-1-one and so on, and those acid addition salts are exemplified.

For example, when substituent R3 and/or R4 are cyclic amino groups,
(316) 4,4-dimethyl-5-piperazinyl-2-cyclohexen-1-one
(317) 4,4-dimethyl-5-morpholinyl-2-cyclohexen-1-one and so on, and those acid addition salts are exemplified.

For example, when substituent R3 and/or R4 are cyclic amino lower alkyl group,
- (318) 4,4-dimethyl-5-piperazinyl ethyl-2-cyclohexen-1-one
- (319) 4,4-dimethyl-5-pyrrolinyl methyl-2-cyclohexen-1-one
- (320) 5-azethydinylmethyl-4,4-dimethyl-2-cyclohexen-1-one
- (321) 4,4-dimethyl-5-morpholinylmethyl-2-cyclohexen-1-one and so on, and those acid addition salts are exemplified.

For example, when substituent R3 and/or R4 are acylamino groups of monoacylamin,
- (322) 4,4-dimethyl-5-formylamino-2-cyclohexen-1-one
- (323) 5-acetylamino-4,4-dimethyl-2-cyclohexen-1-one
- (324) 4,4-dimethyl-5-propionylamino-2-cyclohexen-1-one
- (325) 5-butyrylamino-4,4-dimethyl-2-cyclohexen-1-one and so on, and those acid addition salts are exemplified.

For example, when substituent R3 and/or R4 are acyloxy group of ester,
- (326) 4,4-dimethyl-5-formyloxy-2-cyclohexen-1-one.
- (327) 5-acetyloxy-4,4-dimethyl-2-cyclohexen-1-one
- (328) 4,4-dimethyl-5-propionyloxy-2-cyclohexen-1-one
- (329) 5-butyryloxy-4,4-dimethyl-2-cyclohexen-1-one and so on, and those acid addition salts are exemplified.

For example, when substituent R3 and/or R4 are trihalogeno lower alkyl group,
- (330) 4,4-dimethyl-5-trichloromethyl-2-cyclohexen-1-one
- (331) 4,4-dimethyl-5-trifluoromethyl-2-cyclohexen-1-one and so on, and those acid addition salts are exemplified.

For example, when substituent R3 and/or R4 are polycyclic groups,
- (332) 4,4-dimethyl-5-furyl-2-cyclohexen-1-one
- (333) 4,4-dimethyl-5-propyl-2-cyclohexen-1-one
- (334) 4,4-dimethyl-5-thienyl-2-cyclohexen-1-one
- (335) 4,4-dimethyl-5-isoxazolyl-2-cyclohexen-1-one
- (336) 4,4-dimethyl-5-imidazolyl-2-cyclohexen-1-one
- (337) 4,4-dimethyl-5-thiazolyl-2-cyclohexen-1-one
- (338) 4,4-dimethyl-5-pyrrolinyl-2-cyclohexen-1-one
- (339) 5-benzofuryl-4,4-dimethyl-2-cyclohexen-1-one
- (340) 5-benzothiazolyl-4,4-dimethyl-2-cyclohexen-1-one
- (341) 5-pyridyl-4,4-dimethyl-2-cyclohexen-1-one
- (342) 4,4-dimethyl-5-quinolyl-2-cyclohexen-1-one
- (343) 4,4-dimethyl-5-pyrimidinyl-2-cyclohexen-1-one
- (344) 4,4-dimethyl-5-morpholinyl-2-cyclohexen-1-one and so on, and those acid addition salts are exemplified.

For example, when substituent R5 is alkyl group of non-cyclic saturated hydrocarbon,
- (345) 3,4,4-trimethyl-2-cyclohexen-1-one
- (346) 4,4-dimethyl-3-ethyl-2-cyclohexen-1-one
- (347) 4,4-dimethyl-3-propyl-2-cyclohexen-1-one
- (348) 4,4-dimethyl-3-isopropyl-2-cyclohexen-1-one
- (349) 3-butyl-4,4-dimethyl-2-cyclohexen-1-one
- (350) 4,4-dimethyl-3-isobutyl-2-cyclohexen-1-one
- (351) 3-benzyl-4,4-dimethyl-2-cyclohexen-1-one
- (352) 4,4-dimethyl-3-hexyl-2-cyclohexen-1-one
- (353) 4,4-dimethyl-3-octyl-2-cyclohexen-1-one and so on, and those acid addition salts are exemplified.

For example, when substituent R5 is alkoxy group of heterocyclic compound,
- (354) 3-pentyloxy-4,4-dimethyl-2-cyclohexen-1-one
- (355) 4,4-dimethyl-3-hexyloxy-2-cyclohexen-1-one and so on, and those acid addition salts are exemplified. For example, when substituent R5 is a lower alkylamino group of amines,
- (356) 4,4-dimethyl-3-methylamino-2-cyclohexen-1-one
- (357) 4,4-dimethyl-3-ethylamino-2-cyclohexen-1-one
- (358) 4,4-dimethyl-3-propylamino-2-cyclohexen-1-one
- (359) 3-dimethylamino-4,4-dimethyl-2-cyclohexen-1-one and so on, and those acid addition salts are exemplified.

For example, when substituent R5 is alkenyl group of non-cyclic unsaturation hydrocarbon,
- (360) 3-vinyl-4,4-dimethyl-2-cyclohexen-1-one
- (361) 3-allyl-4,4-dimethyl-2-cyclohexen-1-one
- (362) 4,4-dimethyl-3-isopropenyl-2-cyclohexen-1-one and so on, and those acid addition salts are exemplified.

For example, when substituent R5 is cycloalkyl group of monocyclic hydrocarbon,
- (363) 3-cyclopropyl-4,4-dimethyl-2-cyclohexen-1-one
- (364) 3-cyclobutyl-4,4-dimethyl-2-cyclohexen-1-one
- (365) 3-cyclopentyl-4,4-dimethyl-2-cyclohexen-1-one
- (366) 3-cyclohexyl-4,4-dimethyl-2-cyclohexen-1-one and so on, and those acid addition salts are exemplified.

For example, when substituent R5 is allyl group of aromatic hydrocarbon 1 valence group,
- (367) 4,4-dimethyl-3-phenyl-2-cyclohexen-1-one
- (368) 4,4-dimethyl-3-naphthyl-2-cyclohexen-1-one and so on, and those acid addition salts are exemplified. Substituent R5 is alkoxy carbonyl group resulting in ester.

For example, when substituent R5 is hydroxy lower alkyl group,
- (370) 4,4-dimethyl-3-hydroxy methyl-2-cyclohexen-1-one
- (371) 4,4-dimethyl-3-hydroxy ethyl-2-cyclohexen-1-one
- (372) 4,4-dimethyl-3-hydroxy propyl-2-cyclohexen-1-one and so on, and those acid addition salts are exemplified.

For example, when substituent R5 is amino lower alkyl group,
- (373) 3-aminomethyl-4,4-dimethyl-2-cyclohexen-1-one
- (374) 3-aminoethyl-4,4-dimethyl-2-cyclohexen-1-one
- (375) 3-aminopropyl-4,4-dimethyl-2-cyclohexen-1-one and so on, and those acid addition salts are exemplified.

For example, when substituent R5 is a lower alkylamino lower alkyl group,
- (376) 4,4-dimethyl-3-methylaminomethyl-2-cyclohexen-1-one
- (377) 4,4-dimethyl-3-ethylaminomethyl-2-cyclohexen-1-one
- (378) 4,4-dimethyl-3-ethylaminoethyl-2-cyclohexen-1-one and so on, and those acid addition salts are exemplified.

For example, when substituent R5 is a di-lower alkylamino lower alkyl group,
- (379) 3-dimethylaminomethyl-4,4-dimethyl-2-cyclohexen-1-one
- (380) 3-diethylaminomethyl-4,4-dimethyl-2-cyclohexen-1-one and so on, and those acid addition salts are exemplified.

For example, when substituent R5 is cyclic amino group,
- (381) 4,4-dimethyl-3-piperazinyl-2-cyclohexen-1-one
- (382) 4,4-dimethyl-3-morpholinyl-2-cyclohexen-1-one and so on, and those acid addition salts are exemplified.

For example, when substituent R5 is a cyclic amino lower alkyl group,
- (383) 4,4-dimethyl-3-piperazinylethyl-2-cyclohexen-1-one
- (384) 4,4-dimethyl-3-pyrrolinylmethyl-2-cyclohexen-1-one
- (385) 3-azethydinylmethyl-4,4-dimethyl-2-cyclohexen-1-one
- (386) 4,4-dimethyl-3-morpholinylmethyl-2-cyclohexen-1-one and so on, and those acid addition salts are exemplified.

For example, when substituent R5 is acylamino group of monoacylamin,
(387) 4,4-dimethyl-3-formylamino-2-cyclohexen-1-one
(388) 3-acetylamino-4,4-dimethyl-2-cyclohexen-1-one
(389) 4,4-dimethyl-3-propionylamino-2-cyclohexen-1-one
(390) 3-butyrylamino-4,4-dimethyl-2-cyclohexen-1-one and so on, and those acid addition salts are exemplified.

For example, when substituent R5 is acyloxy group of ester,
(391) 4,4-dimethyl-3-formyloxy-2-cyclohexen-1-one
(392) 3-acetyloxy-4,4-dimethyl-2-cyclohexen-1-one
(393) 4,4-dimethyl-3-propionyloxy-2-cyclohexen-1-one
(394) 3-butyryloxy-4,4-dimethyl-2-cyclohexen-1-one and so on, and those acid addition salts are exemplified.

For example, when substituent R5 is a trihalogeno lower alkyl group,
(395) 4,4-dimethyl-3-trichloromethyl-2-cyclohexen-1-one
(396) 4,4-dimethyl-3-trifluoromethyl-2-cyclohexen-1-one and so on, and those acid addition salts are exemplified.

For example, when substituent R5 is polycyclic group,
(397) 4,4-dimethyl-3-furyl-2-cyclohexen-1-one
(398) 4,4-dimethyl-3-propyl-2-cyclohexen-1-one
(399) 4,4-dimethyl-3-thienyl-2-cyclohexen-1-one
(400) 4,4-dimethyl-3-isoxazolyl-2-cyclohexen-1-one
(401) 4,4-dimethyl-3-imidazolyl-2-cyclohexen-1-one
(402) 4,4-dimethyl-3-thiazolyl-2-cyclohexen-1-one
(403) 4,4-dimethyl-3-pyrrolinyl-2-cyclohexen-1-one
(404) 3-benzofuryl-4,4-dimethyl-2-cyclohexen-1-one
(405) 3-benzothiazolyl-4,4-dimethyl-2-cyclohexen-1-one
(406) 3-pyridyl-4,4-dimethyl-2-cyclohexen-1-one
(407) 4,4-dimethyl-3-quinolyl-2-cyclohexen-1-one
(408) 4,4-dimethyl-3-pyrimidinyl-2-cyclohexen-1-one
(409) 4,4-dimethyl-3-morpholinyl-2-cyclohexen-1-one and so on, and those acid addition salts are exemplified.

For example, when substituent R6 is alkyl group of non-cyclic saturated hydrocarbon,
(410) 2,4,4-trimethyl-2-cyclohexen-1-one
(411) 4,4-dimethyl-2-ethyl-2-cyclohexen-1-one
(412) 4,4-dimethyl-2-propyl-2-cyclohexen-1-one
(413) 4,4-dimethyl-2-isopropyl-2-cyclohexen-1-one
(414) 2-butyl-4,4-dimethyl-2-cyclohexen-1-one
(415) 4,4-dimethyl-2-isobutyl-2-cyclohexen-1-one
(416) 2-benzyl-4,4-dimethyl-2-cyclohexen-1-one
(417) 4,4-dimethyl-2-hexyl-2-cyclohexen-1-one
(418) 4,4-dimethyl-2-octyl-2-cyclohexen-1-one and so on, and those acid addition salts are exemplified.

For example, when substituent R6 is alkoxy group of heterocyclic compound,
(419) 2-pentyloxy-4,4-dimethyl-2-cyclohexen-1-one
(420) 4,4-dimethyl-2-hexyloxy-2-cyclohexen-1-one and so on, and those acid addition salts are exemplified. For example, when substituent R6 is a lower alkylamino group of amines,
(421) 4,4-dimethyl-2-methylamino-2-cyclohexen-1-one
(422) 4,4-dimethyl-2-ethylamino-2-cyclohexen-1-one
(423) 4,4-dimethyl-2-propylamino-2-cyclohexen-1-one
(424) 2-dimethylamino-4,4-dimethyl-2-cyclohexen-1-one and so on, and those acid addition salts are exemplified.

For example, when substituent R6 is alkenyl group of non-cyclic saturated hydrocarbon,
(425) 2-vinyl-4,4-dimethyl-2-cyclohexen-1-one
(426) 2-allyl-4,4-dimethyl-2-cyclohexen-1-one
(427) 4,4-dimethyl-2-isopropenyl-2-cyclohexen-1-one and so on, and those acid addition salts are exemplified.

For example, when substituent R6 is cycloalkyl group of single cyclic hydrocarbon,
(428) 2-cyclopropyl-4,4-dimethyl-2-cyclohexen-1-one
(429) 2-cyclobutyl-4,4-dimethyl-2-cyclohexen-1-one
(430) 2-cyclopentyl-4,4-dimethyl-2-cyclohexen-1-one
(431) 2-cyclohexyl-4,4-dimethyl-2-cyclohexen-1-one and so on, and those acid addition salts are exemplified.

For example, when substituent R6 is allyl group of aromatic hydrocarbon 1 valence group,
(432) 4,4-dimethyl-2-phenyl-2-cyclohexen-1-one
(433) 4,4-dimethyl-2-naphthyl-2-cyclohexen-1-one and so on, and those acid addition salts are exemplified. Substituent R6 represents alkoxy carbonyl group and sometimes becomes ester.

For example, when substituent R6 is a hydroxy lower alkyl group,
(435) 4,4-dimethyl-2-hydroxy methyl-2-cyclohexen-1-one
(436) 4,4-dimethyl-2-hydroxy ethyl-2-cyclohexen-1-one
(437) 4,4-dimethyl-2-hydroxy propyl-2-cyclohexen-1-one and so on, and those acid addition salts are exemplified.

For example, when substituent R6 is an amino lower alkyl group,
(438) 2-aminomethyl-4,4-dimethyl-2-cyclohexen-1-one
(439) 2-aminoethyl-4,4-dimethyl-2-cyclohexen-1-one
(440) 2-aminopropyl-4,4-dimethyl-2-cyclohexen-1-one and so on, and those acid addition salts are exemplified.

For example, when substituent R6 is a lower alkylamino lower alkyl group,
(441) 4,4-dimethyl-2-methylaminomethyl-2-cyclohexen-1-one
(442) 4,4-dimethyl-2-ethylaminomethyl-2-cyclohexen-1-one
(443) 4,4-dimethyl-2-ethylaminoethyl-2-cyclohexen-1-one and so on, and those acid addition salts are exemplified.

For example, when substituent R6 is a di-lower alkylamino lower alkyl group,
(444) 2-dimethylaminomethyl-4,4-dimethyl-2-cyclohexen-1-one
(445) 2-diethylaminomethyl-4,4-dimethyl-2-cyclohexen-1-one and so on, and those acid addition salts are exemplified.

For example, when substituent R6 is cyclic amino group,
(446) 4,4-dimethyl-2-piperazinyl-2-cyclohexen-1-one
(447) 4,4-dimethyl-2-morpholinyl-2-cyclohexen-1-one and so on, and those acid addition salts are exemplified.

For example, when substituent R6 is a cyclic amino lower alkyl group,
(448) 4,4-dimethyl-2-piperazinylethyl-2-cyclohexen-1-one
(449) 4,4-dimethyl-2-pyrrolinylmethyl-2-cyclohexen-1-one
(450) 2-azethydinylmethyl-4,4-dimethyl-2-cyclohexen-1-one
(451) 4,4-dimethyl-2-morpholinylmethyl-2-cyclohexen-1-one and so on, and those acid addition salts are exemplified.

For example, when substituent R6 is acylamino group of monoacylamin,
(452) 4,4-dimethyl-2-formylamino-2-cyclohexen-1-one
(453) 2-acetylamino-4,4-dimethyl-2-cyclohexen-1-one
(454) 4,4-dimethyl-2-propionylamino-2-cyclohexen-1-one
(455) 2-butyrylamino-4,4-dimethyl-2-cyclohexen-1-one and so on, and those acid addition salts are exemplified.

For example, when substituent R6 is acyloxy group of ester,
(456) 4,4-dimethyl-2-formyloxy-2-cyclohexen-1-one
(457) 2-acetyloxy-4,4-dimethyl-2-cyclohexen-1-one (458) 4,4-dimethyl-2-propionyloxy-2-cyclohexen-1-one
(459) 2-butyryloxy-4,4-dimethyl-2-cyclohexen-1-one and so on, and those acid addition salts are exemplified.

For example, when substituent R6 is a trihalogeno lower alkyl group,
(460) 4,4-dimethyl-2-trichloromethyl-2-cyclohexen-1-one
(461) 4,4-dimethyl-2-trifluoromethyl-2-cyclohexen-1-one and so on, and those acid addition salts are exemplified.

For example, when substituent R6 is polycyclic group,
(462) 4,4-dimethyl-2-furyl-2-cyclohexen-1-one
(463) 4,4-dimethyl-2-propyl-2-cyclohexen-1-one
(464) 4,4-dimethyl-2-thienyl-2-cyclohexen-1-one
(465) 4,4-dimethyl-2-isoxazolyl-2-cyclohexen-1-one
(466) 4,4-dimethyl-2-imidazolyl-2-cyclohexen-1-one
(467) 4,4-dimethyl-2-thiazolyl-2-cyclohexen-1-one
(468) 4,4-dimethyl-2-pyrrolinyl-2-cyclohexen-1-one
(469) 2-benzofuryl-4,4-dimethyl-2-cyclohexen-1-one
(470) 2-benzothiazolyl-4,4-dimethyl-2-cyclohexen-1-one
(471) 2-pyridyl-4,4-dimethyl-2-cyclohexen-1-one
(472) 4,4-dimethyl-2-quinolyl-2-cyclohexen-1-one
(473) 4,4-dimethyl-2-pyrimidinyl-2-cyclohexen-1-one
(474) 4,4-dimethyl-2-morpholinyl-2-cyclohexen-1-one and so on, and those acid addition salts are exemplified.

For example, when R5 and/or R6 in chemical formula (3-b) are bond substituents of condensation polycyclic hydrocarbon compounds and condensation heterocyclic compounds,
(475) 5H-4-dimethyl-7-oxo-indene
(476) 4-dimethyl-1-oxo-tetralin
(477) 3H-4-dimethyl-1-oxo-anthracene
(478) 5H-4-dimethyl-7-oxo-benzothiophene
(479) 5H-4-dimethyl-7-oxo-benzofuran
(480) 5H-4-dimethyl-7-oxo-indole
(481) 6H-5-dimethyl-8-oxo-quinoline
(482) 6H-5-dimethyl-8-oxo-quinoxaline
(483) 6H-5-dimethyl-8-oxo-cinnoline
(484) 5H-5-dimethyl-8-oxo-1,4-dithianaphthalene
(485) 3H-4-dimethyl-1-oxo-thianthrene, and those acid addition salts are exemplified.

The compounds which is shown in chemical formula (1-a), (1-b), (2), (3-a) and (3-b) of this invention can be synthesized by the known processing manners of organic synthesis with conventional organic chemical compounds and/or natural plant oils. When the acid addition salts or the compounds which is shown in general formula (1-a), (1-b), (2), (3-a) and (3-b) are used as inhibitory or blocking agents of function which is generated by multi-dimensional structure, it is possible to be administered as a single agent or a combined agent with the carrier substances which can be allowable as drugs. However, it needs to be not restricted in the manner which is demonstrated in this invention. These compositions are dependent on routes and/or planning of administration.

When the acid addition salts or the compounds which is shown in general formula (1-a), (1-b), (2), (3-a) and (3-b) are used as drug above-mentioned, those can be administered orally or non-orally as medicament compositions such as powders, granules, tablets, capsules, injection solutions by suitably mixing with adequate components such as carrier substances, excipients or attenuants which are allowable pharmaceutically. Also, an effect of the compounds can be expected by manner of vapor.

When the compound which is shown in chemical formula (1-a), (1-b), (2), (3-a) and (3-b) of this invention is used by oral route, several types of tablets, capsules, powder materials, granular agents and liquid agents are available. When the compound is administered through the non-oral route, those are used in the form of disinfected fluid. When the compounds are used as types above-mentioned, the carrier substances with nontoxic solids or fluids include in a composition.

As an example of solid carriers, capsules made by usual gelatin is used. Moreover, effective ingredients are utilized with subsidiary substances or by tabulating, granulating and/or powder packaging without subsidiary substances. The following substances are used as the excipients; gelatin, lactose, sugars such as glucose, cone, wheat, rice, starches such as corn starch, fatty acids such as stearic acid, fat bases such as calcium stearic acid and magnesium stearic acid, talc, vegetable oil, alcohol such as stearylalcohol and benzyl alcohol, gum, polyethylene alkylene glycol and so on.

These capsule, tablet, granule and powder are generally 0.1-80 weight % and contains effective ingredient of 0.1-60 weight %. Liquid carriers such as water, physiological saline, sugar solution, dextrose solution, ethylene glycol, propylene glycol, glycols such as polyethylene glycol, polyoxyethylene sorbitan monoolate are desirable.

When it is administered non-orally by the manner of intramuscular injection, intravenous injection or hypodermic injection, the compounds provided in general formula (1-a), (1-b), (2), (3-a) and (3-b) are used as the germ-free solution which is added other solutes such as minerals or glucose in order to make the isotonic solution. Appropriate solvents for an injection represent sterilizing water, solution of lidocaine hydrochloride (for intramuscular injection), physiological saline, glucose solution, any kind of fluids for an intravenous injection, electrolyte solution (for intravenous injection) and so on. When those solutions for the injection are used, usual dosage is 0.01-20 weight % and is desirable at 0.05-5 weight %.

In the case of liquids for oral administration, it is better to be used as suspension or syrup with 0.01-20 weight %. A carrier of these liquids is watery excipient such as perfume, syrup and micelle which are available for pharmaceutic manufacturing.

When the compounds in this invention are drug-manufactured by combination with the carriers which is allowable on pharmaceutics, usually known methods and techniques are avairable. Concretely, when ointment, cream agents, emulsions or milky lotions are produced, silver-carried inorganic compounds, drugs and halogen compounds as occasion demands are added at melting and mixing, simultaneously, during and after emulsification resulting in ointments, cream agents or milky lotions. Also, drugs and/or halogen compounds can be added firstly. When the compounds in this invention are used as sterilizing agents and disinfectants for living space, an effect can be obtained by single use or combination with suitable carriers. Concretely, it makes operate directly or indirectly through a room air to solid surface by aspersion, embrocation or evaporation.

Also, a sterilizing effect can be obtained by adding the compounds into water of humidifier and on any part of circulation circuits of air-conditioning device. In addition, when the compounds in this invention composition are used as depolymerization agents, improving agents for surface active substances, reductants, free radical scavengers, desulfurization agents, phase transition agents, improving agents of phase transition, improving agents of microphase separation structure, promoting agents for plasticity and/or elasticity, improving agent for plasticity and/or elasticity, copolymerization agents, copolymerization improving agents, polymerization regulators, improving agents for polymerization adjustment, stabilizers, antioxidants, improving agents for crystallized materials and/or amorphous materials, flexibility promoters and/or improving agents for changing in flexibility, those compounds can effectively control, inhibit and/or generate an objective property of substances by using as a single substance and/or a combination with adequate carriers. When the compounds in this invention are used as modulators or improving agents for fluorescent wavelength and excitation wavelength of pigmentums, coating materials, cosmetic pigments or colorants, improving agents of physical property with low molecule substance, improving agents of function with low molecule substance, improving agents of physical property of macromolecules substance, improving agents of function with macromolecules substance and/or improving agents of physical property with macromolecules composite materials and functional macromolecules composite materials, those compounds can effectively control, inhibit and/or generate an objective property with substances by using as a single substance and/or a combination with adequate carriers. Concretely, an improvement of efficiencies can be planned by selecting a mixing ratio with macromolecules substances, a churning temperature, an adjusting energy quantity such as protons and radio waves and/or transition metals.

BEST MODE FOR CARRYING OUT THE INVENTION

Figure 1:
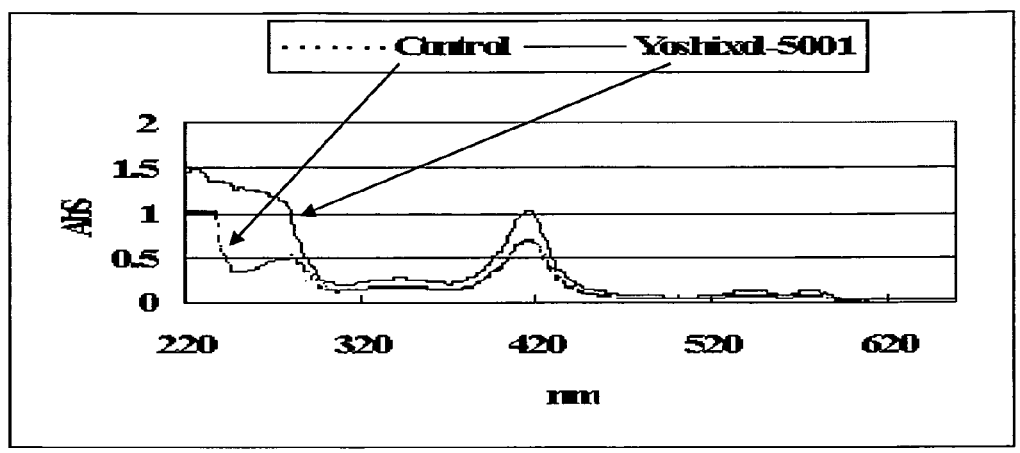
FIG. 1 is a graph which represents the effect of Yoshixol, which is a representative compound of inhibitory or blocking agents of molecular generating and/or inducing functions in this invention, on NADPH, NADP, heme and cytochrome C which were measured by a infrared spectrophotometer.
Figure 2:
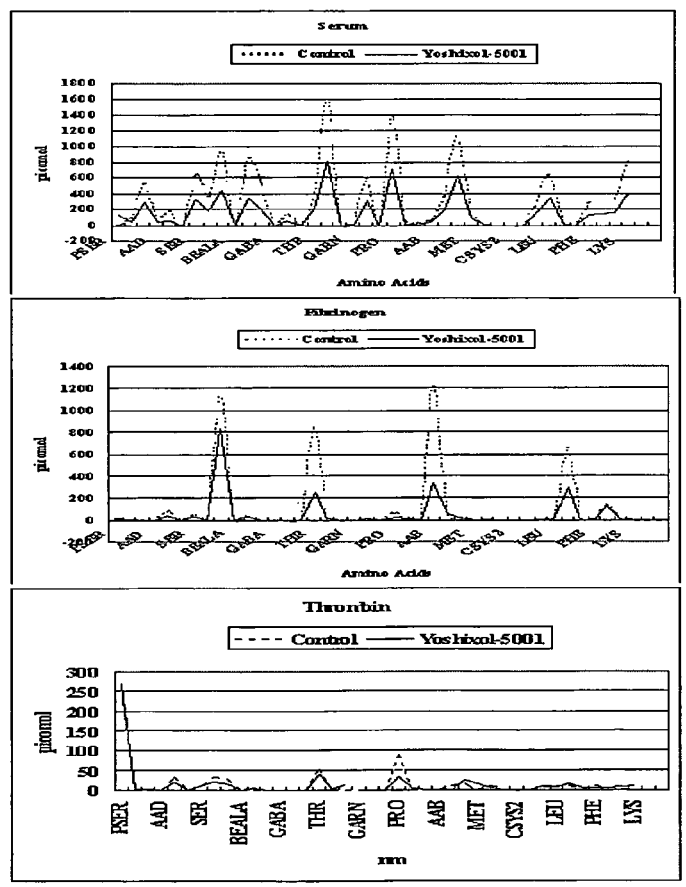
FIG. 2 is the graph which shows the effect of Yoshixol on amino acids composition of human blood serum, thrombin and fibrinogen.

The chemical compound which is used and enforced in this invention is not especially limited. But, as one of a concrete and representative compound which shows reasonable biological effect and which is easily synthesized chemically because of the simple chemical structure, it was synthesized 4,4-dimethyl-6-methylene-2-cyclohexen-1-one (this compound is termed as Yoshixol) which is the compound that all of substituent R3, R4, R5 and R6 shown in chemical formula (3-a) are hydrogen atoms. And, unless otherwise specified, representative experiments are demonstrated using this Yoshixol so as to show the effectiveness of the present invention. Chemical formula of this compound is the following.

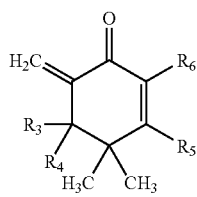

Yoshixol was synthesized according to the following processes. But, a synthesizing process of this compound is not restricted by the synthesizing process which was demonstrated here.

To a solution of diisopropylamine (7.27 g, 7 mmol) in anhydrous tetrahydrofuran (THF) was added drop wise a hexane solution (1.62 mol/l) of n-butyllithium (44.4 ml, 70 mmol) at −78° C. The solution was warmed to 0° C. and stirred for 1 hr at this temperature. After thus prepared lithium diisopropylamide solution was again cooled to −78° C., 4,4-dimethyl-2-cyclohexen-1-one (7.5 g, 60 mmol) was added dropwise and stirring was continued for 1 hr. Then, gaseous formaldehyde, generated by a thermal decomposition of paraformaldehyde (5 g) over an oil bath, was blown through the solution with a gentle stream of dry nitrogen gas and the reaction mixture was stirred for 2 hr. After standing over night at room temperature, 1N hydrochloric acid was added until the solution became weak acid. The solvent was removed and the residue was extracted with ether. After drying over anhydrous sodium sulfate and removal of the solvent, a mixture of 4,4-dimethyl-6-methylene-2-cyclohexen-1-one and 4,4-dimethyl-6-hydroxymethyl-2-cyclohexen-1-one was obtained (7.03 g). This mixture (3.0 g) was treated in reflxing benzene for 2 hr in the presence of catalytic amount of anhydrous p-toluenegulfonic acid and molecular sieve 3A (4 g). The solution was neutralized with 1N sodium bicarbonate and washed with brine. After drying over anhydrous sodium sulfate and removal of the solvent, crude 4,4-dimethyl-6-methylene-2-cyclohexen-1-one (Yoshixol) was obtained (2.35 g, overall yield 68%). The analytical sample was available. 2-cyclohexen-1-one was obtained (2.35 g, overall yield 68%). The analytical sample was available after purification by column chromatography or kugelrohr distillation but yield was much lowered. This NMR analysis of Yoshixol is following: IR(neat): 1670(C=O), 1620(C=C) cm-1. 1H NMR (60 MHZ, CCL4), d1.15 (s, 6H, C(CH3)2), 2.57 (bs, 2H, CH2), 5.20, 5.93 (2m, 2H, CH2=), 5.87 (d, J=10, 1H, 2-H), 6.63 (d, J=10 Hz, 3-H).

<Stability of Solution Under Light>

Changes in coloring, viscosity and odor of Yoshixol into a sealed glass tube, which have been stocked under the room light, were observed at 6 months after the synthesis. As a result, those of fragrance, coloring and viscosity did not change and were identical to the initial property.

Though an effective dose of Yoshixol, the derivatives and those acid addition salts is blended, the adequate dosage differs dependently on body weights, administration routes, symptoms, individual patient or ages and so on.

For example, when it is administered orally in adult patient, dosage of 0.01-5 mg/Kg weight per day, namely 0.1-2 mg/Kg of body weights per day, is acceptable and is divided into one or several times a day.

And, when it is administered intravenously, dosage of 0.01-500 mg/Kg body weight per day, namely 5-100 mg/Kg body weight per days is acceptable and is divided into one or several times a day. Moreover, when an objective to use in the life space so on is for a sterilizing and/or bactericidal action, a range of concentration between 0.5 and 100 picomole is desirable.

Though the following presentations by using Yoshixol are demonstrated sequentially effectiveness of inhibitory or blocking agents of the function induced or generated by multi-dimensional structure which is major points of this invention, Yoshixol is picked up as a concrete and representative compound in order to most simply provide effectiveness and basic mechanism. And also, the preparations and methods of experiments which can most simply discuss the mechanism and were most close historically toward the method of the original idea that has been promoted to specialization in scientific world were chosen in the invention. Therefore, the inhibitory or blocking agents of molecular generating and/or inducing functions which are provided in claims 1-6 of this invention are not restricted any more by experimental methods and regents demonstrated here. And, because this invention consists of plans which are able to provide and discuss above-mentioned biological effects from a respect with physical property of substances, this invention provides effectiveness on low molecule substances and macromolecules substances of non-living organism as shown in representative examples.

Though the following presentations by using Yoshixol are demonstrated sequentially effectiveness of controlling, inhibitory and/or blocking agents of the function induced or generated by multi-dimensional structure of low molecular substances and/or macromolecular substances in this invention, Yoshixol is picked up as a concrete and representative compound in order to most simply provide effectiveness and basic mechanism, identically in the case of biological effects.

And also, the preparations and methods of experiments which can most simply confirm the mechanism were chosen in the invention. Therefore, the inhibitory or blocking agents of molecular generating and/or inducing functions which are provided in claims 1-11 of this invention are not restricted any more by experimental methods, regents and analysis demonstrated here.

<Concerning to Reactions with ribose, Glycerin, Cellulose and Polyethylene Vinyl>

Each 1 ml of glycerin, cellulose, polyethylene vinyl and ribose (1 mol) was mixed respectively with 4 µl of Yoshixol in the test tube and was blended. Then, a fluidability and transparence of the reacted substance in each sample tube were investigated at room temperature (28° C.), heating (80° C.) or cooling (4° C.) state. At room temperature, transparence and softness of each sample in test tube increased. When each sample was cooled, increases in hardness and cloudy occurred. In contrast, at high temperature, increases in fluidability and transparence of each sample occurred to be enhanced greater than above two conditions. This result shows that Yoshixol has polymerization and/or depolymerization effect.

<Effect on NADPH, heme and Cytochrome C>

Changes in concentration of NADPH (340 nanometer), cytochrome C (415, 520, 550 nanometer), heme (415 nanometer) and aromatic amino acids (280 nanometer) in 1 µl of defibrinized human blood serum were measured before and after treatment with 4 µl of Yoshixol by an infrared spectrophotometer. Subsequently, although concentration of NADPH, cytochrome C and heme did not alter even after treatment with Yoshixol, characteristic peak of wave length with amino acids was disappeared and shifted to lower wave length (range of aromatic amines). The result shows that Yoshixol has an effect of producing new aromatic amines not only due to dehydrogenation but due to reduction and/or hydrogen binding. FIG. 1 shows that extremely high and monophasic peak of wave length occurred resulting from disappearance of biphasic peak increased at 280 nanometer.

<Effect on Composition of Amino Acids in Human Blood Serum, Fibrinogen and Thrombin>

Changes in composition of amino acids were analyzed by use of 1 ml of human blood serum, 1 ml of human fibrinogen (concentration of 160 mg/dl), 1 ml of human thrombin before and after treatment with Yoshixol (4 µl). The total amino acids in the human blood serum which was treated with Yoshixol decreased by 41%. And, ratio of each composition was altered after the treatment so that as an example the concentration of phosphoserine increased about 20 times which level was from 7.2 picomole to 164.8 picomole. Moreover, though concentration of the total amino acids in fibrinogen did not change by treatment with Yoshixol, glutamic acid and hydroxyl serine which were existed before treatment were disappeared after the treatment and, concentration of cystathione in fibrinogen increased to level of more than 5 times. In addition, in thrombin sample which was treated with Yoshixol, glutamic acid, taurine, methionine and aminoisobutylic acid which did not exist before the treatment were produced newly. This result shows that Yoshixol has an effect of a cross-linking coupling such as desulfurization reaction and has an effect which can change from proteins and molecule of amino acids to other molecular configurations of amino acids.

<Effect on Human Blood Coagulation and Fibrin Formation>

Figure 3:
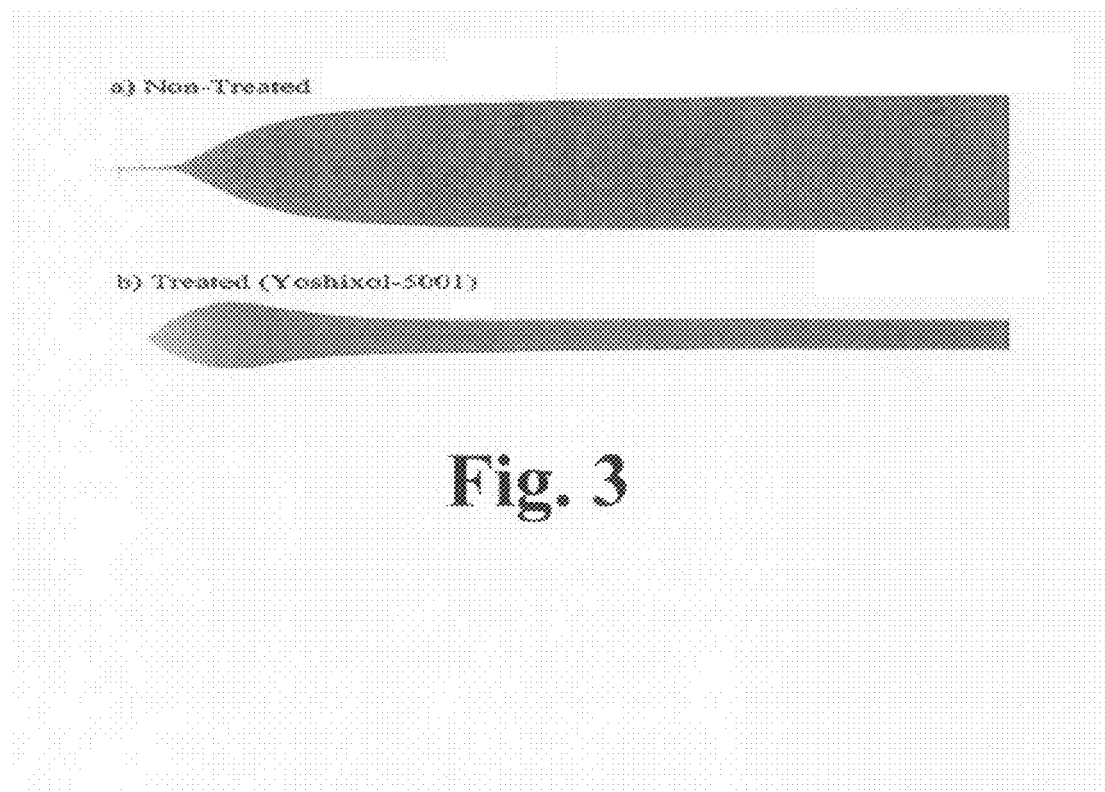
FIGS. 3(a) and 3(b) is the graphs which show the effect of Yoshixol on blood coagulation measured by thromboelastgram.

Effect of Yoshixol (4 µl) on human blood coagulation and fibrin formation (thrombin was added to fibrinogen) were investigated by thromboelastgram (Hellige GMBH, West Germany). Also, a magnitude of fibrin network which is formed at human blood coagulation was investigated by a scanning electron microscopy. Coagulation of human blood without treatment with Yoshixol was started within 1-2 min so that maximum level of coagulation occurred approximately within 15 min, followed by gradual decrease due to activation of fibrinolytic system. Immediately after thrombin is added on fibrinogen, viscosity of the sample started to increase, reached to a maximum level within 5-6 minutes. This maximum level was maintained for periods of 6 hours which was observed (referred FIG. 3a). However, when Yoshixol (4 µl) was added in 0.4 ml of whole blood or fibrinogen (160 mg/dl), onset time of blood coagulation and fibrin formation was delayed to 4-5 minutes and maximum aggregation time was occurred within 6-8 minutes. Maximum level of coagulation after the treatment was inhibited by 90% of control which level was maintained over 6 hours of investigation (referred FIG. 3b). And, when thrombin treated with Yoshixol was added in fibrinogen, any of aggregation reaction was not be found on thromboelastgram. Moreover, in morphological investigations of blood coagulation, rouleaux formation of erythrocyte and formation of fibrin net occurred markedly in the non-treated group with Yoshixol, however, those formations in treated group with Yoshixol did not occur. The result shows that Yoshixol has a strong anticoagulant effect (antithrombin effect) and antifibrinolytic effects.

<Effects on Change in Function of Trypsin and Thrombin and on its Configuration Change>

Figure 4:
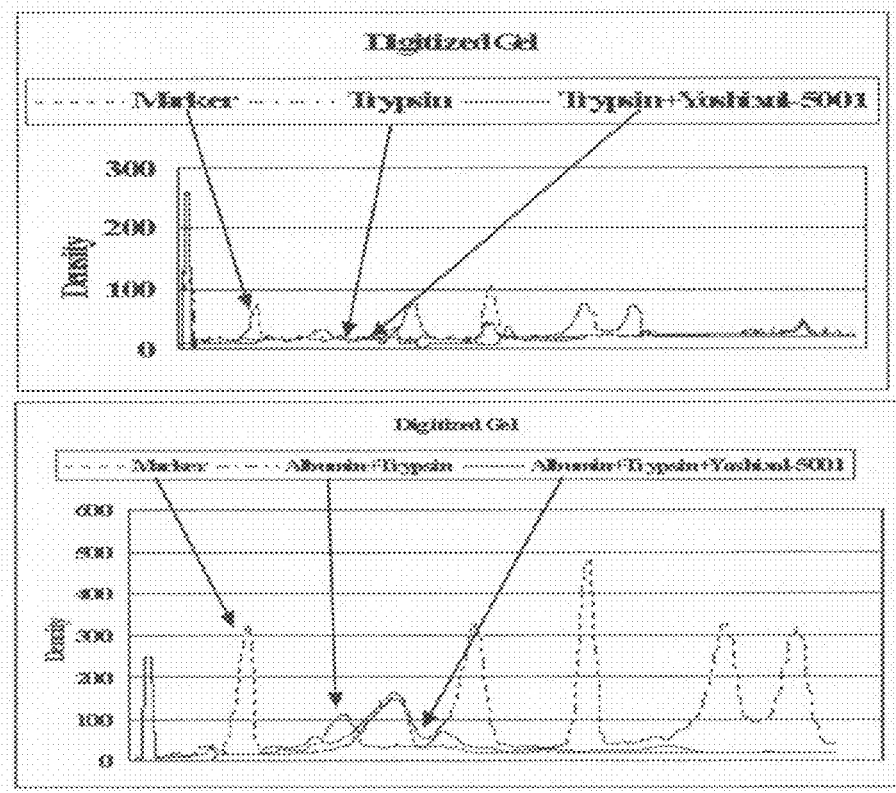
FIG. 4 is the graph which was converted the digitalized data to a graphic design from stained contrast of electrophoresis which was confirmed the effect of Yoshixol on configuration and function of proteins of trypsin and bovine albumin.

Each physiological effect of trypsin (Wakou Jyunyaku Ltd.) and thrombin (Behlinger Manheim-Yamanouchi Co.) was investigated by electrophoresis. When trypsin was added to bovine albumin (Sigma Co. Saint Louis, Mo., USA) or myoglobin (Sigma Co. Saint Louis, Mo., USA), each primary structure of proteins which consist of albumin was altered by proteolytic action of trypsin. In addition, when thrombin was added to human fibrinogen (Behlinger Manheim-Yamanouchi Co.), a primary structure of proteins which consists of fibrinogen was not found. Moreover, primary structure of proteins which consist of trypsin or fibrinogen did not show any electrophoretic changes even after treatment with Yoshixol (4 µl) and, physiological function of trypsin or fibrinogen to bovine albumin, myoglobin and fibrinogen did not occur (referred FIG. 4). This result shows that Yoshixol can block specificity of function which each trypsin or thrombin has because of changing multi-dimensional structure, but not of changing primary structure of trypsin or thrombin.

<Effect on Function of Serum Antibodies for ABO Blood Types>

Figure 5:
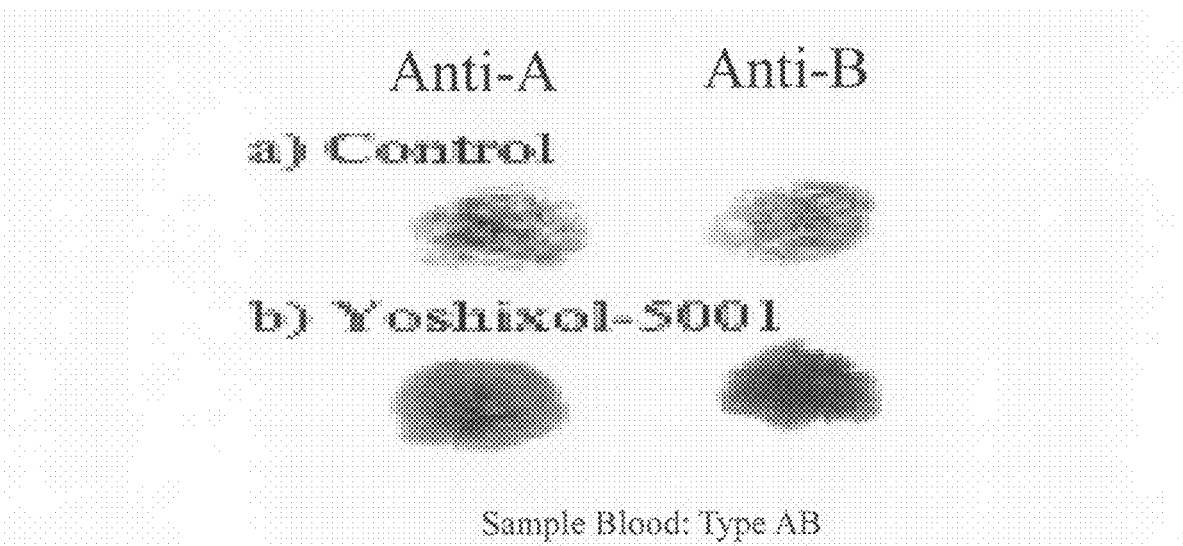
FIG. 5 are graphs which show the effect of Yoshixol on serum antibodies for blood type judgment of ABO blood types, and which were converted from the digitalized data to a graphic design from a magnitude of aggregated reaction.

It is also known that antibody has a structure of Y shape which consists of 2 pairs of light chain and heavy chain in generally, and that the fundamental structure is maintained by S—S bond. Serum antibody reaction of ABO blood types is important historically to understand various kinds of antigen-antibody reactions. In this invention, effect of Yoshixol (4 µl) on the standard judgment of ABO blood types was investigated by using human blood of A type, B type and O type (400 µl, respectively). When each antiserum of blood types was not treated with Yoshixol, antiserum could judge blood type ordinally, resulting from that anti-A blood serum caused a blood aggregation when it was added to human blood of A type, anti-B blood serum caused a blood aggregation when it was added to human blood of B type and both of anti serums did not cause blood aggregation when it was added to human blood of O type. But, when a judgment of ABO type blood type was done by using each antiserum treated with Yoshixol (4 µl), any aggregation did not occur in sample blood with each blood type, and normal judgment of ABO blood type was impossible (referred FIG. 5). Moreover, when a primary structure of antiserums for ABO blood types was investigated by an electrophoretic analysis, any change in primary structure of antiserums did not find even after treatment of Yoshixol. Thus, the results show that Yoshixol can inhibit or block an antibody function which is induced or generated by multi-dimensional structure more than primary structure of antibody.

<Effect on Physiological Function of Vasopressin and Insulin as Peptides>

Figure 6:
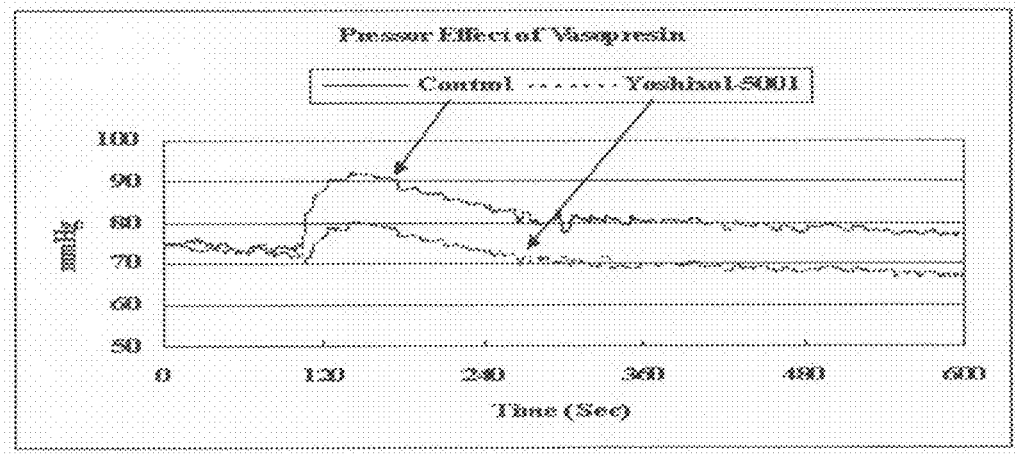
FIG. 6 is the graph which shows an effect of Yoshixol on increases in blood pressure due to vasopressin.

Each vasopressin and insulin has a physiological effect such as a rise of blood pressure and a fall of sugar level in blood respectively. An effect of Yoshixol on these physiological functions was investigated and compared by injection of each hormone without or with treatment with Yoshixol in rabbit in vivo. When vasopressin (100 ng/Kg, Sigma Co. Saint Louis, Mo., USA) without treatment with Yoshixol was injected intravenously, blood pressure increased by 15-25 mmHg so that this increased level was maintained for about 25 minutes. But, vasopressin (100 ng/Kg) treated with Yoshixol (4 µl) caused a increase in blood pressure of only about 5 mmHg (referred FIG. 6). Moreover, a maximal fall of blood sugar level due to injection of insulin (5 units/Kg, Novo Ltd.) without treatment with Yoshixol was 45 mg/dl. When insulin treated with Yoshixol (4 µl) was injected, change in blood sugar level was only 12 mg/dl. The results show that Yoshixol can inhibit or block physiological effect on bioactive peptides with low molecule and hormones which have functional specificity consisted and generated by amino acid sequences.

<Effect on Primary Structure of Proteins>

Figure 7:
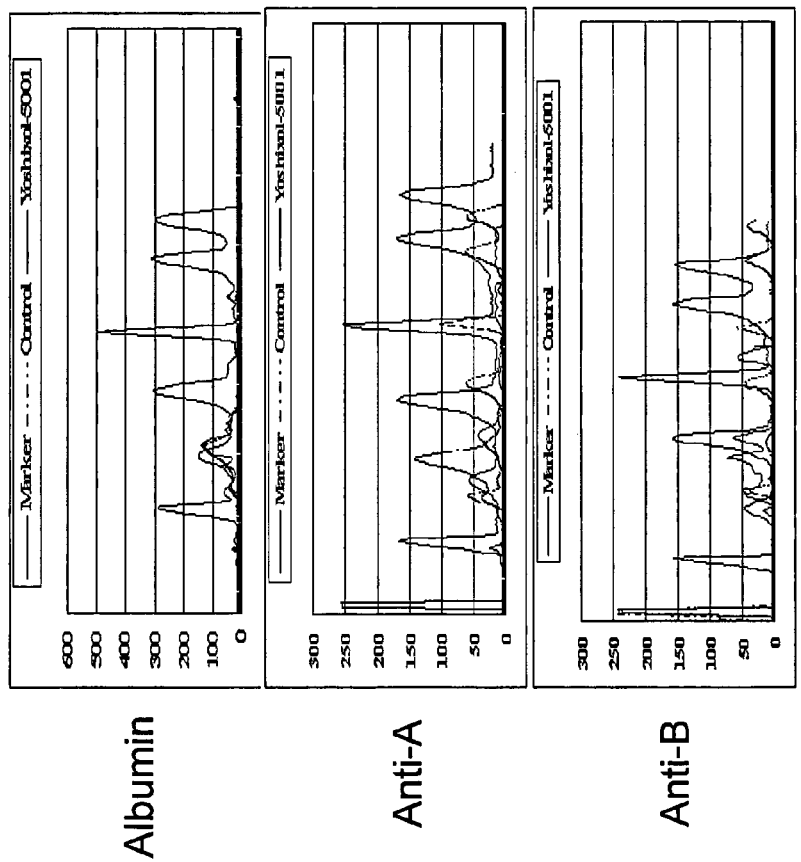
FIGS. 7(a), 7(b) and 7(c) are the graph which was converted the digitalized data to a graphic design from stained contrast of electrophoresis which was confirmed the effect of Yoshixol on configuration of proteins of bovine albumin and blood type anti-A blood serum, anti-B blood serum.

Changes in molecular weight composition of the following macromolecular proteins (1 mole solution) before and after treatment with Yoshixol (4 µl) were investigated after heated denaturation by electrophoretic analysis of non-SDS wide page. The used macromolecules proteins solutions of 1 ml are human defibrinized serum, bovine albumin, human fibrinogen, myoglobin, anti-A blood type serum and anti-B blood type serum (Green Cross Co.). Even after treatment with Yoshixol, distribution of molecular weights on electrophoretic analysis was identical to that of the macromolecules proteins which is not treated (referred FIG. 7). This result shows that Yoshixol does not directly change a primary structure of a biological proteins with macromolecules because of an identical pattern of electrophoretic analysis of each non-treated sample with Yoshixol.

<Concerning about Anti-microbacterial Effects>

Figure 8:
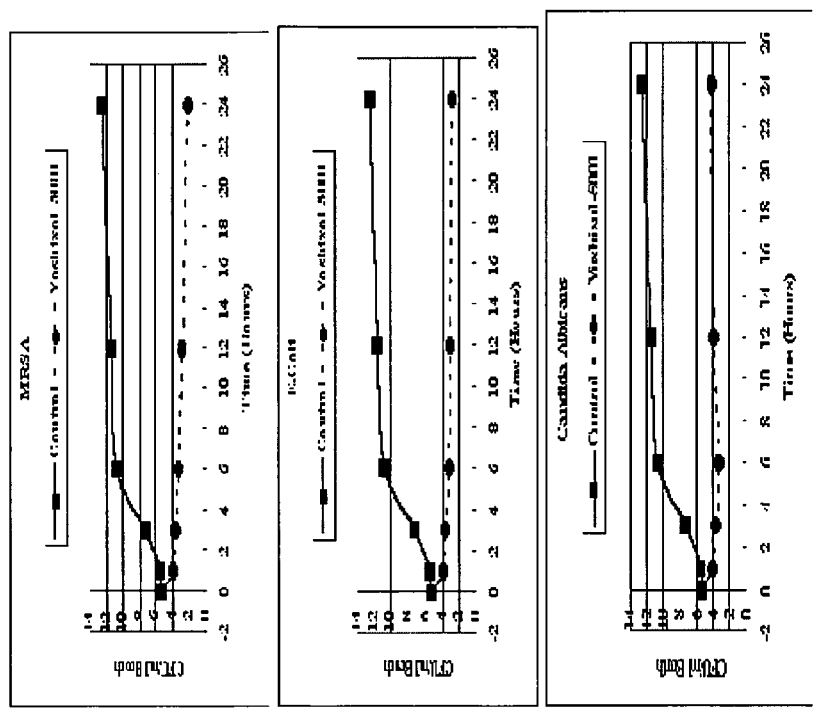
FIGS. 8(a), 8(b) and 8(c) are the graph which shows the antimicrobacterial effect of Yoshixol on methitilin resistance *staphylococcus aureus* (MRSA), *E. Coli* or *Candida albicans*.

(Effect on Methitilin Resistance *Staphylococcus aureus*, MRSA) Effect of Yoshixol on MRSA was investigated by using the original strain (stock no. SCK18) which was isolated from sepsis patient and which was confirmed to cause severe circulatory shock in experimental animals such as mouse, rat, rabbit and dog. Culture medium was used a brain-heart infusion agar. Using dosage of Yoshixol between 0.25 µl and 10 µl per 1 ml of culture medium, colony formation unit (CFU) was measured after 24-hour incubation at 37° C. and the initial CFU was $10^8$. CFU in non-treated group with Yoshixol as control group increased to $10^{10}$ during 24-hour cultured, however, CFU in treated group with Yoshixol (0.25 µl per 1 ml of culture medium) decreased to $10^4$. Additionally, at dosages of 2 µl and 10 µl of Yoshixol per 1 ml of culture medium CFU were $10^2$ and zero respectively (referred FIG. 8a). The result show that Yoshixol has a strong bactericidal effect on MRSA which has been acquired resistance to other antibiotics in gram positive bacteria.

(Effect on *E. Coli*) Effect of Yoshixol was investigated by using *E. Coli* (*E. coli* strain no. W3110) and brain-heart infusion agar as culture medium. Using dosage of Yoshixol 2 µl per 1 ml of culture medium), colony formation unit (CFU) was measured after 24-hour incubation at 37° C. and the initial CFU was $10^8$. CFU in non-treated group with Yoshixol as control group increased to $10^{10}$ during 24-hour cultured, however, CFU in treated group with Yoshixol (2 µl per 1 ml of culture medium) decreased to zero after 1 hour cultured, and was still zero after 24 hours (referred FIG. 8b). The result show that Yoshixol has an extremely strong bactericidal effect on *E. coli* which is gram negative bacteria.

(Effect on acid-fast bacteria) Effect of Yoshixol was investigated by using atypical mycobacteria (Mycobacterium Rapid Grower) and judged the effect by measuring a size of inhibition zone of proliferation on brain-heart infusion agar. The formation of inhibition zone of proliferation occurred at 0.2 µl of Yoshixol per 1 ml of the culture medium and revealed 22 mm of the diameter at 2 µl. The result shows that Yoshixol has a strong bactericidal effect on atypical mycobacteria.

(Concerning about antifungal effect) In order to investigate effect of Yoshixol (2 µl per 1 ml of culture medium on *Candida albicans*, it was investigated by using *Candida Albicans* ($10^6$ CFU/ml) and Sabouraud broth (5 ml). In non-treated group with Yoshixol, CFU did not change after 3 hours incubated, and tended to increase. However, in treated group with Yoshixol, CFU became zero after 1 hour. This level of zero was maintained even after 3 hours incubated. This result show that Yoshixol has an strong antifungal effect.

Figure 9:
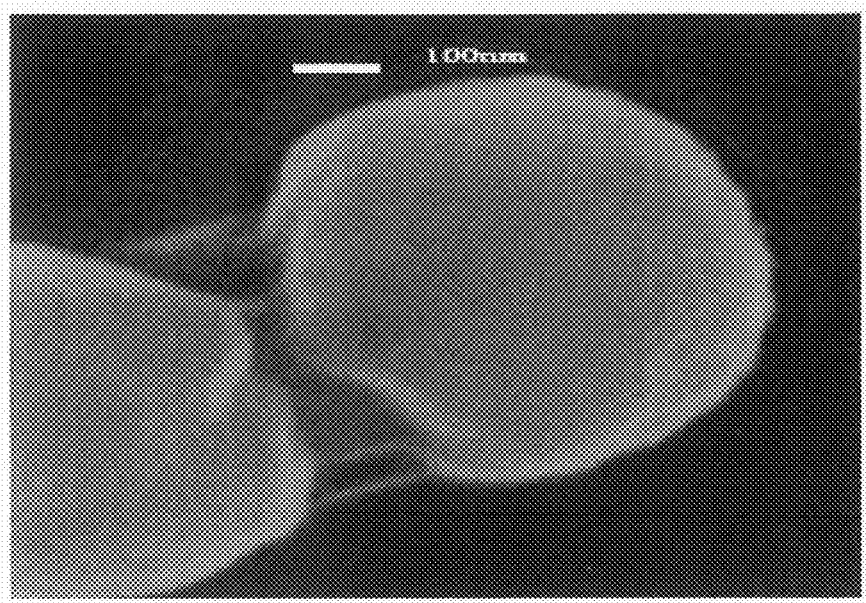
FIG. 9 is a picture of a scanning electron microscopy, which demonstrates a typical morphological aspect of the cell death of MRSA immediately after treatment with Yoshixol.
Figure 10:
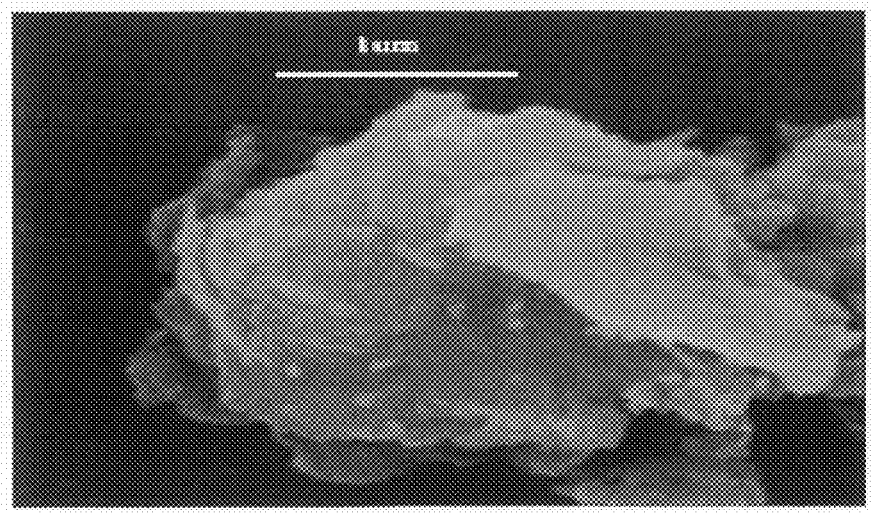
FIG. 10 is a picture of an scanning electron microscopy, which demonstrates a typical morphological aspect of the cell death of *E. coli* immediately after treatment with Yoshixol.
Figure 11:
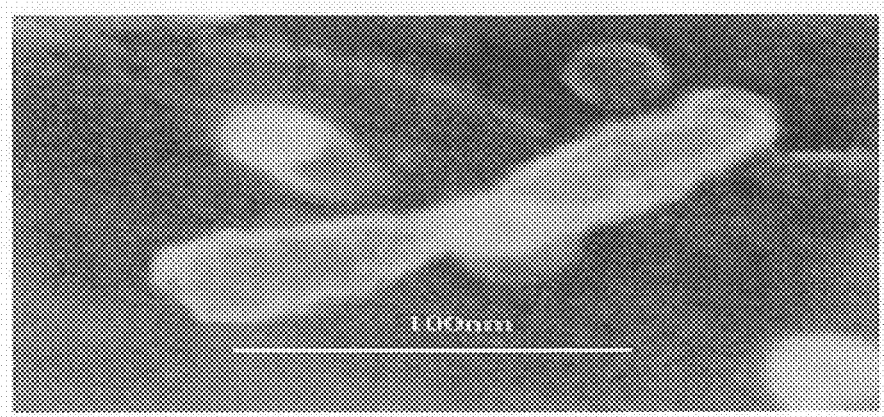
FIG. 11 is a picture of an scanning electron microscopy, which demonstrates a typical morphological aspect of the cell death of acid-fast bacilli immediately after treatment with Yoshixol.
Figure 12:
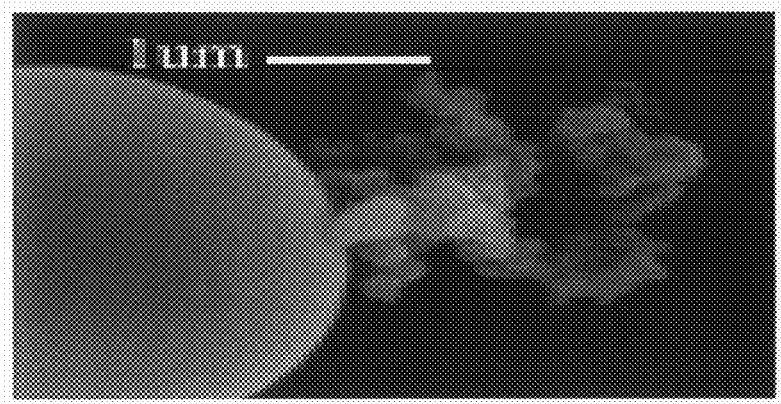
FIG. 12 is a picture of an scanning electron microscopy, which demonstrates a typical morphological aspect of the cell death of *Candida albicans* immediately after treatment with Yoshixol.
Figure 13:
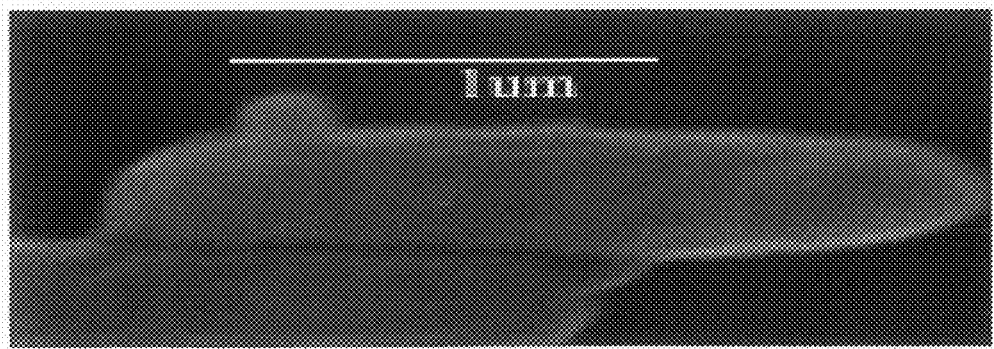
FIG. 13 is a picture of an scanning electron microscopy, which demonstrates a typical morphological aspect of the cell death of *pseudomonas aeruginosa* immediately after treatment with Yoshixol.

Those antibacterial effects provide interests related to histological aspect of cell death. Thus, in MRSA, investigation by a scanning electron microscopy showed characteristic histological images after Yoshixol that grouped MRSA bacilli was separated to an individual bacterial cell, and that small particles with a size of 10-50 nm were sprayed out with an explosive aspect from surface structure of the individual cell (FIG. 9) and, that as at the final stage of cell death the smaller particles than the above were dispersed like fireworks with concentric circle. Such characteristic aspects were also observed by a transmission electron microscopic image. Scanning electron-microscopic observation of *E. Coli* showed that the surface of *E. coli* were loosed the smoothness and were consisted of small particles about 10-50 nm and, that some expanded prominences were appeared on the surface (referred FIG. 10). In the case of *E. coli*, of course, an adhesive group of bacilli lost and the products at the final stage were destroyed resulting in small particles. Even in cases of acid-fast bacteria (referred FIG. 11) and *Candida albicans* (referred FIG. 12) after treatment with Yoshixol, similar histological aspects were observed. Moreover, histological observation of *pseudomonas aeruginosa* after treatment with Yoshixol showed that the bacilli were swelled as likely as a balloon and were ruptured so that components of the bacilli became into small particles (referred FIG. 13). These results show that though Yoshixol has a disinfective and antimicrobacterial effect, mechanism for cell death differs from the antibacterial and bactericidal mechanism with conventional drugs such as denaturation, necrosis and/or coagulation. The characteristic mechanism related to effect of Yoshixol on microbacteria is to inhibit an adhesion between individual bacteria and to produce small particles by destroying the components of bacilli, with an aspect of erupting, explosing and/or ballooning according to molecular composition which is contributed to each morphogeneis of bacilli. These histological findings are identical with zeiosis or apoptosis which has been pointed out. Thus, this indicated point shows that it is possible to apply Yoshixol as effective antibacterial and/or bactericidal agents which do not induce a variability and drug resistance.

<Concerning to Disinfection Sterilizing Effect>

In order to investigate antimicrobacterial effect of evaporating component of Yoshixol, antimicrobacterial effect of Yoshixol in this invention, which concentration is 50 µl in the whole space of the schale, was studied by culturing the bacilli of methitiline resistance *staphylococcus aureus, E. Coli, Candida albicans* and acid-fast bacteria which were same strains mentioned above in the ordinary gelatin agar and BHI (brain heart infusion) culture medium, heart infusion culture medium and Sabouraud culture medium. It was done to investigate prolifelation of each bacteria during 24 hours incubation by avoiding to contact with culture medium which was disseminated each bacteria and a piece of filter paper which was dipped in adequate amount of Yoshixol. For it, the position of culture medium was upside and sample paper was put on the base of the schale. Subsequently, proliferation of each bacteria mentioned above did not occur even at indirect contact due to evaporating component of Yoshixol from the base of the schale in a constant-temperature state of 37° C., but not due to a direct contact diffusion. This result shows that volatilizating and/or evaporating component of Yoshixol in this invention comfirmatively has a strong effect as bactericidal and/or sterilized agent even when it is used via room air in the living space.

<Concerning Effect on Production of Nitric Oxide>

Recent interest has been focused recently in effects of nitric oxide (NO) which is generated in body. Such effects are anticancer effect, bactericidal effect, inhibitory effect of antigen-antibody reaction and cardiovascular effect. Involvement of NO in the effects of Yoshixol which was demonstrated above, such as effect on blood aggregation, effect on fibrin formation and antibacterial effect on MRSA, was investigated by using NG-methyl-L-arginine (NMLA) as blocking agent of generating NO. When 4 µl of NMLA (1 mol) was added in the each test sample with and without Yoshixol, blood aggregation effect, effect of fibrin formation and bactericidal effect of Yoshixol were decreased by 10-20% comparing to effect of Yoshixol alone. This result shows that Yoshixol is a NO producing agent in vivo and that the produced NO by Yoshixol contributes to about 10-20% of anticancer effect, bactericidal effect, anti-viral effect and effect on antigen-antibody reaction of Yoshixol.

<Effect on Bacteriophage>

Figure 14:
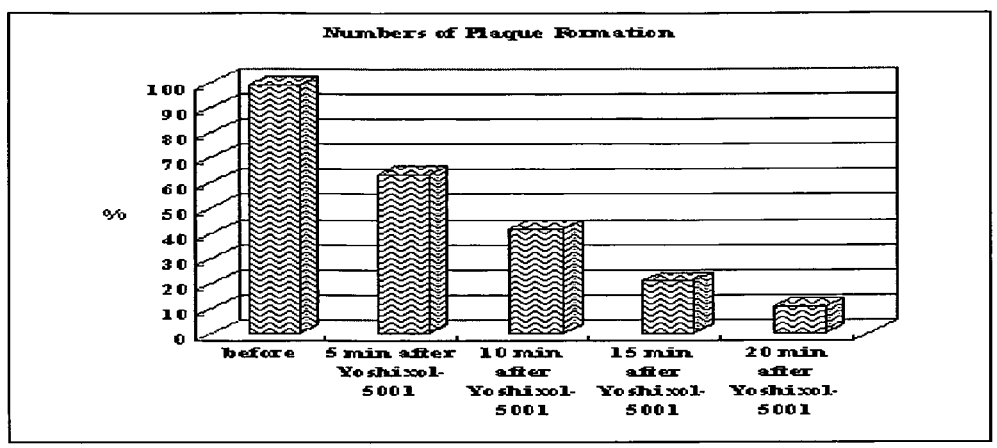
FIG. 14 is the graph which shows the effect of Yoshixol on numbers of plaques formation of the bacteriophage infected to *E. Coli*.

Yoshixol (4 µl) were added in 1 ml of phage solution (E79 double-chained DNA phage) which was adjusted on about $10^7$ per 1 ml, and were mixed well. Then, 10 µl of the mixture sampled after 5, 10, 20, 30 minutes was diluted by quickly adding in 10 ml of medium, so that 100 µl of the phage-diluted solution put into the test tube as the upper plate with the warmed gelatin agar, which was mixed with 100 µl of the indication bacterial solution (*pseudomonas aeruginosa*) cultured for one night. Then, the adjusted solution of the phages in the test tube was dropped on the agar plate and, homogeneous surface of the upper agar plate was produced by smoothly rotating the plate on the table. After resting it on the table about 10 minute when multilayer gelatin agar sufficiently became solid, they were stocked into the incubator at 37° C. After one night incubation, numbers of plaques were counted. As a result, the numbers of plaques in the 5 min-treated phage solution, in 10 min-treated phage solution and in the 15 min-treated phage solution with Yoshixol decreased to 33%, 15% and 6% of the plaques formation in the non-treated phage solution, respectively. Moreover, when the phage solution was treated with Yoshixol over 20 min, plaques formation did not find (referred FIG. 14).

<Concerning Antiviral Effect>

Figure 15:
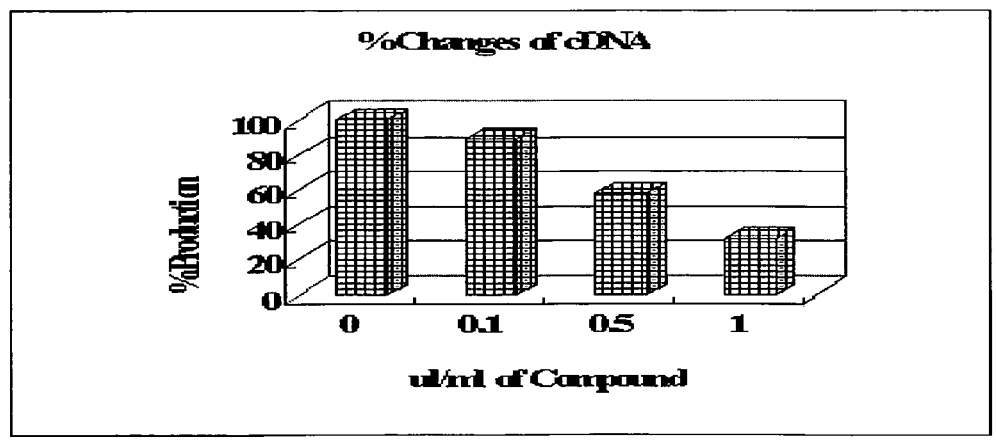
FIG. 15 is the graph which shows the effect of Yoshixol on chicken myeloblastosis virus (AMV) reverse transcriptase.

In order to investigate the effect on virus, changes in structure of single strand DNA, double strand DNA and mRNA of *E. coli* bacteriophage (1 ml of 1 mol solution), which were prepared as non-treated sample and treated sample with 4 µl of Yoshixol, were observed by scanning and transmission electron microscopes. In addition, according a general bacteriological technique, changes in proliferation and in morphological aspect (by scanning and transmission electron microscopes) of *E. Coli*, which was infected by single strand DNA, double strand DNA or mRNA, were investigated before and after treatment of each phage with Yoshixol. As treated samples, 4 µl of Yoshixol was added in 1 ml of each phage solution which concentration was adjusted to 1 mol. As a result, a characteristic helical and multi-dimensional structure with single strand DNA, double strand DNA and mRNA of *E. Coli* bacteriophage became a simple structure after treatment with Yoshixol and, a distance of the chain was markedly separated. On histological investigation of *E. coli*, an adhesion of the phage on the bacterial surface and/or intrabacterial existence were observed in the non-treated group, but not in the treated group with Yoshixol. In addition, an effect of Yoshixol on chicken myeloblastosis virus (AMV) reverse transcriptase (Gibco Co. Getesburg, Md., USA) was investigated by measuring amount of cDNA synthesis, which was amplified by PCR of RNA (5 µg) and AMV reverse transcriptase (25 units). As treated group, 0.01 µl of Yoshixol was added to 25 units sample of the AMV reverse transcriptase. Thus, the expected production of cDNA was obtained in the non-treated group, however, the amount of cDNA production decreased to 10% of the expected one when Yoshixol was treated (referred FIG. 15). This result shows that Yoshixol has inhibitory effect for self prolifelation ability within host cells, destroying action of virus, inhibitory effect for adhesion with host cells, and effect which causes a change in multi-dimensional structure of genes with virus oneself.

<Concerning Anti-cancer Effect>

Figure 16:
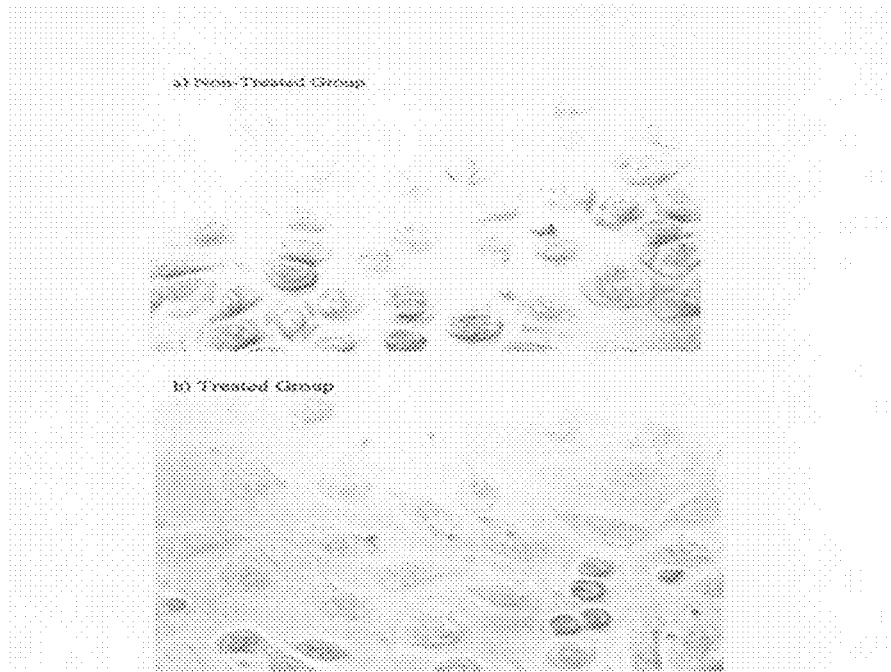
FIGS. 16 (a) and 16(b) are histological pictures which show the effect of Yoshixol on cultured keratinocytes, observed by a phase microscopy.
Figure 17:
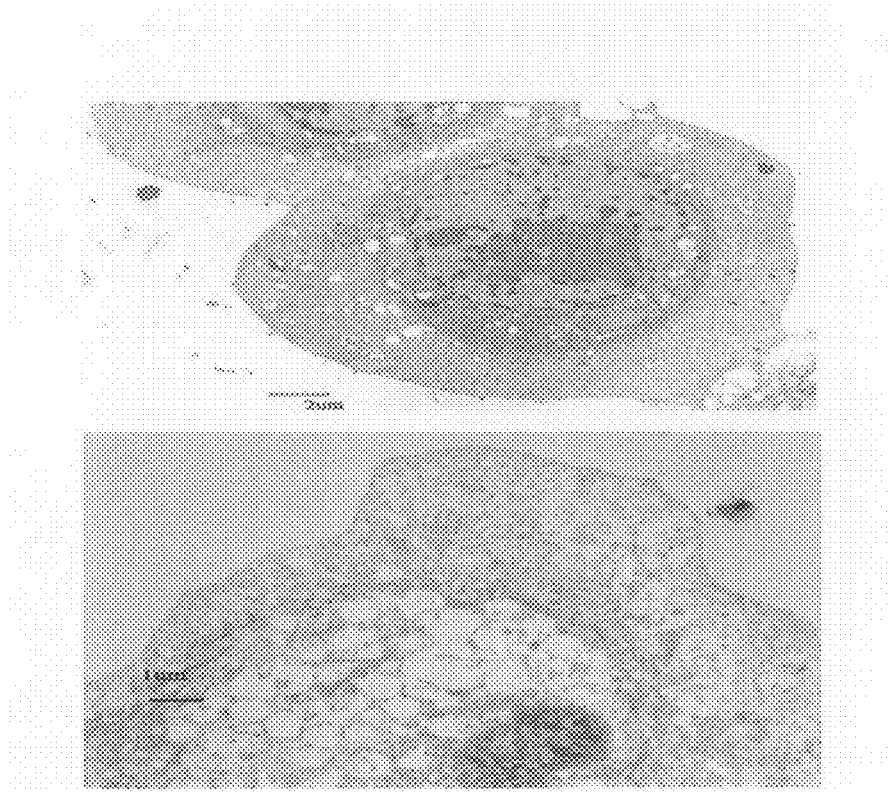
FIGS. 17(a) and 17(b) are histological pictures which show the effect of Yoshixol on cultured keratinocytes, observed by an transmission electron microscopy.
Figure 18:
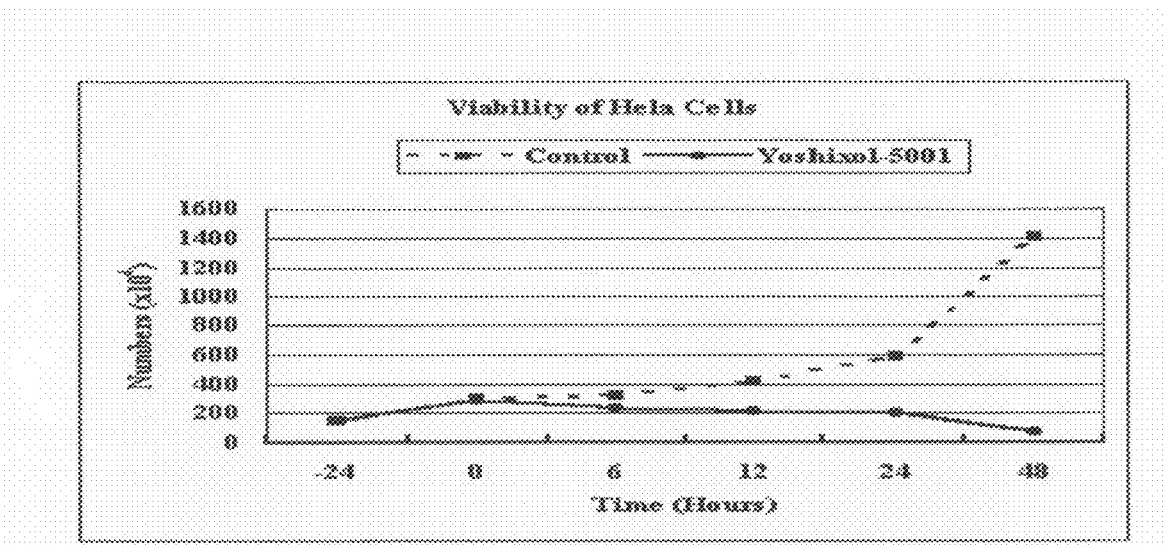
FIG. 18 is the graph which shows survival rate of the HeLa cells which were treated with Yoshixol.
Figure 19:
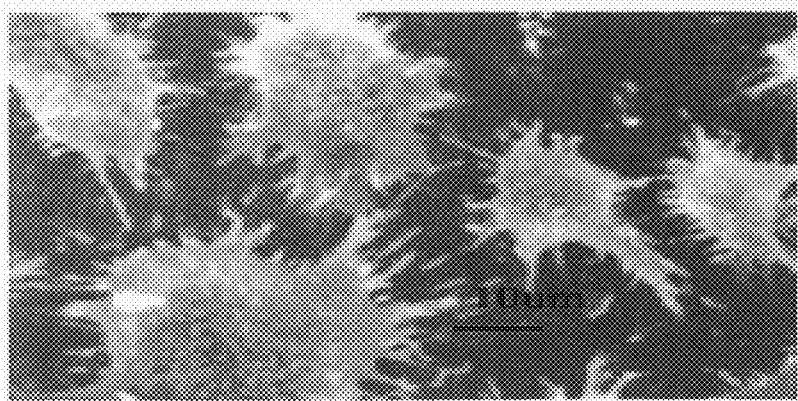
FIG. 19 is a picture of an scanning electron microscopy, which demonstrates a typical morphological aspect of the cell death of HeLa cells immediately after treatment with Yoshixol.

Adhesive factors between cells play an important role on prolifelation of malignant tumor cells and metastasis. In order to investigate the adhesive factors between cells, intracellular structure of cultured keratinocytes are utilized to observe. Thus, by using keratinocytes isolated from a human skin and cultured in this invention, structure between cells and cellular aspect of keratinocytes (5 days passed after culturing of second generation) were investigated by phase microscope (Olympus Co., IMT-2), transmission type (JEOL, Ltd. JEM 1200, EXII) and scanning type (JEOL, Ltd. JSM-6000F) electron microscopes. In the non-treated group with Yoshixol, the cultured cells proliferated monologously and in order as like as a stone wall. There were normal aspects of intracellular organella and mitosis. There were not blank spaces between cell and filling with intracellular matrix (referred FIGS. 16*a*, 17*a* In contrast, aspects of cultured cells in the treated group with 4 µl of Yoshixol showed diverse irregularity. Moreover, there were many cells which cell membrane and intracellular organella (Golji apparatus, rough endoplasmic reticulum, cytoskeleton which consists of tubulin) were destroyed with varieties and coupling between cells has also estranged in an irregularity. In addition, extracellular matrix has been also dispersed in an irregularity from cells as various sizes of particles (referred FIGS. 16b, 17b). These observations similar to the above were found in cultured HeLa cells (American Type Culture Collection, ATCC No. CCL2, Md, USA, referred FIG. 18) and cultured mouse hepatoma cells. This result shows that Yoshixol in this invention can suppress cell division and prolifelation, and can block adhesion between cells. And also, Yoshixol has an inhibitory effect of cell prolifelation and metastasis such as tumor cells. Additionally, from histological findings, aspects of destroyed cells due to Yoshixol is far from those of necrosis in cell death which has been reported (referred FIG. 19) and, is more close to the picture which have been reported as natural cell death or apoptosis (these morphologic images were investigated in various bacteria mentioned above). And also, these findings show that small particles destroyed from cell composition (10-100 nm) were cleaned up by phagocytosis of macrophages and/or lymphocytes, resulting in reuptaking those particles and being recycling into the natural physiological phenomena of living organism.

<Concerning Preservative Effect on Organs and Tissues>

Figure 20:
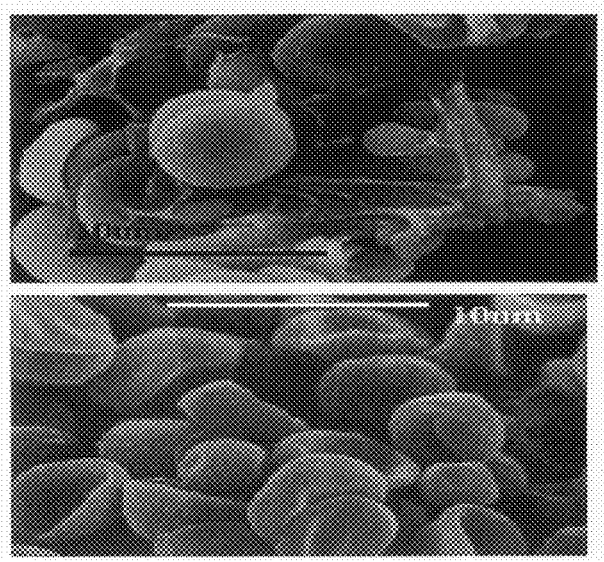
FIGS. 20(a) and 20(b) are histological pictures which show morphological changes of blood erythrocyte due to Yoshixol, observed by a scanning electron microscopy.

After sampling 5 ml of human blood from a cubital vein, the blood sample was replaced into the vacuum tube with 10 ml capacity and was mixed in a gentle. The vacuum tubes were divided by two group; one group is nontreated and another treated with 4 µl of Yoshixol. Then, changes in morphological aspects of blood, which were stored at room temperature, were observed by a transmission type and scanning electron microscopes at 30 minutes, one hour and 1 month after the sampling. When the blood sample was not treated with Yoshixol, coagulated masses were found 30 minutes after the sampling and, normal aspects of erythrocytes did not found. It was existed likely as a destroyed and aggregated mass. However, erythrocytes which were processed by Yoshixol did not show an aggregation with fibrin networks. Many stomatocytes (lip-like erythrocyte) and echinocyte which is appeared at a lack of pyruvate kinase were observed. However, cell membrane and intracellular organella were preserved normally over 1 month (referred FIG. 20). This result shows that blood treated with Yoshixol can be stored even in room temperature and has an effectiveness as preservative agents for organs and tissues which are functional units of body.

<Concerning Inhibitory Effect of Rejected Reaction on Heterogeneous Skin Implantation>

Figure 21:
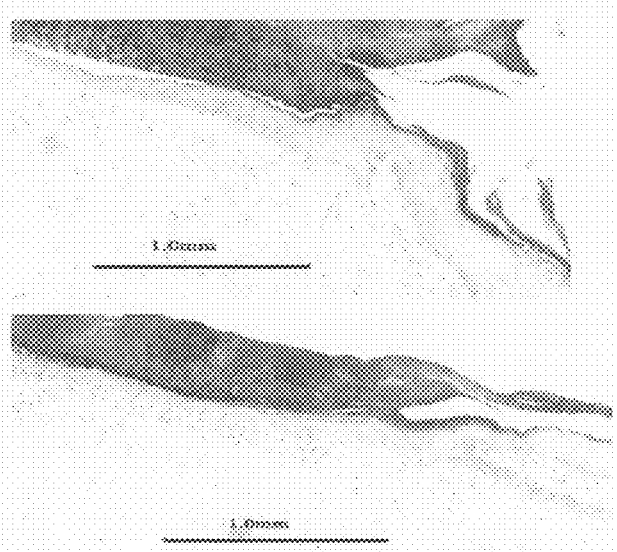
FIG. 21 is the histological picture that canine skin after treatment with Yoshixol was transplanted to rabbit, and that shows an implantable effect of rabbit skin as a donor to dogs as recipient when Yoshixol was treated intravenously after the transplantation.

Changes in transplanted skin for 3 months were observed by macroscopically and microscopically, when a piece of skin with entire layer (diameter 3 centimeter meter) at a region of the back of rabbit was transplanted to the region of the back of adult mongrel dog as the entire layer transplantation, and when a piece of skin with entire layer (diameter 3 centimeter meter) at a region of the back of adult mongrel dog was transplanted to the region of the back of rabbit as the entire layer transplantation. Firstly, each piece of skin from rabbit or dog was treated with 5 ml of physiological saline with 10 µl of the test solution for 2 minutes so that each skin piece was transplanted to each recipient by the surgical suture. Two kinds of the test solution were prepared for the above treatment; as control solution, basal solution consists of 2 ml of polyoxyethylene (20) sorbitan monoolate 1 (Wakou Jyunyaku Co.) which is identical to Tween 80 (ICI Ltd.) and 88 ml of physiological saline, and as treated solution, 10 ml of Yoshixol was added in the basal solution. And, 10 µl of Yoshixol was treated directly on the transplanted wound for 3 days after implantation. Desquamation of each transplanted skin which were treated with the basal solution as control group began on 3-5th days after implantation, and the transplanted wound showed extremely dirty aspect with tissue necrosis and inflammation reaction. After one week, the transplanted skin showed mummification so that it was dropped out from the recipient completely 10 days after the implantation. Then, implantated wound of the recipient was cured with a self regenerated skin of each recipient after 3 months. On the other hand, when a piece of transplanted skin is dipped in the Yoshixol solution, the treated skin became to be soft and increases in it's thickness. And, a suture procedure with surgical needle was easily done. The transplanted skin did not show a desquamation and deciduation 2 weeks after the implantation, and an inflammation reaction also was inhibited. So that an inflammatory tissue reaction was not also found after 1 month. The transplanted wound showed an aspect which was covered with chitin-like and lustered collagens-like substances so that the wound was cured to a level which could not find a boundary with a skin of recipient (upper panel of FIG. 21). These results show that Yoshixol can inhibit a rejection reaction for the transplantation by pretreatment of tissues or organs of donor with Yoshixol when heterogeneous transplantation of tissues or organs as well as skin was performed. Simultaneously with the above, Yoshixol can inhibit complications of infections on the donor tissues or organs, and can improve an implantation effect. Moreover, by using an entire layer (diameter 3 centimeter meter) of rabbit skin, changes in a piece of the transplanted skin which was sutured to the back of the dog as the recipient were investigated over 3 months after the implantation. The rabbit skin did not receive the pretreatment with Yoshixol. The recipient dogs were received 10 µl/Kg per day of Yoshixol intravenously for one week, and they did not receive any kinds of conventional antibiotics and/or immunosuppressants. It was found that an transplanted skin was implanted on the back of dog over 1 month without a rejection reaction and bacterial infection. An outer layer of the transplanted skin was faded 3 month after the implantation likely as to strip a thin membrane. But, though an appearance of a hair was not found in a wounded skin, well epithelialization was found macroscopically and microscopically (lower panel of FIG. 21). In addition, by this intravenous administration of Yoshixol, adult mongrel dog also became vigor, youthful and appetite-well in comparison with behaviors before the treatment. This result shows that Yoshixol can inhibit a rejection reaction of the transplantation as well as an improvement of physical status due to the intravenous administration. And, it can also simultaneously inhibit infections and can improve an implantation effect.

<Concerning Thrombolytic Effect>

Figure 22:
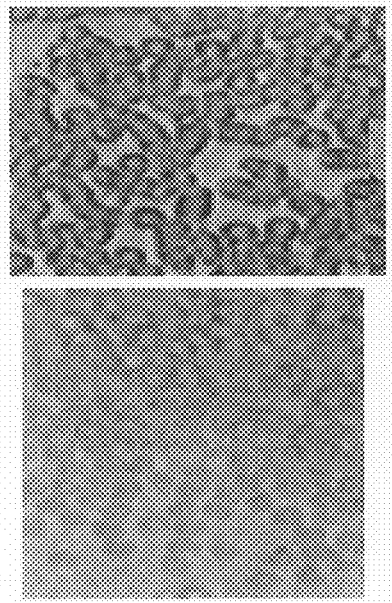
FIG. 22 is a picture which shows a thrombolytic effect of Yoshixol on fresh thrombus.

In order to investigate a thrombolytic effect of Yoshixol on thrombus, 1 ml of human blood or canine blood were sampled by a syringe and transferred into the Petori-schale (grainer lab. GmHB) so that thrombus formation and rouleaux formation were observed under a phase contrasted microscopy (IMT-2, Olympus Co.). Then, 1 µl of Yoshixol was added in the blood sample when all visual fields could not be discriminated as an normal individual erythrocyte by thrombus formation. Then, a thrombolytic process of the thrombus was investigated and the process was recorded to a video tape via a collar video camera (CCD-IRIS, Sony Co.). The video pictures were analyzed as a liquid phenomena by an original software of dynamic state analysis. When Yoshixol was added in the sample, the thrombus which has consisted with a mass has completely individualized to each erythrocyte via a reversed process of the thrombus formation. And, while original form of erythrocyte was recovered, each erythrocyte was marvelously dispersed from thrombus. In addition, hemolysis due to swelling and rupturing each erythrocyte did not occur. Each position of the individual erythrocyte did not disturb a position of other erythrocyte, and as a whole there was a dynamic state with a defined order (referred FIG. 22). On being analyzed this process by a dynamic image processing or microscopically, the pattern of this process showed a behavior as a dissipative mass similarly to phenomenon of liquidarization of solid materials or gelatinization phenomenon. This result show that mechanism of thrombogeneis in the blood and serum which is one example of non-newtonian physical property is interpreted by thermodynamically. And, Yoshixol has a potential to improve circulatory hindrance which is disturbed physiological role on original blood such as fluidability by being solidability. Yoshixol can apply as thrombolytic agents as well as inhibitory agents for thrombus formation.

<Concerning Effect on Improving Metabolism>

Figure 23:
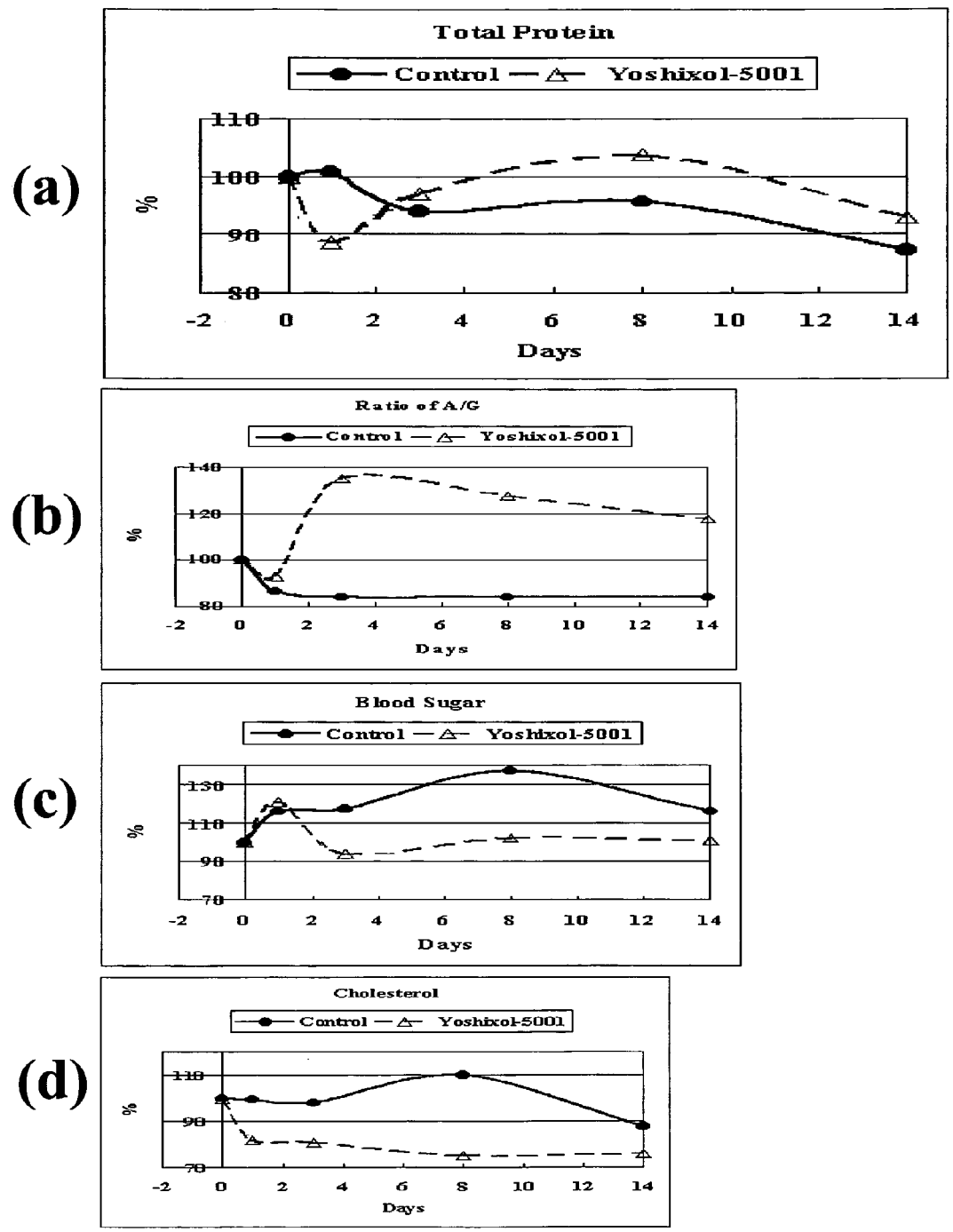
FIG. 23 are graphs which show the effect of Yoshixol on change in amount of total proteins and concentration of serum albumin when Yoshixol was administered orally in dog.
Figure 23:
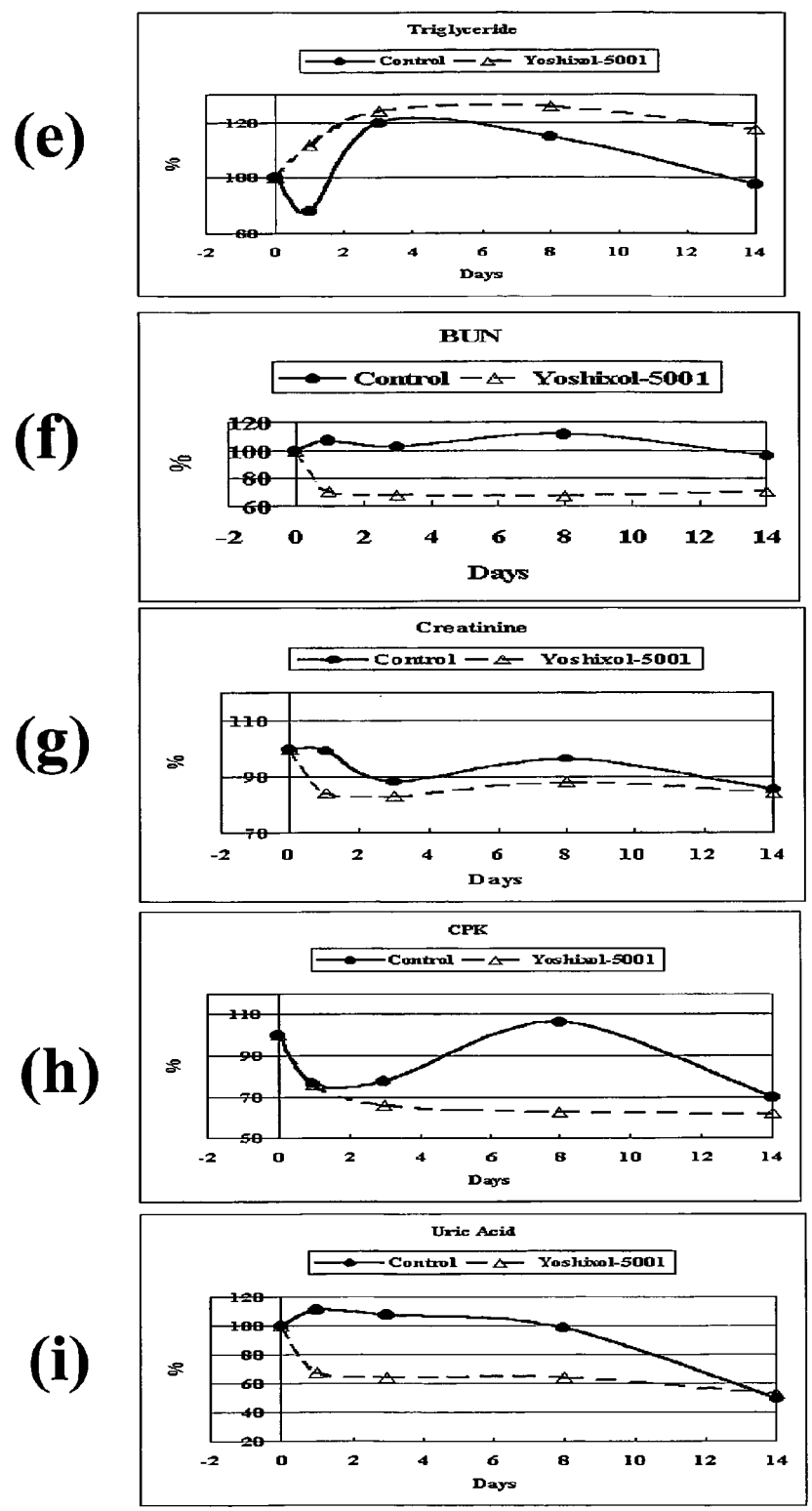
Figure 24:
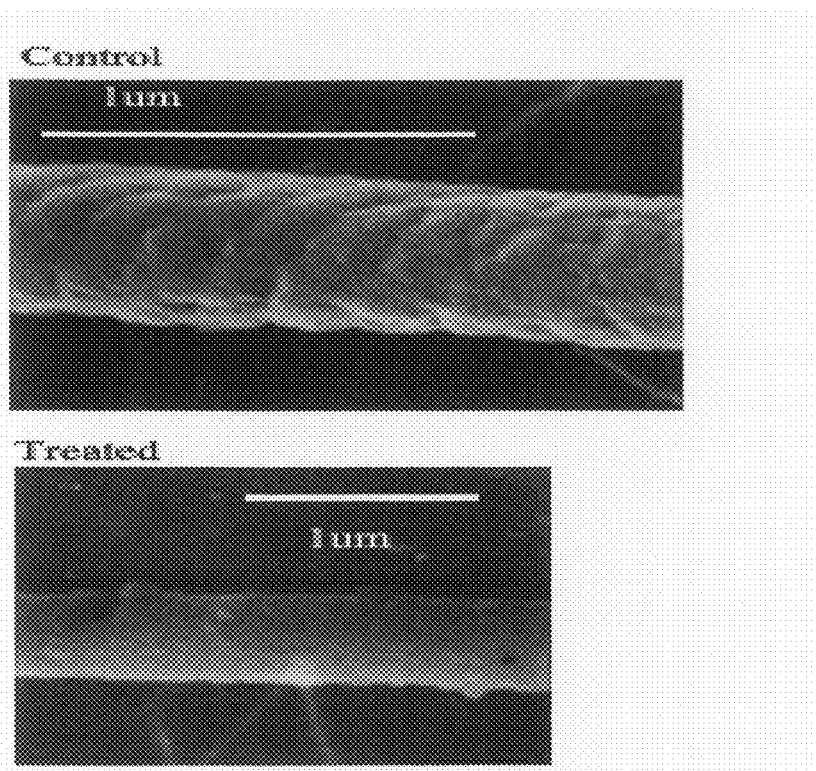
FIG. 24 are graphs which show the effect of Yoshixol on change in amount of concentration of serum globulin and ratio of albumin vs globulin when Yoshixol was administered orally in dog.
Figure 25:
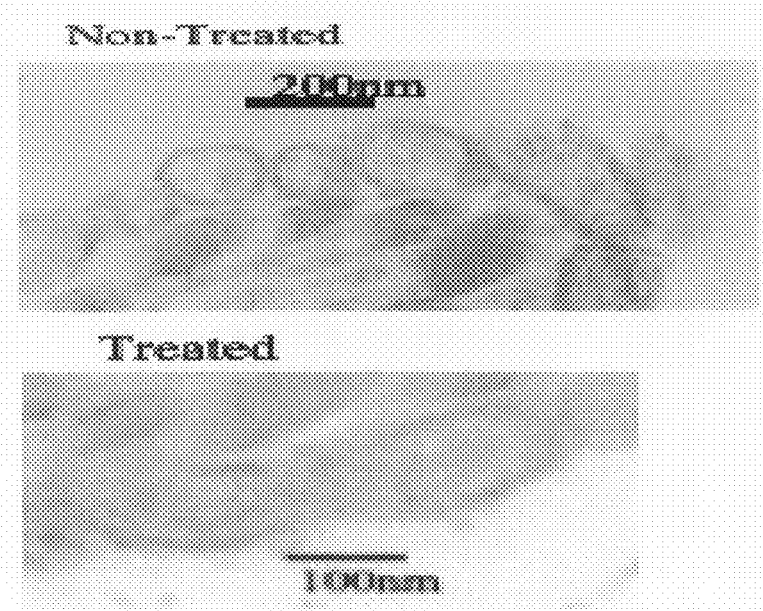
FIG. 25 are graphs which show the effect of Yoshixol on change in total cholesterol and concentration of serum triglyceride when Yoshixol was administered orally in dog.
Figure 26:
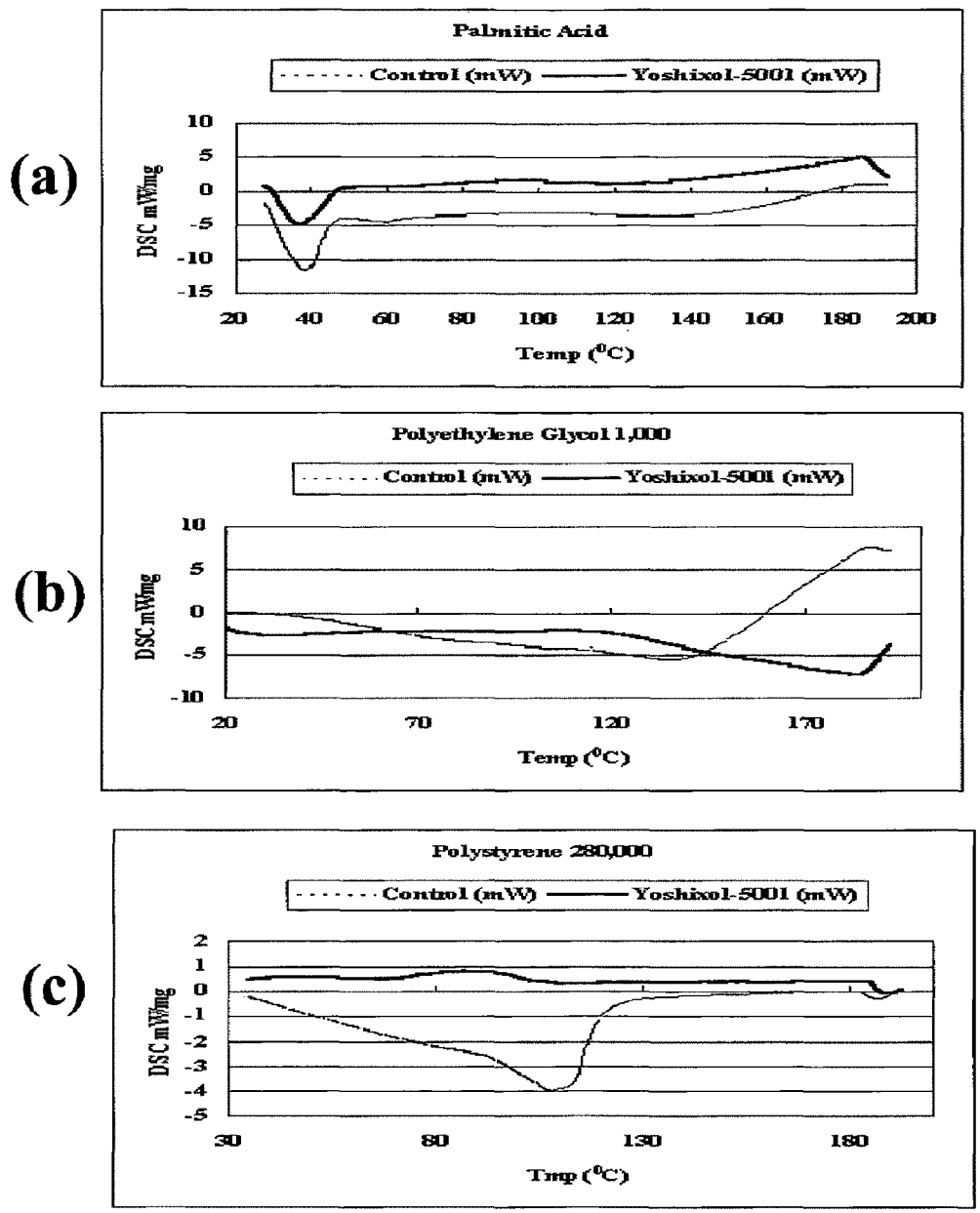
FIG. 26 are graphs which show the effect of Yoshixol on change in serum nonproteins nitrogen and concentration of serum creatinine when Yoshixol was administered orally in dog.
Figure 26:
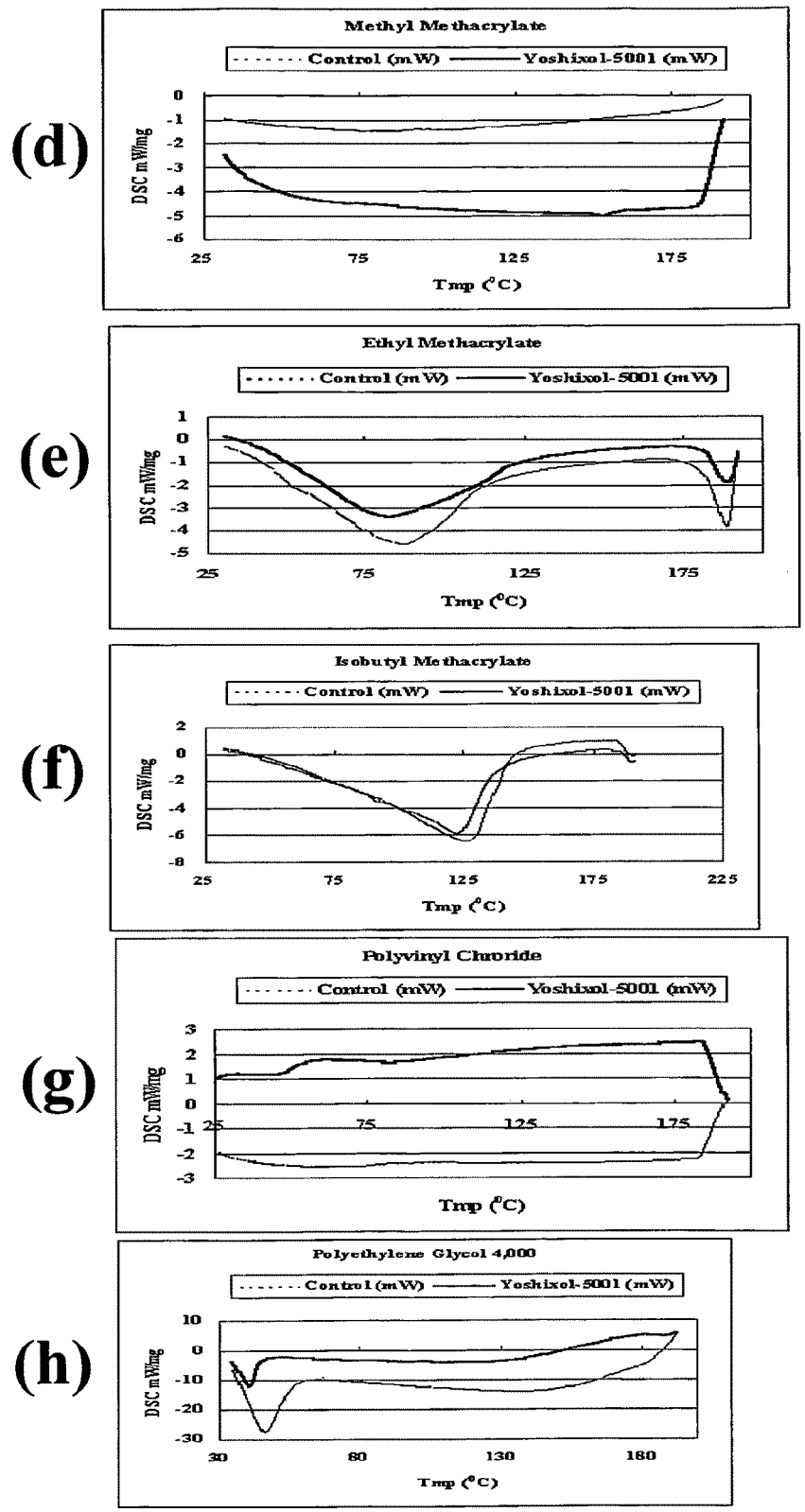
Figure 26:
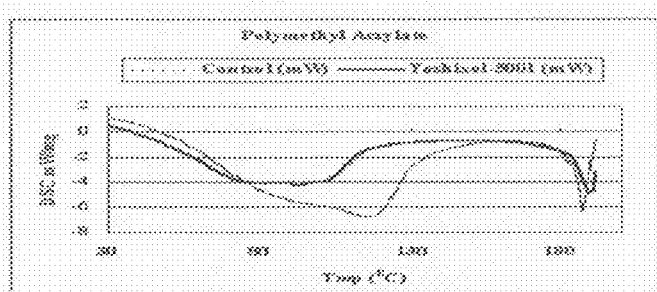
Figure 27:
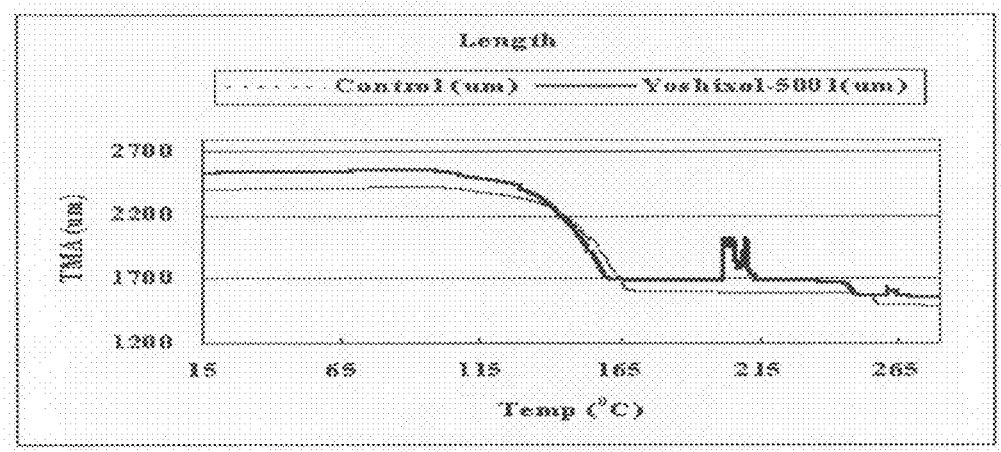
FIG. 27 are graphs which show the effect of Yoshixol on change in concentration of serum creatinine when Yoshixol was administered orally in dog.

In order to investigate changes in blood cells, chemical components in blood and improving effect on metabolism after oral administration of Yoshixol, 10 μl per body weight of Yoshixol was mixed with 100 g of dog foods ("dog foods<beef>", produced in New Zealand, imported by Daiei, Inc., followed by pet food fair trading committee standard), this food was given to the beagles as their feedstuff. Oral administration was continued for 1 week, and samplings of blood was performed before, 1 day after and 3 day after administration, and 1 day after and 7 days after the stop of the administration. And, red blood cells, white blood cells and platelets were counted. Also, total proteins (Byuret method) in a blood serum, albumin (BCG method), urea nitrogen (GLDH-UV method), creatinine (enzymic method), glucose (GDH method), total bilirubin (enzymic method) are measured. GOT and GPT (JSCC sub method), TTT and ZTT (standard method of research project of liver function), cholinesterase (DMBT method), total cholesterol (PDO enzymic method), triglyceride (PDO enzymic method), uric acid (urikase PDO method), serum iron (nitroso PSAP method), creatinine phosphokinase (SCC sub method), sodium, potassium and chloride (ISE dilution), inorganic phosphorus (enzymes-UV method) and calcium (OCPC method) were also measured. As a result, any changes in numbers of red blood cells, white blood cells and platelets did not found. Moreover, any changes in concentration of total bilirubin, GOT, GPT, TTT, ZTT, cholinesterase, serum iron, potassium, sodium, chloride, inorganic phosphorus and calcium did not found. However, total proteins increased 3 days after administration of Yoshixol followed by recovery to a same level in the control 1 week after the stop of administration. Though albumin level did not change (referred FIG. 23), albumin/globulin ratio was elevated 3 days after administration (referred upper panel of FIG. 24) indicating of newly producing globulin. Moreover, though blood sugar level was elevated by 15% of the control group 3 days after taking feedstuff, this elevated blood sugar level did not found in the treated group with Yoshixol and the rebound phenomena of the glucose metabolism did not occur 1 week after the stop of administration (referred lower panel of FIG. 24). A difference in concentration of total cholesterol and triglyceride between groups did not occur (referred FIG. 25). But, levels of nonproteins nitrogen and creatinine in the serum showed lower value (70-80% of the control) since 1 day after administration (referred FIG. 26), and level of uric acid also was maintained at lower level during the administration. In addition, creatinine phosphokinase fell (referred FIG. 27), and enzymes such as γ-GPT, GOT, GPT also fell. TTT and ZTT did not show abnormal values. During this administration of Yoshixol and 1 weeks after stopping administration, any abnormal behaviors, diarrhea, vomiting and bloody feces, loss of the weight and appetite loss were not observed. Moreover, even though 3 μl per body weight of Yoshixol was administered for one month to the beagles and the parameters of blood samples were observed during 3 months, a similar effect of Yoshixol to the above experiments could be obtained even though there was a difference of the time-lag and a degree. These results show that oral administration of Yoshixol can be expected several effects to improve metabolism and nutrition such as saccharides, lipids and proteins. Thus, Yoshixol can apply as therapeutic drugs into protective agents for cellular function as well as agents for diabetes, kidney diseases, heptic diseases and hypoproteinsemia.

<Concerning softening and flexibility effect on skin>

In order to investigate changes of softening and flexibility on skin from rabbit and dog, each skin was is dipped in 5 ml of physiological saline with 10 μl of the test solution. This test solution was prepared from 88 ml of physiological saline with 2 ml of polyoxyethylene (20) sorbitan monoolate 1 (Wakou Jyunyaku Co.) that is identical to Tween80 (ICI Co.) as the basal solution of control. As the treated solution, 10 ml of Yoshixol was added in the basal solution. When each skin sample was dipped in the test solution for approximately 1-2 minute, the treated skin became soft, wetly and thicken. Surgical stitching by the needle was easily to be inserted and transfixed in the skin. Additionally, structure damages of each skin did not found histologically. And, the sample treated with Yoshixol was observed as the preparation which was made from a fresher sample by hematoxylin eosin staining in contrast to the skin sample treated with the test solution of control. Moreover, a similar observation on histological pictures of each sample was obtained even when each skin sample was thawed at 20° C. after storaging each sample at 4° C. in the refrigeration for one month. This result shows that it is possible that Yoshixol can apply as flexibility promoters and/or softners of the tissues and/or substances which have fiber structures such as skin and, that Yoshixol can utilize as preserving agents for organs.

<Concerning Inhibitory Effect on Flagellum Motility of Spermatozoa>

Figure 28:
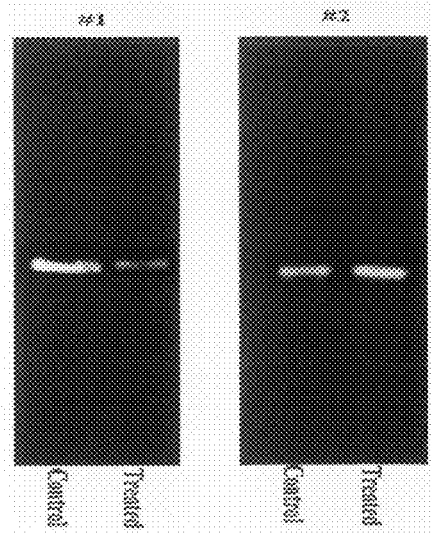
FIG. 28 are histological pictures which show the effect of Yoshixol on flagellum of bovine spermatozoa, observed by a scanning electron microscopy.
Figure 29:
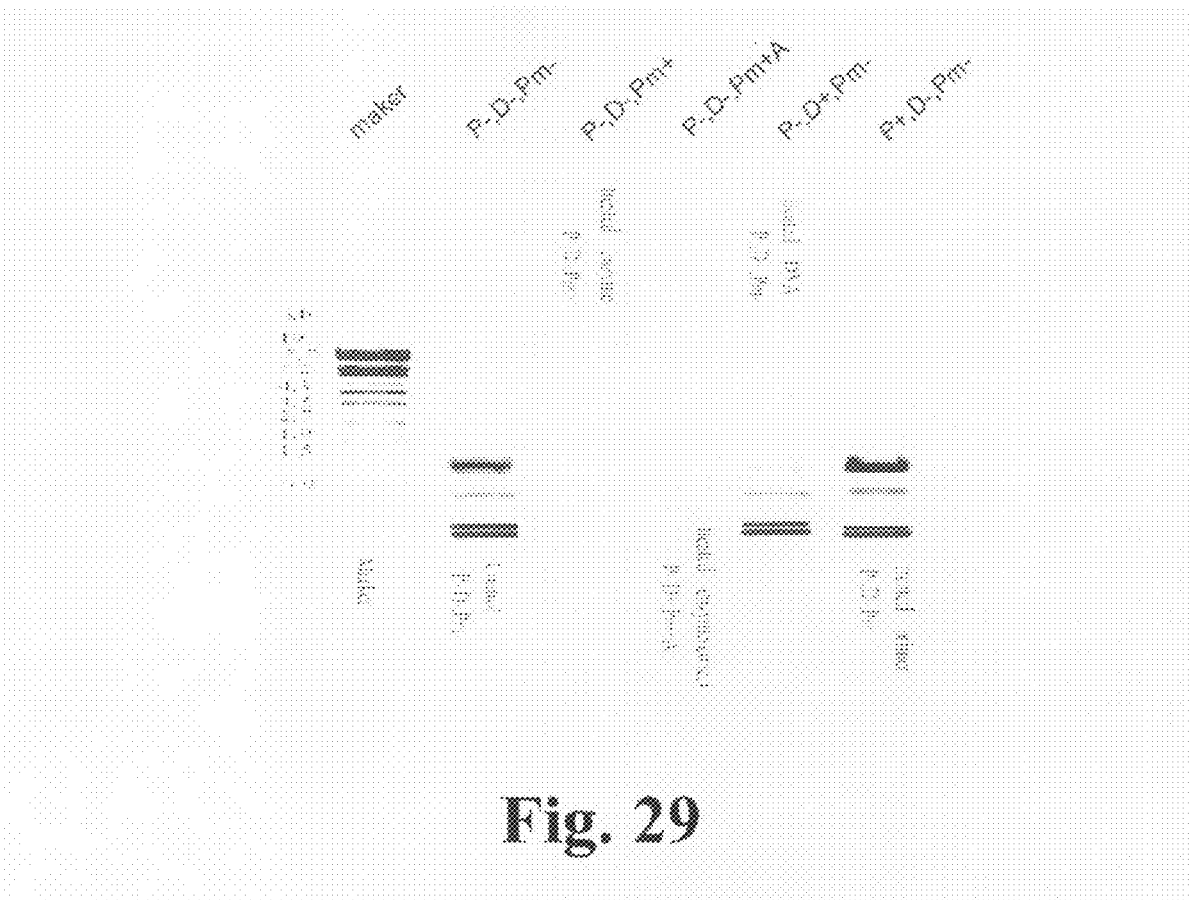
FIG. 29 are histological pictures which show the effect of Yoshixol on flagellum of bovine spermatozoa, observed by a transmission electron microscopy.

In order to investigate an effect of Yoshixol on a flagellum motility of spermatozoa, the spermatozoa (seed japanese bull ID: Sinmorihide<registration No. Zen-Wa-Kuro1114, lot No. 84Y28>) which has been conserved in the liquid nitrogen was thawing at 35° C. After thawing, 1 ml of semen was transferred to Petori-schale (grainer lab.GmHB) and, flagellum motility was observed by a phase contrast microscopy (IMT-2, Olympus Co.) and was recorded by a video film via a collar video camera (CCD-IRIS, Sony Co.) so that wave cycles and speed of the flagellum were analyzed by an original software of dynamic state analyzer. While a head of normal spermatozoa was transferred by regular movement of a flagellum at the speed of 0.3-1.5 mm per second, a flagellum movement was immediately inhibited after 1 μl of Yoshixol was added so that velocity of spermatozoa became zero. However, though a flagellum movement was completely stopped, the rotation of the head which occurs at the centriole (near junction between head and tail) was found during a few 10 seconds. And, a speed of this rotation gradually was decelerated with progress of a time. This result shows that Yoshixol is related to physical property and function property of substance (for example, actin such as contraction proteins and hydrolysis reaction of ATP as energy source) which is concerned with a flagellum movement of spermatozoa, so that Yoshixol is related greatly on a movement and signal transduction of the procaryotes and eucaryotes, and on the dynamic behavior which is essential qualities of living organism. Moreover, from the knowledge that these movements of cells are involved in microfilaments and microtubles which is constricted from the proteins assembly, a morphological change of this spermatozoa due to treatment with Yoshixol was investigated by transmission type (JEM1200, EXII, JEOL, Ltd.) and scanning type (JSM-6000F, JEOL, Ltd.) electron microscopy. The outside of normal flagellum with regular basic structure of 9+2 is enclosed with a cell membrane and, there was the axial filament which structure is related to a movement is observed inside. The axial filament has two pairs of tubles (centrum pair) that exist mainly on the center and nine double tubles that exist in a periphery (circumscription canaliculus). The surface structure contributed to the movement was observed to make ring formation likely to the doughnuts, which are configured orderly and smoothly on the surface. But, though morphological aspect as a whole of spermatozoa was not altered by the treatment with Yoshixol, many particles with a size of 10-30 nm on the surface were observed likely to be blowed out, when the surface structure of flagellum was investigated by a magnification. And also, ring formation likely to a doughnut in which region is contributed to the movement was not found and, adhesion of small particles were noticeable (referred FIG. 28). Moreover, while fundamental fiber units of a flagellum were maintained on the transmission electron microscopic observations, there were a lack of continuity of the membrane which surrounds-fibers of the surface and a lack of regular alignment configuration whose fiber units (myofibrille) inside of the each unit of fiber construction. And, an appearance of high-density aggregated substance was found (referred FIG. 29). Moreover, the morphologic changes in the surface and intracellular organella of the head were not found in contrast to findings of marked changes in flagellum. These results show that in the present situation which many interests involve in a role as cytoskeleton which is related to dimer formation of actin and tubulin (for example, oncogeneis, metastasis, cell death and so on), Yoshixol can apply into inhibitory agents of bacteria prolifelation for procaryotes, antibacterial agents and/or anticancer agents for eucaryotes as well as application as the contraceptive agents which can control and/or inhibit a motility of spermatozoa. Moreover, it is shown that Yoshixol can apply into inhibitory agents or control agents for generating function which is based on the polymerization reaction related with morphogeneis, cell adhesion and each life events (for example, immune response).

<Effect on Changing a Physical Property with Macromolecule>

Changes in physical properties (for example, change of glossy or shiny and luster, accurate boundary on casting formation, smoothness and homogeneity of surface, transparence, texture minuteness, change in quantity and so on) of macromolecules due to Yoshixol were investigated. In other words, 100 μl of Yoshixol per 100 g of following each substance was added. Then, each sample was processed with heating within a water tank until the melting followed that the melted sample was poured into a filling teeth-marks phantom of caries which is used at the odontotherapy. After cooling and taking out from a template, in the state which became solid, the surface of each sample was observed by 2-5 times magnification with loupe. A fall of melting point in the all substances treated with Yoshixol, which substances are shown below, was found in comparison with the object which is not added. In octadecanol (Wakou Jyunyaku Ltd., Osaka) with Yoshixol, glossy, shiny and luster became better and boundary also became more clear and sharp. In stearic acid (Wakou Jyunyaku Ltd., Osaka) with Yoshixol, an appearance of transparence, smooth of a surface and texture minuteness is characteristic. In lauric acid (Wakou Jyunyaku Ltd., Osaka) with Yoshixol, smoothness and transparence appeared. In dodecanol (lauryl alcohol) (Wakou Jyunyaku Ltd., Osaka) with Yoshixol, melting became markedly and casting form could not be kept by room temperature. In palmitic acid (Wakou Jyunyaku Ltd., Osaka) with Yoshixol, a soft feeling appeared. In myristic acid (Wakou Jyunyaku Ltd., Osaka) with Yoshixol, clearness of boundary and homogeneity appeared, and also in tetradecanol (miristyl alcohol) (Wakou Jyunyaku Ltd., Osaka) with Yoshixol, clearness of boundary and homogeneity appeared. In hexadecanol (Wakou Jyunyaku Ltd., Osaka) with Yoshixol, it was a characteristic that texture minuteness and transparence fell. In decanoic acid (Wakou Jyunyaku Ltd., Osaka) with Yoshixol, a rough surface and a small prominence appeared though luster and boundary clearness appeared. In polyethylene glycol 1000 (Wakou Jyunyaku Ltd., Osaka) with Yoshixol, clearness of boundary and smoothness get worse. In polyethylene glycol 1540 (Wakou Jyunyaku Ltd., Osaka) with Yoshixol, transparence, smoothness and homogeneity gets better. In polyethylene glycol 2000 (Wakou Jyunyaku Ltd., Osaka), polyethylene glycol 4000 (Wakou Jyunyaku Ltd., Osaka) and polyethylene glycol 6000 (Wakou Jyunyaku Ltd., Osaka), an increment effect of texture minuteness, transparence and expansibility was found after Yoshixol. In addition, luster, clearness of boundary, homogeneity of a surface, transparence and texture minuteness were found in N-isopropylacrylamide (Aldrich Co. Milwaukee, Wis., USA with Yoshixol. Moreover, in order to investigate an effect of Yoshixol on polymers as macromolecules, acrylate polymers were tested as one of a concrete example. Standard grade of lauryl methacrylate 471, methyl methacrylate 48, ethyl methacrylate 126, isobutyl methacrylate 140 and butyl methacrylate 320 (polymer kit, acrylate polymer standard 18336-9, Aldrich Co. Milwaukee, Wis., USA) were used and were observed at room temperature. When 150 μl of Yoshixol was added in 1 g of each acrylate macromolecules, all substances becomes liquid and glass-like transparent and, powdered and crystal configuration disappeared so that these were changed in the homogeneous substances. In addition, when 100 μl of Yoshixol is addendum in the above lauryl methacrylate 471, fluidability increased immediately. Floating viscosity appeared after 2 weeks and, there was separation of solid component with translucent and fluidable component one month after adding Yoshixol although the volume of sample was decreased in the group without Yoshixol. In methyl methacrylate 48, a dried powder state disappeared immediately after addendum of Yoshixol and, fluidability increased and was likely to a rice cake so that it became paste-like with after 2 weeks and adhered on the wall of tube, and volume of this sample was increased after 1 month. Dried powder-like aspect disappeared even in ethyl methacrylate 126 immediately after addendum of Yoshixol and, viscidity with lumpy appeared immediately after addendum of Yoshixol so that after 2 weeks it became paste-like and it adhered in the wall of tube. More transparence was increased after 1 month. Dried powder-like aspect disappeared even in isobutyl methacrylate 140 and, viscidity with lumpy transparence appeared so that viscosity was increased and it became paste-like after 2 weeks. Though the sample which adhered on the wall of tube was transparent, an unreaction part of substratum had a color in a powdered state before treatment with Yoshixol. In butyl methacrylate 320, a powdered state disappeared and viscosity, lumpy and transparence were increased after addendum of Yoshixol. The sample was adhered paste-like on the wall of tube. Though there is a difference of transparence according to the adhesive state after 2 weeks, a transparent part of the sample had a vitrified transparence. So, the sample became to be less viscidity and more homogeneous glass-like mass with transparence after 1 month, and the quantity of the sample also was increased. In addition, changes in the physical property of other polymers in acrylate group were investigated by using standard grade polymers (polymer kit, polyacrylate standard 18338-5, Aldrich Co. Wisconsin, Milwaukee, USA). The kit contained poly(2-ethylhexyl acrylate), poly(methylacrylate), poly(octadecyl acrylate), poly(ethyl acrylate) and poly(butyl acrylate). Then, 500 mg of each sample was treated with 200 µl of Yoshixol at room temperature. An increase in fluidability occurred in poly(2-ethylhexyl acrylate) immediately after treatment with Yoshixol, however, color of the sample did not change. Fluidability and capacity were increased more after 2 weeks, and also the refraction of light was changed. In addition, fluidability was increased after 1 month in addition, and a capacity also was increased by twice. In poly (methylacrylate) with Yoshixol, an increase in fluidability and a cubic capacity was observed, and optical transparence also became better. Fluidability has been enhanced after 1 month, and a capacity also did a gain almost 2-3 times. In poly(octadecyl acrylate) with Yoshixol, a dried powder state disappeared, and the sample became homogeneous and lumpy mass. In poly (ethyl acrylate) with Yoshixol, fluidability was increased markedly and became fluidable, and a marked increase in capacity occurred so that fluidability of the sample was increased and volume of the sample was gained by 3 times after 1 month. In poly(butyl acrylate) with Yoshixol, fluidability also was increased. In addition, the fluidability of the sample was increased more after 2 weeks and the sample became to be more fluidable. A volume of the sample was increased by almost 2-3 times as well as an increment of fluidability after 1 month. Moreover, changes in the physical property of other polymers were investigated by using standard grade polymers (polymer kit 18337-7, Aldrich Co. Wisconsin, Milwaukee, USA). The kit contained poly(dimethyl siloxan), poly(vinyl acetate), poly(methyl methacrylate), poly(vinyl chloride) and polycarbonate resin. Then, 500 mg of each sample was treated with 200 µl of Yoshixol at room temperature. In poly(dimethyl siloxan) with Yoshixol, though Yoshixol was difficult to be mixed with the sample just after the treatment and it was on the top as a liquid layer, an increase in a cubic capacity and fluidability occurred after 2 weeks. A viscosity and a quantity of the sample were gained after 1 month, however, optical transmission was decreased. In poly(vinyl acetate) with Yoshixol, viscosity was increased and the sample was adhered on the wall of tube though a fluid component was observed on the bottom of the tube. However, fluid component in the tube disappeared after 2 weeks so that the sample became to be a viscous solution with transparence and an increment of transparence was observed. In addition, transparence of the sample became very stable after 1 month. In poly(methyl methacrylate) with Yoshixol, the sample was frosted glass-like and crystal after 1 month though it resulted in the state which was massive homogeneously with transparence immediately after Yoshixol. In poly(vinyl chloride) with Yoshixol, a dried powder state of the control sample disappeared and the sample became to be an ununiformed mass with small granules. A marked change was not observed when the sample was placed at room temperature. In polycarbonate resin with Yoshixol, a powder-like granule disappeared immediately after Yoshixol and the sample became to be adhesive. Additionally, though transparence fell after 2 weeks and a reflected light was not observed by a frosted glass-like change, a volume of the sample was observed after 1 month. Moreover, when 100 µl of Yoshixol are added to 200 mg of N-isopropylacrylamide (Aldrich Co. Milwaukee, Wis., USA), Yoshixol was permeated into a crystal as likely as that a sugar indulges in water. Subsequently, after 2-3 minutes, a formation of substance with transparence occurred from a side of the bottom of the tube without generation of fever and vapor resulting in a sherbet-like substance after 4 hours. And, the sample after 2 weeks was frosted glass-like with less transparent.

Moreover, 100 µl of Yoshixol was added in 200 mg of polyethylene glycol phenylether acrylate (Aldrich Co. Milwaukee, Wis., USA), polyethylene 125,000 (Aldrich Co. Milwaukee, Wis., USA) and polyethylene low density (Aldrich Co. Milwaukee, Wis., USA) as another macromolecules in polyethylene group. Each sample was observed at room temperature. In polyethylene glycol phenylether acrylate with Yoshixol, an increase in fluidability was observed just after the treatment. As a time passed, it was also observed increases in optical transparence and volume of the sample. Moreover, in polyethylene 125,000 with treatment, an adhesion between granules occurred so that each granule of the sample became to be adhered after 2 weeks though a grained form has been left. In addition, in polyethylene low density with the treatment, the sample became to be bigger granular from powder-like. Moreover, in order to investigate an effect of Yoshixol (100 µl) on macromolecules in polystyrene group, 200 mg of polystyrene 45,000 (Aldrich Co. Milwaukee, Wis., USA), polystyrene 280,000 (Aldrich Co. Milwaukee, Wis., USA) and polystyrene standard (Aldrich Co. Milwaukee, Wis., USA) were used. When Yoshixol are added on polystyrene 45,000, powder-like granules of polystyrene 45,000 disappeared, and viscidity of the sample appeared, and the sample became transparent and a crystal structure of the sample was lost. These properties did not alter even after 1 month. Powder-like granules disappeared in polystyrene 280,000 after treatment so that particle configuration of the sample was lost in parallel with an appearance of viscidity. Optical transparence became to be better likely as a transparent glass even when 1 month has been passed. A similar change in physical property was observed in polystyrene standard. Moreover, when 100 µl of Yoshixol was added in 200 mg of hydroxylated polyethylene vinyl alcohol (Aldrich Co. Milwaukee, Wis., USA), the sample became lumpy with ununiform and easy breakage from dried powder-like substance. When the time was passed, the sample became dried powder-like lumpy again, and also became adhesive to the wall of tube. These results show that Yoshixol can improve the physical property of macromolecules and the function which is generated or induced by structure of macromolecules.

Figure 30:
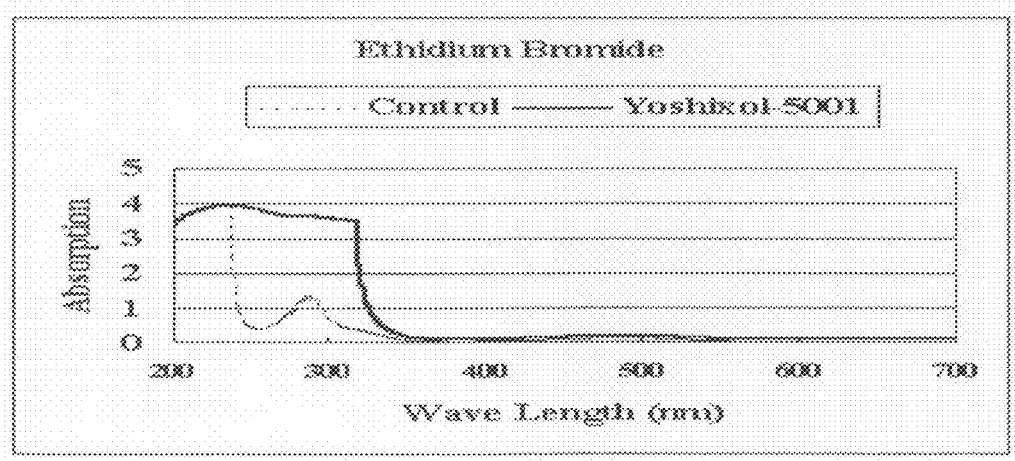
FIG. 30 is a graph which shows a calorimetry effect of Yoshixol on palmitic acid, measured by a digital scanning calorimeter.
Figure 31:
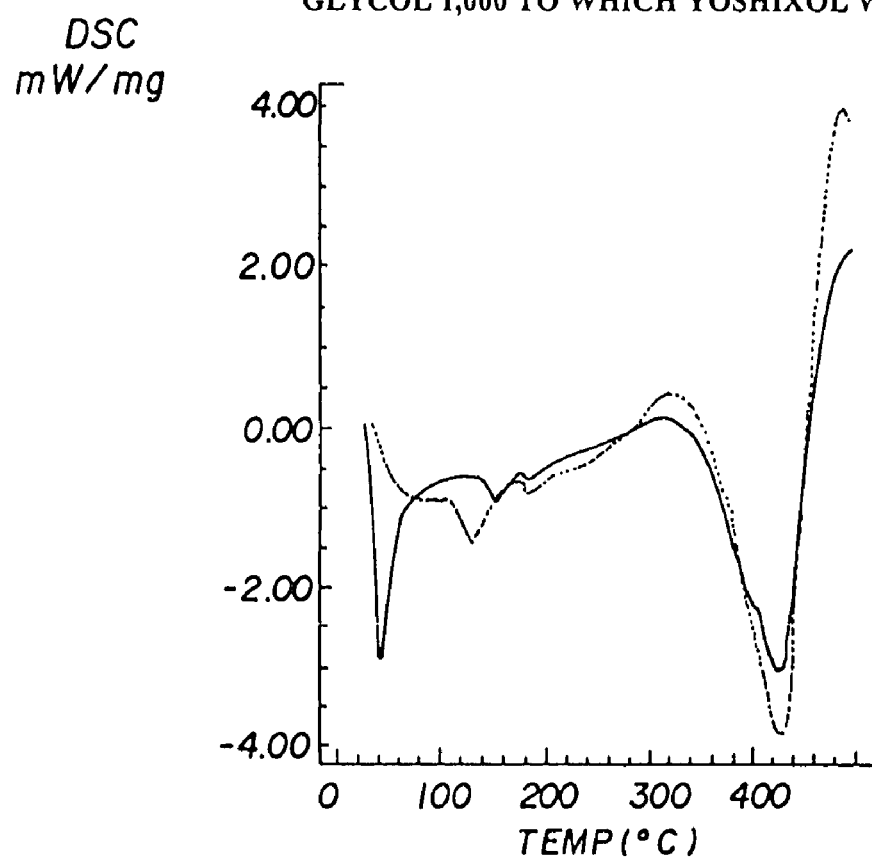
FIG. 31 is a graph which shows a calorimetry effect of Yoshixol on polyethylene glycol 1000, measured by a digital scanning calorimeter.
Figure 32:
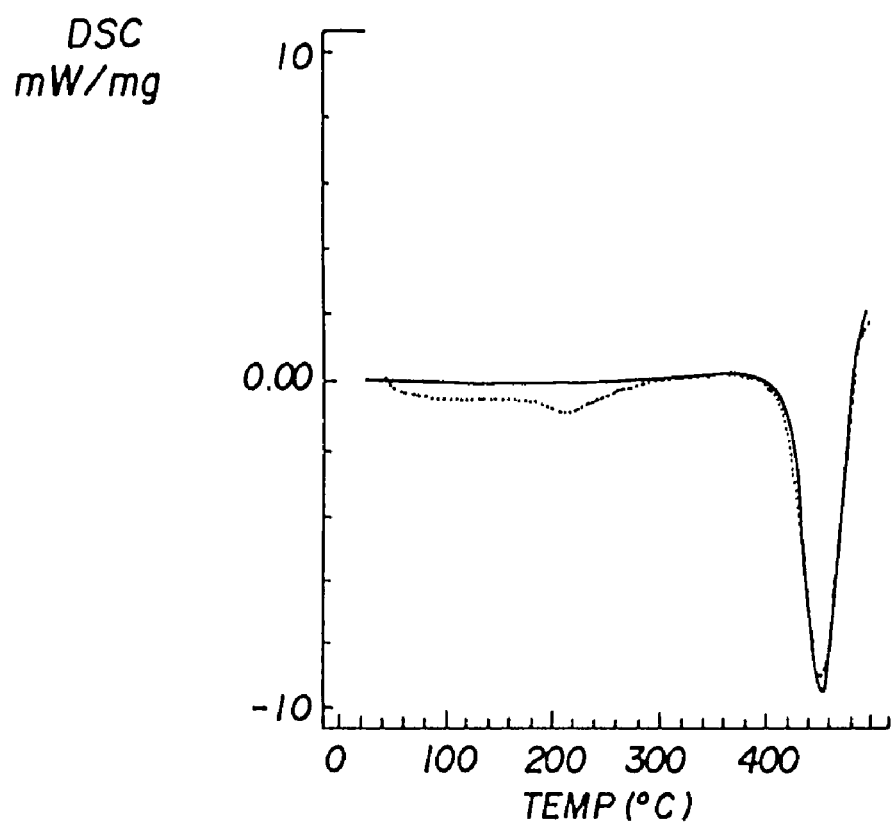
FIG. 32 is a graph which shows a calorimetry effect of Yoshixol on polystyrene 280,000, measured by a digital scanning calorimeter.
Figure 33:
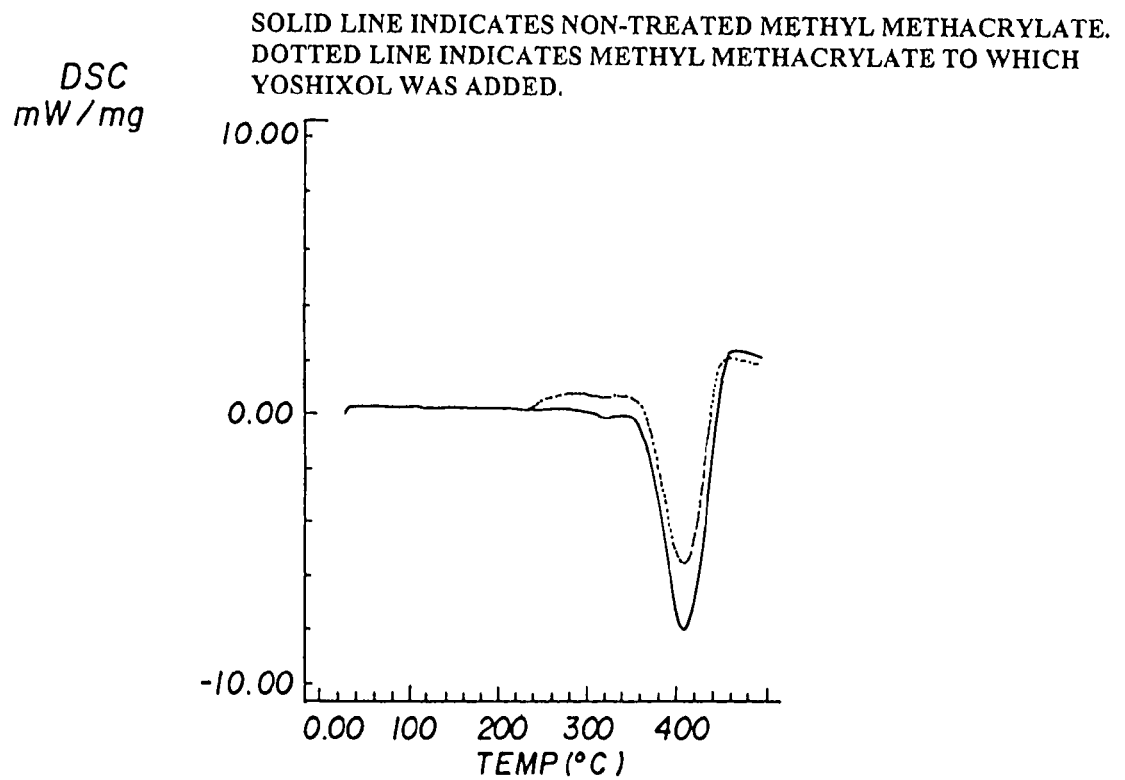
FIG. 33 are graphs which show calorimetry effects of Yoshixol on methyl methacrylate and ethyl methacrylate, measured by a digital scanning calorimeter.
Figure 33:
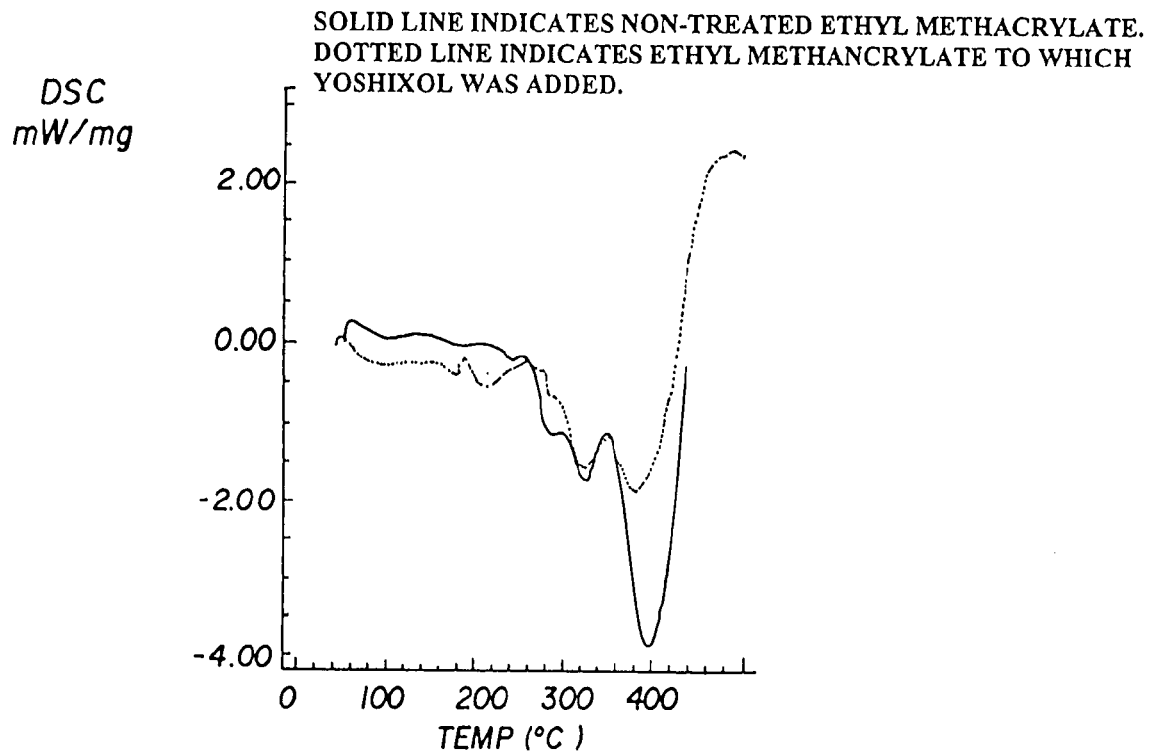
Figure 34:
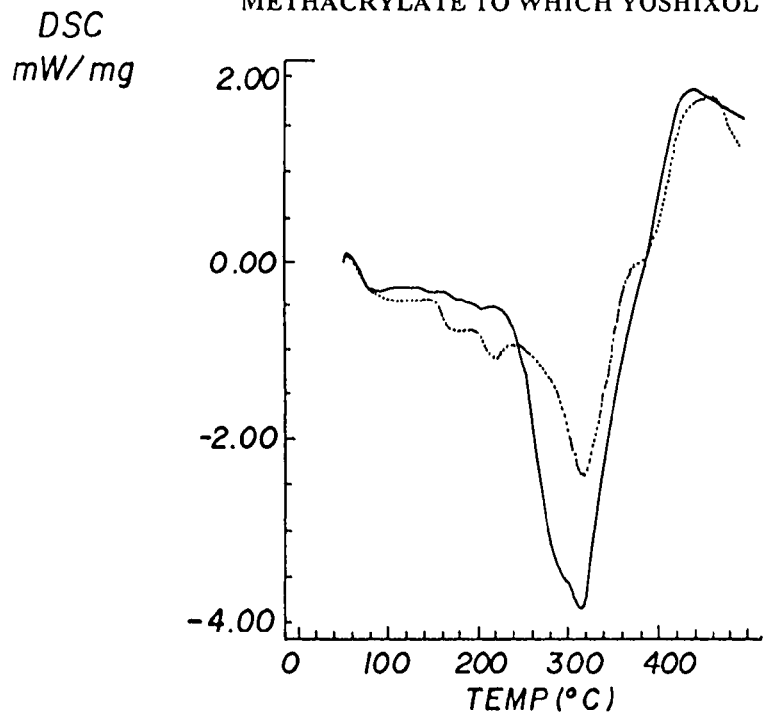
FIG. 34 are graphs which show calorimetry effects of Yoshixol on isobutyl methacrylate and poly(vinyl chloride), measured by a digital scanning calorimeter.
Figure 34:
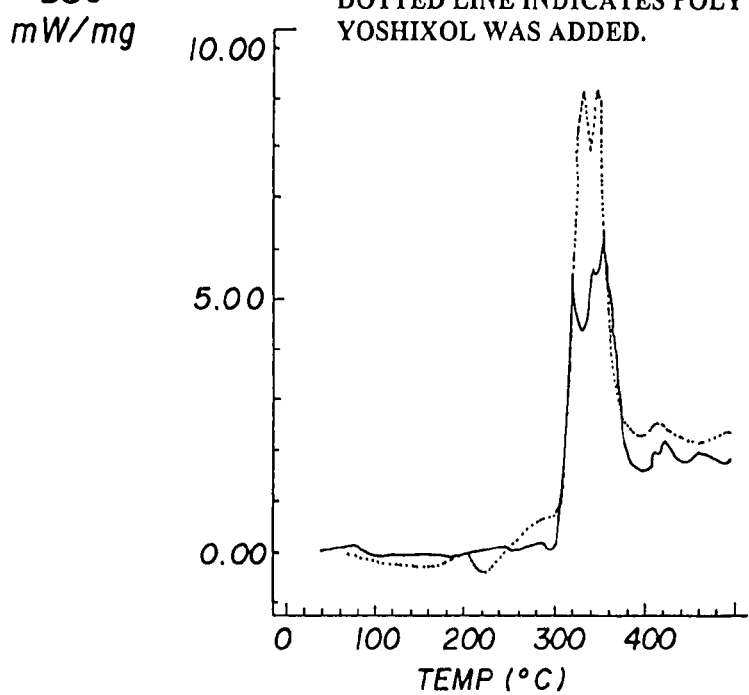
Figure 35:
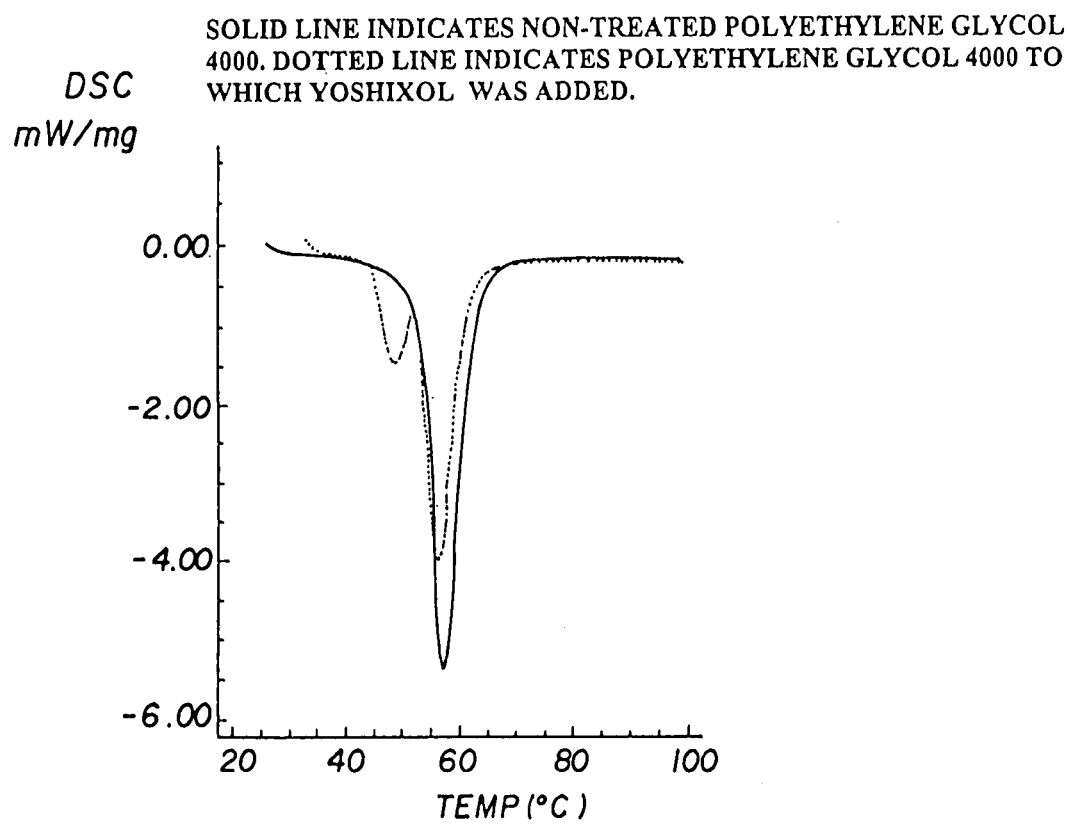
FIG. 35 is a graph which shows a calorimetry effect of Yoshixol on polyethylene glycol 4000 and poly(methylacrylate), measured by a digital scanning calorimeter.
Figure 35:
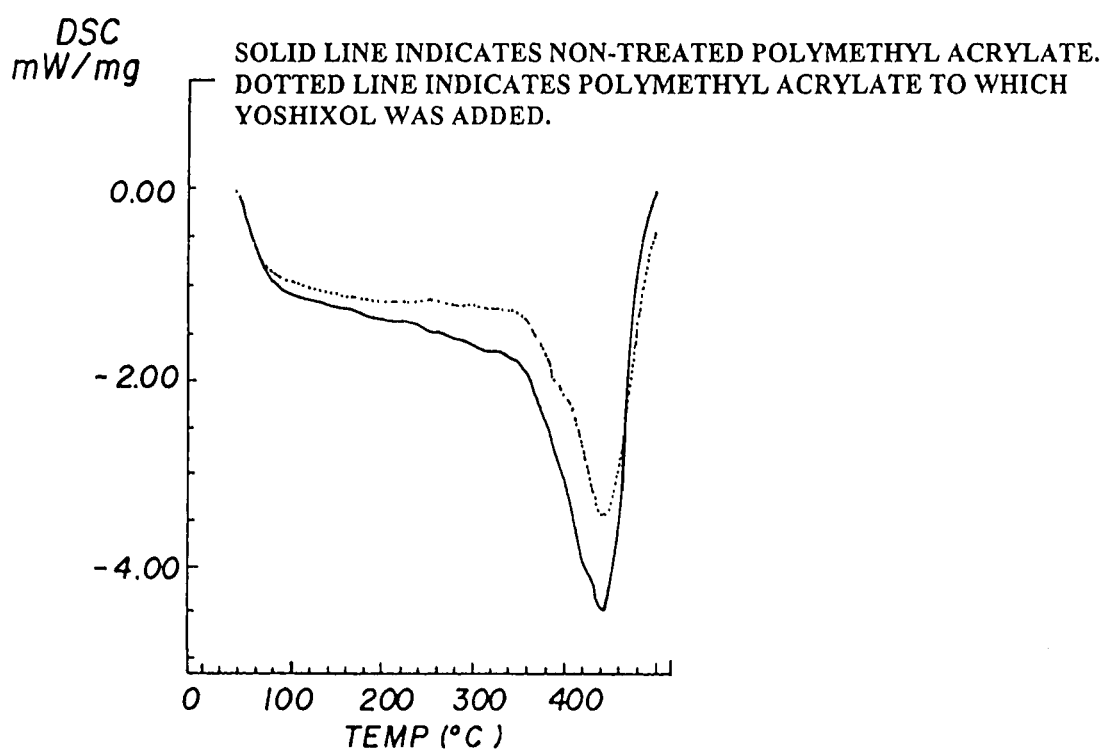

Moreover, since investigations above-mentioned were mainly parried by macroscopic observations, the microscopic observations were done to investigate effects on a change in physical property of each macromolecules. Changes in physical properties of macromolecules were measured by a digital scanning calorimeter (DSC-50, Shimadzu Seisakusho Ltd.). Data from the digital scanning calorimeter is displayed as a curve which is converted a signal of temperature deviation ($\Delta T$) from standard substance (at present measurement, alumina was used) against a time or a sample temperature so that area of the part which was enclosed between a base line and a peak is proportion to a thermal energy which is needed for a fusion of sample. Thus, since the thermal energy which was supplied to the sample at a constant pressure is identical with a increased amount of enthalpy in the sample, decrement effect of enthalpy of sample (decrement of heat capacity at constant volume and condensation rate) is displayed as a peak of falling downward on a phenomenon of changing physical property which is accompanying with a discontinuous change of the enthalpy against temperature such as the primary phase transition of a crystal and a fusion of sample. Therefore, peak area is regarded as a saltation quantity of enthalpy. Any change in a heat capacity measured by digital scanning calorimeter did not observe in stearic acid and lauric acid between before and after treatment. Though a slight fall of melting point was investigated in myristic acid and palmitic acid (100 µl of Yoshixol per each 100 g, referred FIG. 30), a large change in heat capacity was not found. On the other hand, an decrease in enthalpy between 20 and 60° C. on polyethylene glycol 1000 was disappeared after Yoshixol so that a phase which thermal capacity between 120 and 160° C. became a decrement reaction of enthalpy was found (referred FIG. 31). In polyethylene glycol 4000 with Yoshixol, a fall of melting point was observed. When 100 µl of Yoshixol was added in 200 mg of polystyrene 280,000, a phase of a decrement reaction of enthalpy around 30° C. and 280° C. was appeared (referred FIG. 32). When 200 µl of Yoshixol was added to 500 mg of methyl methacrylate, a decrement reaction of enthalpy between 230° C. and 340° C. was appeared though melting point did not change. Moreover, when 200 µl of Yoshixol was added on 500 mg of ethyl methacrylate, a decreased and increased reaction of enthalpy was inhibited as the whole (referred FIG. 33). Even when 200 µl of Yoshixol were added on 500 mg of isobutyl methacrylate, two peaks on an increase reaction of enthalpy between 60° C. and 250° C. were appeared newly and, an inhibition of maximal increase in enthalpy around 320° C. was found. In addition, a phase transition phenomenon was observed in macromolecules in acrylate group such as lauryl methacrylate and poly (methylacrylate) by treatment with Yoshixol. In 500 mg of poly(vinyl chloride) treated with 200 µl of Yoshixol, a decrement reaction of enthalpy around 300° C.-380° C. became to be about 2 times in comparison with the control (referred FIG. 34). When 100 µl of Yoshixol was added to 100 g of polyethylene glycol 4000, a new peak which shows an increase reaction of enthalpy between around 44° C. and 50° C. was found. When 200 µl of Yoshixol was added to 500 mg of poly (methylacrylate), an increase reaction of enthalpy in a range between 60° C. and 360° C. was inhibited (referred FIG. 35).

Figure 36:
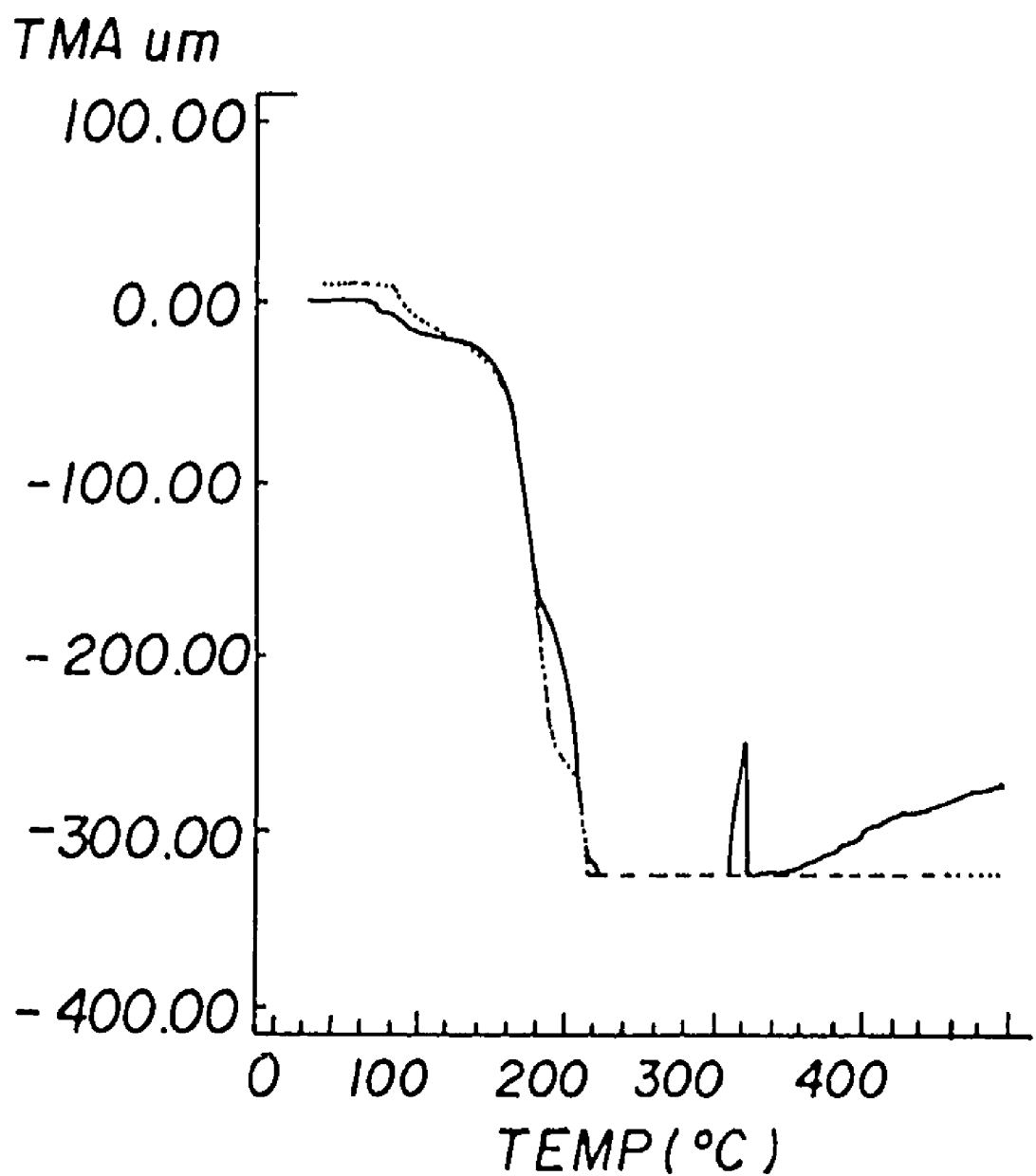
FIG. 36 is a graph which shows a thermal mechanical effect of Yoshixol on poly (vinyl chloride), measured by a thermal mechanical analyzer.

Moreover, when expansibility of poly(vinyl chloride) was observed by a heat machinery analysis equipment (TMA-50, Shimadzu Seisakusho Ltd.), an increased reaction of volume in the control sample was found around 315° C., however, an increased reaction of volume in 500 mg of poly(vinyl chloride) treated with 200 µl of Yoshixol was disappeared and a decrease in a condensation rate was found (referred FIG. 36). These results show that Yoshixol has a capacity which can improve a physical property with molecules and macromolecules, namely a thermodynamic property (for example, energy storage capacitance and internal energy state, change of structure due to change in entropy). And also, Yoshixol can improve a functional property which is induced or generated by structure of molecule and macromolecules.

<Effect on Changes in Molecular Weight of a New Synthesized Dimer with Seven Base Pair>

Figure 37:
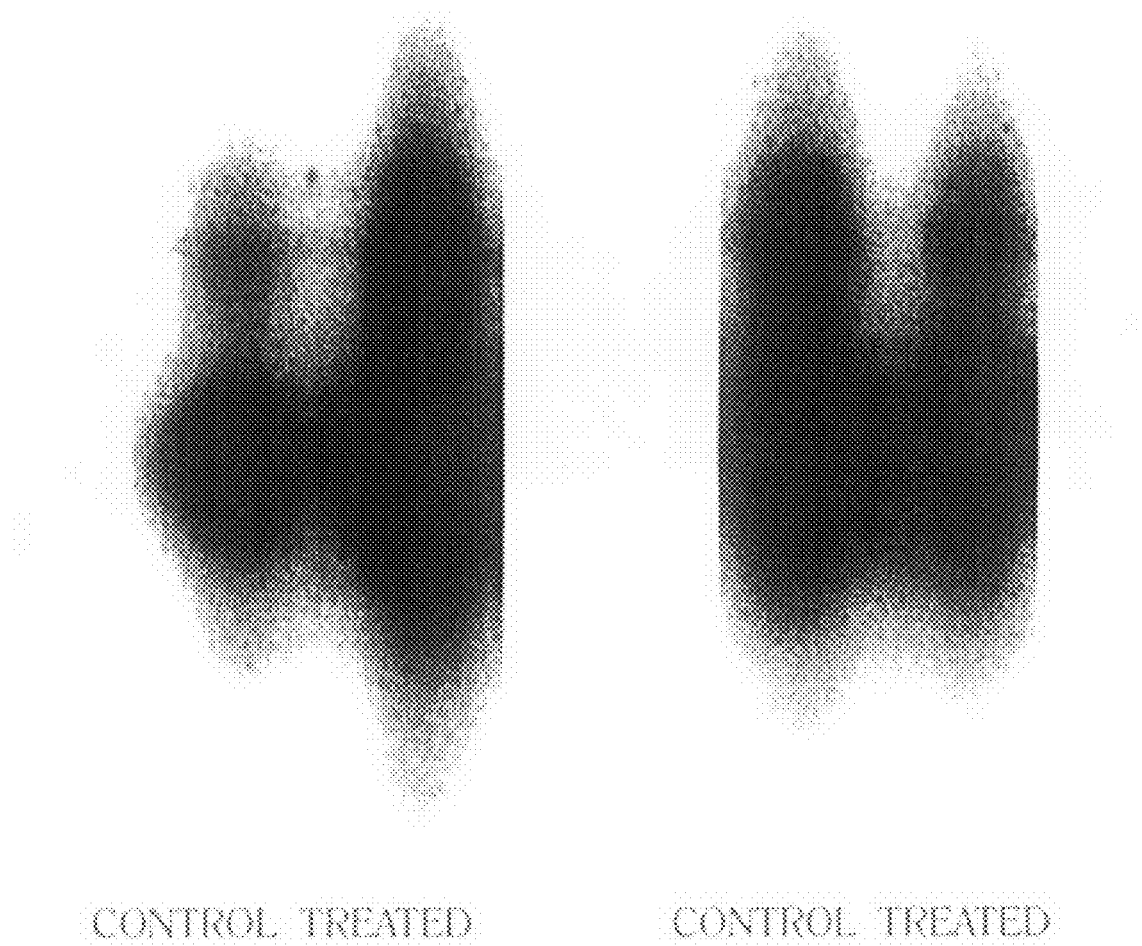
FIG. 37 is a picture of electrophoresis which shows the effect of Yoshixol on newly synthesized dimers with 7 base pairs.

DNA or RNA synthesis device (392-25 type, Perkin-Elmer Co.) was used and 7 base alignment (CTTCGGA) and (CTTCGGG) new synthesis dimer (SEQ ID NO: 1) (5'>CTTCGACTTCGGA<3') and (SEQ ID NO: 2) (5'>CTTCGGGCTTCGGG<3') were synthesized. Then, an effect of Yoshixol on a change in molecular weight of the dimer was investigated. This pellet was dissolved on 50 µl of tris EDTA, and OD260 was measurement by 100 times attenuation so that concentration was turned into equality (5 ng/µl) by tris EDTA and distilled water. And, 4 µl of an adjusted synthesis dimer was labeled at 5'-terminal end of the dimer with 4 µl of ATP which was labeled by P32. In addition, after processing the dimer with 1 µl of polynucleokinase (TaKaRa, Tokyo) for 30 minutes by 37° C., the solution was heated at 70° C. for 5 minutes. Afterward, 65 µl of tris EDTA, 1 µl of glycogen and 190 µl of chilled ethanol were added and were mixed. And, it was centrifuged over 10 minute by 16,000 cpm. After taking the supernatant out, the pellet was made dry. Again, it was dissolved by 50 µl of tris EDTA and, 1 µl of the solution with radioactivity was mixed with urea (15 g), acrylamide (5.7 g), bisacrylamide (0.3 g), tris boric acid EDTA (3 ml), 10% ammoniumpersulfate (0.1 ml) and N,N, N,N-tetramethyldiamine (15 µl) to distilled water, so that the volume was made to 30 ml in total. Then, 20% gels were made and the electrophoresis with constant voltage of 10 watt was performed to be exposed on a film. Changes in molecular weight with the dimers were investigated by the sample which was consisted of 2 µl of the solution which was dissolved by final tris EDTA with 2 µl of Yoshixol. As the control sample, 2 µl of distilled water was added to the solution. Then, each test sample was given 6 µl of the stop solution. Change in molecular weight of the synthesized dimers with Yoshixol did not differ from that without the treatment (referred FIG. 37). Therefore, this result shows that Yoshixol does not change a distribution of molecular weights with new synthesized dimers (SEQ ID NO: 1) (5'>CTTCGGACTTCGGA<31) and (SEQ ID NO: 2) (5'>CTTCGGGCTTCGGG<3') and does not change at least a primary structure.

<PCR Effect on DNA Template of a New Synthesis Dimer with Base Pair>

Figure 38:
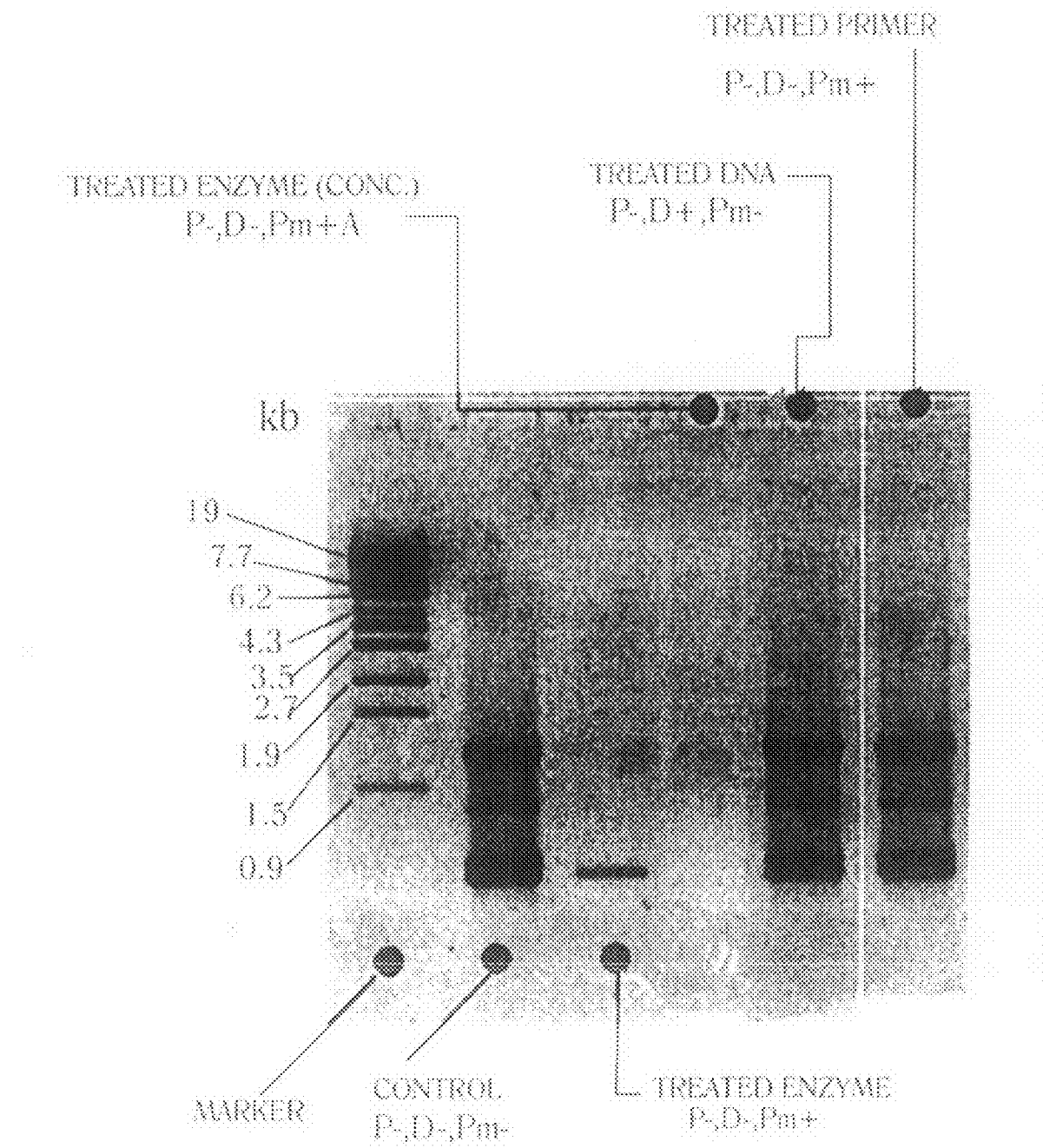
FIG. 38 is a picture of electrophoresis which shows the effect of Yoshixol on PCR of snake DNA by using a newly synthesized dimer of 7 base pairs as a primer.

Effect of Yoshixol on PCR was investigated by DNA template which was extracted from snake (blue-green snake, captured at Matsumoto city, Nagano). The new synthesized dimer of (SEQ ID NO: 2) (5'>CTTCGGGCTTCGGG<3') with 7 base-pair alignment (CTTCGGG) above-mentioned was used as a primer. PCR reaction was done by use of DNA thermal cycler (PJ-2000) made in PERKIN ELMER CETUS company. The following six combinations were prepared for the test samples. Those are two kinds of samples which consist of 5 µl of primer (100 pico mole/µl) with 5 µl of Yoshixol (P+) and without Yoshixol (P−). In addition, two kinds of samples which consist of 5 µl of snake DNA (500 ng/µl) with 5 µl of Yoshixol (D+) and without Yoshixol (D−). And, additional two kinds of samples which consist of 1 µl of polymerase enzymes (Recombinant Taq DNA Polymerase, No. R001A, TaKaRa Shuzo Co., Otsu city: 5 unit/µl) with 1 µl of Yoshixol (Pm+) and without Yoshixol (Pm−). After each sample was placed for 10 minutes at room temperature, each sample was diluted in distilled water. And, it is adjusted in a primer solution of 10 picomole/µl, DNA solution of 50 ng/µl and a polymerase enzymes solution of 0.5 unit/µl. Then, the following combinations were prepared. On PCR, a primer solution of 5 ml which is diluted mentioned above, 5 ml of DNA solution, 5 µl of buffer solution for PCR reaction, 0.25 µl of polymerase enzymes solution and 4 µl of dNTP mixed solution were added in distilled water to be made total volume of 50 µl. Combination of each sample is following five groups. First, each sample is not added Yoshixol as the control (P−, D−, Pm−). Second is the sample which only a primer has processed by Yoshixol (P+, D−, Pm−). Third is the sample which only DNA has processed by Yoshixol (P−, D+, Pm−). Fourth is the sample which polymerase enzymes alone has processed by Yoshixol (P−, D−, Pm+). In addition, fifth is the sample which concentration of Yoshixol for the polymerase is increased to 100 times on P−, D−, Pm+ series above mentioned (P−, D−, Pm+A). In each combination, amount of cDNA synthesis was amplified by a PCR method and was measured. On the group of P−, D−, Pm− which all samples were not treated, 4 bounds between a molecular weight of 0.5 and 1.2 kb were found. Also, the bounds in P−, D−, Pm− did not differ from those in P+, D−, Pm− and P−, D+, Pm−. But, on the group of P−, D−, Pm+, only one bound at lowest molecular weight within 4 bounds was appeared. In addition, any kind of bounds did not observe on the group of P−, D−, Pm+A (referred FIG. 38). This result shows that Yoshixol controls or inhibits functional generation of polymerase enzymes which is related to transcription and/or amplification of the base-pair alignment generated by DNA template which consists of many base-pair alignments. It is to be needless to say that inhibitory effects of molecular generating and/or inducing functions which was carried in claims 1-11 in this invention are not restricted by the primer which is new synthesized dimer (SEQ ID NO: 2) (5'>CTTCGGGCT-TCGGG<3'), snake DNA and polymerase enzymes demonstrated here.

<Effect of Yoshixol on a Change and a Modulation in Absorbance of Wavelength of Molecule with Pigmentums>

Figure 39:
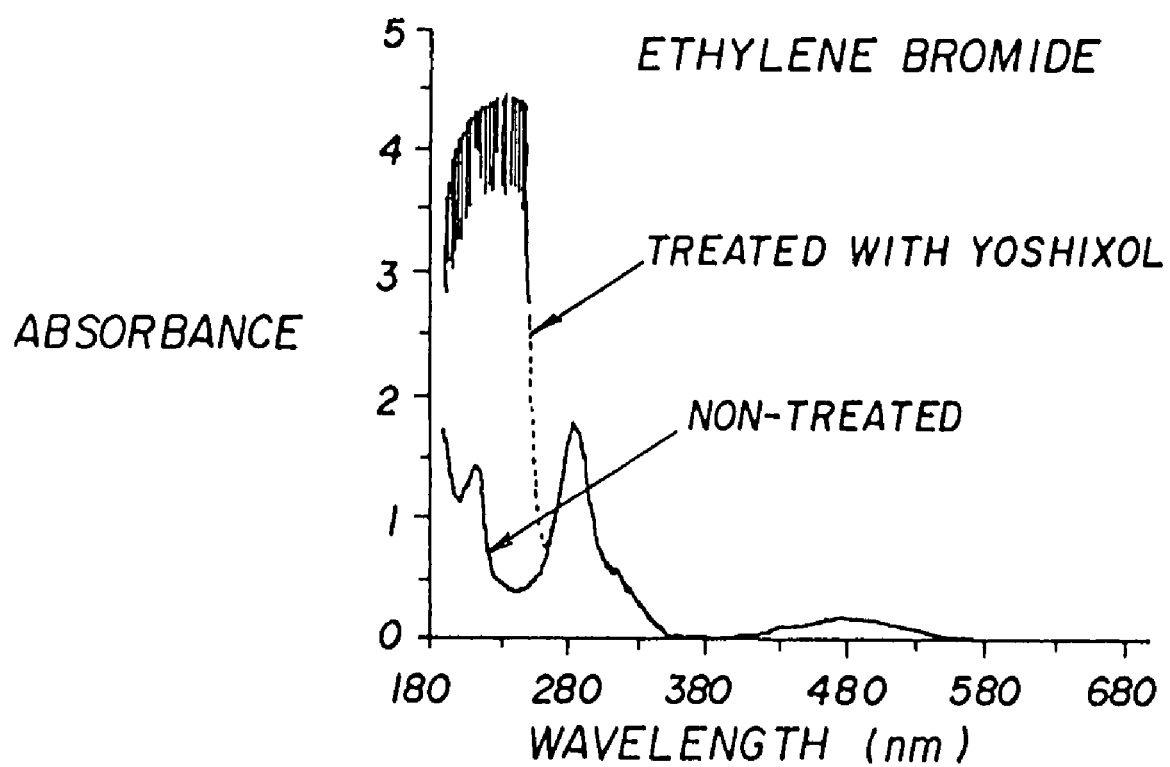
FIG. 39 is a graph which shows the effect of Yoshixol on change in absorbance of ethylene bromide, measured by a spectrophotometer.

In order to investigate an effect of Yoshixol on a change and a modulation of wavelength of molecular of pigmentums, eosin-5-iodoacetamide (Molecular Probes Inc., USA), evans blue (Wakou Jyunyaku Ltd., Osaka) and ethidium bromide (Molecular Probes Inc., USA) was used. After Yoshixol (10 µl) was added to 1 ml of eosin-5-iodoacetamide solution (10 mg/1 ml), 1 ml of evans blue solution (1 mol) and 1 ml of ethidium bromide solution (10 mg/ml), the absorbance was measured by a spectrophotometer (BIO SPECTRO, Beckman Co. USA). The fundamental wave length band which each pigmentums did not change with or without adding Yoshixol. And, though a quantitative and qualitative changes also did not found as well as the fundamental peak wavelength, a wave length band below 260 nm showed a great change. Especially, color of ethidium bromide with Yoshixol was observed to become a lack of transparence from a transparent dark and red. Such color after the treatment is observed by a naked eyes as almost a white and pink just like a ripe peach. In this case, major difference was found quantitatively and qualitatively in a wave length band between 270 and 200 nm which was measured by a spectrophotometer (referred FIG. 39). This result shows that Yoshixol can modulate a wave length band of pigmentums.

<Effect on Surface-Active Agents and/or Surfactants>

Moreover, effects of Yoshixol (50 µl) on surface-active agents and/or surfactants were investigated by use of 20 ml of each detergent for kitchen use commercially (for example, CHERMING, Lion Co.: NATERA, Lion Co.: MOA, Kao Co.), which consist mainly of alkyl ether sulfate ester sodium, fatty acid alkanolamido and polyoxyethylene alkyl ether. And, effects of Yoshixol (50 µl) on shampoos were investigated by use of 20 ml of each shampoo for hair washing use commercially (for example, PANTEN, Maxfacter Co.: LAX STYLING, Japan Riever Co.: ESSENTIAL STYLING, Kao Co.), which consist mainly of lauryl sulphate, paraven, cetyl alcohol, edetic acid, propylene glycol, polyoxyethylene laurylether sulphate. Each detergent and shampoo treated with Yoshixol became better foamed, better bubbled with sensitive texture, less adhesive and more bright colored, and it can wash out easily a soil of oiliness with a less amount of water. In addition, though a large difference on an aspect of each detergent and a shampoo which is added Yoshixol did not find, the viscosity of each detergent and a shampoo with the treatment decreased in the comparison with the non-treated one measured at 30° C. by a viscosimeter (Vismetron VEA-L, Shibaura System Co.) (referred Table 1). Moreover, a relationship of slip velocity-slip stress also decreased after the treatment. This result shows that an adding process of Yoshixol on a detergent and a shampoo which is already marketed can improve surface active effect and it's, property with a detergent and a shampoo.

TABLE 1

Change in Viscosity (CP) of Each Detergent Before and After Treatment with Yoshixol

|  | MORE | CHARMING | NATERA |
|---|---|---|---|
| Before | 66.9 | 62.2 | 70.2 |
| After | 62.9 | 53.3 | 63.5 |

<Effect on each Fatty Acid>

By adding 5 g of lauric acid (Wakou Jyunyaku Co., Osaka), 5 g of myristic acid (Wakou Jyunyaku Co., Osaka), 5 g of palmitic acid (Wakou Jyunyaku Co., Osaka), 1 g of linolic acid (Wakou Jyunyaku Co., Osaka), 5 g of stearic acid (Wakou Jyunyaku Co., Osaka) and 1 g of oleic acid (Wakou Jyunyaku Co., Osaka) into 50 ml of sodium hydroxide solution (1 N), a soapy substance was made (neutralization method). Then, the effect in the event that Yoshixol was added and investigated. A soapy substance with 50 µl of Yoshixol showed a property of better foamed, scarced, lavaged and less adhesive in comparison with a soapy substance without Yoshixol. Even though it was placed freely in a room over 6 months, a brown change did not occur in comparison with a soapy substance without Yoshixol. This result shows that Yoshixol is useful as antioxidants for a soap which is made from fatty acids, vegetable oil or animal oil, and that Yoshixol can improve and/or make better a property of soaps which is planed and manufactured freely.

<Concerning Acute and Chronic Toxicity>

In order to investigate a toxicity in vivo, the solution which was mixed 50 µl/Kg of Yoshixol with 1 ml of 20% glucose solution was administered intravenously in unanesthetized animals (rabbit and dog). After intravenous injection, transitional increase in respiration rate, increase in blood pressure and heart rate and active movements of an extremity (not convulsion) were observed for 1-2 minutes after the administration. Although an increases in a respiration rate and blood pressure remained during the observation period of 2 hours, an abnormal behavior was not found. On examination of blood, hyperchromic anemia at the maximum level occurred 3 days after administration followed by a recovery to the normal after 1 week. A change in platelets was not observed and, white blood cells increased 3 days after administration followed by a recovery to normal level at 1 week after administration. Though these animals were observed over 1 month, any abnormal behavior did not found. Also, after they were sucrified by intravenous injection of potassium chloride solution under deep anesthesia after 1 month, any pathological findings were not observed macroscopically and microscopically in the vital organs. This result shows that effect of Yoshixol is low toxic in vivo, and a side effect is less. Even though intravenous administration alone was done, it may be confirmed that it is safety.

Moreover, effects of chemical substance (4,4-dimethyl-2-cyclohexen-1-one) that all of substituent R1, R2, R3, R4, R5, R6 shown in general formula (1-b) and all of substituent R3, R4, R5, R6 shown in general formula (3-b) is hydrogen were investigated on all of parameters which were demonstrated by Yoshixol above-mentioned in this invention. As a result, this substance also provided to be able to control, inhibit and/or block function which is generated by multi-dimensional structure similarly to Yoshixol mentioned above. In addition, higher dosage was needed to be obtained qualitatively an identical effect to the above-mentioned effect of Yoshixol. Then, the concentration of 4,4-dimethyl-2-cyclohexen-1-one was required about 30-100 times dosage of Yoshixol on the biological samples, and about 10-50 times dosage of Yoshixol on lower molecular substance and macromolecular substance of non-living samples.

<Summary of Primary Effect and Mechanism, and its Significance>

Although it was demonstrated effects of Yoshixol as a representative compound in this invention, this invention is not restricted mentioned above by the demonstrating experiments which was shown here. This invention demonstrated a wide proofed effects and efficacies from a molecular level to the over all organism. To cite each reference about each scientific back-ground is far from the aim of this application so that the following two issues are cited as references of scientifically known events.

<ref. 1> by Bern and Levy, Physiology, Sanders Publishing Inc.:

<ref. 2> by Alberts, Ray, Lewis, Raff, Roberts and Watson, The Molecular Biology of the CELL, Garland Publishing Inc.:

As significance of this invention, it is the first time to provide possibilities with concrete examples to modulate a reaction process in molecular level and a function generated or induced by multi-dimensional structure which is produced by molecular-composed macromolecules. And, it is also the first time by concrete examples to provide possibilities to change function and/or block biological function witch is induced or generated by multi-dimensional structure which is constricted from macromolecules substances. Moreover, the significance in this invention is so great because that the provided compounds in this invention can inhibit and/or block function which is induced or generated by the multi-dimensional structure which had species difference of the cell membrane that is determined according each species evolutionally and is constructed for coexistence with the external world. And, the significance on scientific history is also great because it is clearly discussed that effects and mechanism of the compounds in this invention can understand by the theory of molecular orbital dynamics. In addition, the practical significance emphasized in this detailed description of this invention. The social significance in this invention is not only effects of the compounds, but also to be expected a necessary effect by use of the known mathematical simulation (for example, approximation of lone electron pair) concerning whether the compound is useful to human being or not, because that the compounds provided in this invention has extremely simple chemical structure. It is to be able to forecast sufficiently from demonstrating experiments in this invention and known scientific facts of molecular biology that for example, the effectiveness on the virus which is the filterable pathogenic microbacteria that is made up of macromolecules, namely on HIV infectious disease which is a worldwide problem at present time. Moreover, this invention has some suggestive ways coexistence between a human being including an environment on the earth and the nature as well as forecasting an interaction of drugs and an onset of side effects with combined use of drugs, and an early forecast of an appearance of the resistant strain and it's preventive step that is considered ecological system. The significance of this invention was darely carried because of eternal happiness of a human society and uncontroversial coexistence.

The brief comments of the logical explanation which is regarded as necessity to understood from claims 1 to claims 46 in this invention is carried following with both common mechanism as demonstrated in this invention, with distinguishing effects on living organism and substances as an inanimate object. However, it is needless to say that this invention is restricted by this description about the significance and mechanism. Thus, it is possible to explain effects of this invention integrately by interpreting mechanism of this invention on quantum theory of molecular orbital dynamics and thermodynamics. Then, it is widely known that each molecule has configuration, conformation and molecular orbital and, there is a space region corresponding to electron distribution. By an energy state on basis of molecule, it is possible to be explained the configuration of a molecule itself, physio-chemistry property and, interaction and a reaction rate of combining with distinctive molecule by the wave equation and the frontier theory of molecular orbitals. (bibliography: Yuki Denshi Ronn Kaisetu, 4th ed, by Minoru Imoto, Tokyo Kagaku Doujinn, 1990; Introduction of frontier orbitals, by Fleming, supervised by Kenichi Fukui, translated by Tomoda Takeuchi, Kodansha, 1992; How understand molecular orbital, 2nd ed, by Masayuki Yosida, Tokyo Kagaku Doujinn, 1992). And, a theoretical explanation of many chemical reactions can have been done by based on theory of organic electron, theory of molecular orbitals and quantum theory in organic chemistry for each molecule. For example, a rule of Woodward-Hoffman is also the one example. Generally, as it is away from atomic nucleus, existential density of electron changes and, a distance equivalent to the highest peak is a location that electron exists most abundantly (equilibration distance). Moreover, existential probabilities in an electron cloud which is in the location where generally electron can expand is determined following energy. It is the logical concept which this has systematized as quantum theory. On binding with of C and H (covalent bond) as one example of orbital with hybridization, if H and C can be overlapped, two electrons are coupled on both C and H. When two electrons turns a spin into reverse so that one bond is formed, the internal energy which an atom itself has gets lower and stabilization in order to release an enormous amount of the overlapping energy. Thus, binding energy is generated. In contrast, in order to make an original atom by splitting C—H bond, this binding energy must be added newly by some processes. Moreover, molecule has orbitals which is quantumized (There are constant orbital energy with discontinuity) between unstable orbitals and stable orbitals. Thus, it is known that a pair of two electrons enters into the orbital with a reversed spin from a stable orbital in order. With regard to an overlap of molecular orbitals, there is (+) and (−) phase so that molecules which have the same coincidence of phase only can be piled each other up, resulting in the stabilization. In contrast, if there is a phase difference as (+) and (−), it is also known that each molecule can not overlap so that each molecule is repulsed resulting in instability. Such matters is a basic theory of molecular orbitals. Moreover, though hydrogen ion is inscribed as $H^+$, H+ is proton itself. Thus, elementary particle can not be able to exist singly in a container such as a beaker and, it is very instable. Though this point is also ultimate knowledge in the science, there is even the important matters which is easy to be forgotten unexpectedly when life events is understood. Thus, an equilibration relation of "H$_3$O"$^+$ with H$_2$O are kept certainly in the place where water exists. This is important matter to need remembering when function is considered. In consideration of such theory of charge-transfer and molecular orbitals, it is extremely reasonable to grope a possibility which has at potency of control, inhibition and/or blocking of functional property and morphologic structure with functional macromolecules and living organism, so that this point consists of a part of logical basis concerning inhibitory effects of molecular generating and/or inducing functions, which was carried in claims 1-11 of this invention.

Moreover, on generation of σ combination in binding molecular orbitals, each s orbital was overlapped to become stable σ bind and, each sp orbital was overlapped on the same directional axis to become σ bind and, p orbital was overlapped to becomes bind when it stood opposite to each other on the same directional axis. In addition, on generation of π bond, p orbital becomes π bond when p orbital stood in a line in a parallel lengthwise. When it can not be matched, s orbital can not bond even if it is overlapped to p orbital with a different axis (in other words, atomic quadrupole moment). In addition, in regard to phase, p orbital on an identical x axis becomes σ bond and, p orbital on py orbital or px orbital become to be in parallel resulting in π bond. Since a direction of p orbital differs from py orbital and px orbital on right angle, the overlap does not occur. And, the binding does not occur when the phase differs between each molecule because of anti-bonding molecular orbital. In addition, electron isomerising effect (E effect) becomes in π bond with the double bond so that it differs greatly from that I effect is π bond. Because O group is the 6th group, if O group has six electrons which belongs to O itself, O group does not have an ability of proton discharging and electrically is neutral. However, for example, when O group has 7 electrons, electric charge on negative is naturally. This is fundamental and characteristic event of the carbonyl group which inhibitory or blocking agents of molecular generating and/or inducing functions which is carried in claims 1-11 of this invention. Moreover, delocalization of π electron and delocalization energy are also important. When π electron is distributed, the molecule becomes stable so that only amount of energy which became stable results in delocalization energy of electron. Carboxyl group, —C(=O)—OH, has the property or configuration that gives H+ to other molecule. As a second reason which is easy to discharge H$^+$, an anion which is —CO—O— after when H+ has been produced is distributed so that delocalization energy or resonance energy is generated. By discharging H$^+$, it can be stabilization still more. Thus, this state becomes to definitively reproduce the first factor that can release H$^+$. But, a formula of H$_3$O$^+$×OH$^-$=constant is usually made up of every aqueous solution including living organism. Such released proton is utilized as an internal energy for disordering in living organism with thermodynamic non-equilibration and opened system. The proton is utilized as ordering or stabilizing energy in proton receivable substances with thermodynamic equilibration and closed system. In order to inhibit or block each function (including molecule recognition) generated by multi-dimensional structure without changing the primary structure, it is ideal that the compound has a property of both electrophilic and nucleophilic nature and, the compound is neutral substance which has not a potency of releasing proton. On a reaction or σ-π interaction on π electron group, theory of frontier orbitals is an important concept that a reaction is definitive between interaction of HOMO molecular orbital and LUMO molecular orbital. For example, since double bond is formed from both σ and π bonds, a reaction is generated in the part which electron density is large. When "excitation" of carbonyl group is turned into an example, electron pair of π covalent bond which links between C and O by double bond is based on E effect and has a possibility to pull toward O. An addition of carbonyl group is called nucleophilic addition reaction. A property with "excitation" of carbonyl group is that oxygen takes electron so that more negative charges are easily increased. Though C=O has π bond, bonding molecular orbital with electron affects to anti-bonding molecular orbital of C=O group because that an anion has excessive electrons on a molecular orbital method. Thus, HOMO molecular orbital of an anion substance and LUMO molecular orbital of C=O result in a perturbation state. From this point of view, a part which a compound is easy to react depends on a magnitude of coefficient C of HOMO molecular orbital or LUMO molecular orbital and symmetry of phase with constituted atom orbital. In addition, an importance factor which dominates an activation energy of a chemical reaction is an electrical force on the basis of organic chemistry and electron theory. Thus, a polarization or electron transferring must occur in a reaction with neutral molecule so that it becomes important whether electron density in the reaction center is higher or lower. A substance concerned with morphologic formation and function of living organism produces a generation of function and a differentiation of function due to molecule recognition or in the region of reaction center by changing electron density due to conformations. In the frontier orbitals which is one of concepts that a magnitude of the activation energy which shows hardness of such a reaction is determined by the energy which is required to be localized π electron localization in a transition state, the position that occurs electrophilic reaction, nucleophilic reaction and radical reaction within one molecule is determined by the following. An electrophilic reaction at a basal state occurs in a position with highest density of two electrons which belongs to highest occupied molecular orbital (HOMO) and, a nucleophilic reaction occurs in the position of highest density when two electrons are stationed on lowest unoccupied molecular orbital (LUMO) at a basal state. A radical reaction occurs in the position which is largest sum of two electron densities when each electron is stationed on each HOMO and LUMO. In this way, the important factor which determines a chemical reaction is that as a condition of more stabilizing a reaction, it is needed to be consistent with symmetry between HOMO of an electron donative substance and LUMO of an electron acceptable substance. Thus, stabilization energy in the system is obtained only when symmetry between HOMO and LUMO is with the coincidence so that the chemical reaction becomes easy to be generated. And also, when a symmetry between LUMO and HOMO is different, it is thought to be hard to generate a chemical reaction because that a stabilizing energy in the system becomes zero by an interaction between HOMO and LUMO. Again, energy level of π electron is explained in the representative substances which is related on vital reactions. For example, an order from higher HOMO is of porphyrin>guanine>adenine>riboflavin>thymine>tryptophan>histidine. An order from lower LUMO is of histidine>guanine>adenine>tryptophan>riboflavin>porphyrin. Moreover, HOMO of both S compound (—SH) and NH2 are high so that those are also known to have a property which is easy to give electron. And also, in general, HOMO of S compound (—SH) is higher that that of NH2.

An intermolecular compound is made up of electron-pair donor (D) which gives electron to other substance and electron-pair acceptor (A) which receives electron from other substance. When D and A is mutually brought close, van der Waals force (attractive force between molecules) works firstly and a weak bond is produced between D and A. This state is termed as "non-bonding configuration" and is shown by A . . . D. In addition, when a distance between A and D becomes to be closer, each electron cloud begins to overlap so that a possibility of electron transferring is occurred. If one electron transfers to A from D, A-D bond is produced by forming a new pair of the electrons from these electrons in order to result from one unpaired electron. Since this state can be shown like A . . . D–, it is the state of "charge-transfer configuration" and is dependent on energy. Such an energy state modulates or change multi-dimensional structure of a substance and functional property. Thus, these structure and property are important to generate smoothly the function and to constrict living organism with morphogeneis, systematization and signal transduction via macromolecules from molecule as well as conformation, configuration and chiral of molecule as non-living organism. In addition, in order to simply understand thermodynamics of chemical and biological system, if a living organism and macromolecular substance is one of elastomers thermodynamically, a formula of $dE=TdS+fdL+\cdot N$ is realized. f is an extending force, L is a length and N is a number of chains or units or a number of monomers. On a closed system, N is uniformity. When two components are connected, shorter units are more advantage according to the formula of Wall's ideal gum model. If interaction between substances exist, it becomes more dramatic. In addition, when f is small, it is trend that units of most all becomes alpha type. When f becomes larger to the definitive level (critical temperature), units of most all suddenly change to beta type all together. Such phenomenon is called as phase transition. It is important to understood solation, gelatinization and liquid crystallization. In addition, when the second component is bonded, change in P2 (tension or volume) becomes to change in f resulting in triggering a phase transition even though f (force) is uniformity. Such event is called as allosteric effect. This effect is important in relation to generating function of living organism as well as macromolecules substances. Moreover, life events is not equilibration, and these are produced in the dynamic behavior. Because of this behavior, many interests are taken in a relation with the structure and function. An equilibration state of a reaction is that free energy remains unchanged by a reaction, in other words $dH-TdS=0$. dS is change in an entropy accompanied with a reaction. Rate of chemical reaction is to demonstrate quantitatively a change in speed of a chemical composition. A rate of reaction is function of concentration of the molecules which are constricted in the system so that the rate is dependent on on conditions such as temperature, tension or pressure, reaction container, catalyst, radiation and light. The general function is shown by $k=Ae-Ea/R$ when reaction rate is constant k. A is frequency factor and a exponential part is a probability which reaction molecule has an energy more than activation energy (Ea). On reaction of one molecule (single molecule), a reaction molecule itself does react automatically, and the activation is progressed thermally or by optical radiation. A rate of molecule which has an energy enough to react is identical speed to oscillation so that activated molecule reacts within 100-10 fentseconds.

In addition, it can be classified roughly into two factors. One is that activating energy dominates the rate. Another is that energy transferring is a main factor of the chemical reaction. A firing is the process which makes the radicals with unpaired electrons and atoms which dominate a reaction fundamentally. Since atoms and radicals are rich to reaction activity because of small activated energy of the reaction, chain reaction can be driven. The chain reaction is an important reaction that occurs in various steps such as combustion, pyrolysis of hydrocarbon and polymerization reaction. In order to understand physiological phenomenon, in addition, it is to be important. Moreover, a living organism is also constricted by carbon compounds. And, almost bonds between each atom of carbon compounds consist of covalent bonds in general. In order to cut the bond, energy must be added from the outside. And also, when numbers of carbon atoms increase, numbers of isomers progressively increase. From such a reason, it is said that a generating of life events on the earth is this optical isomer phenomenon.

Since configuration of macromolecules has spatial configuration (conformation) of macromolecules chain so that there is short-distance interaction and long-distance interaction (elimination volume effect) because that internal rotation of single bond is possible. For example, if linear macromolecules has only an interaction energy within molecule chains and entropy according to change in the structure of molecule chain is neglected, it is known that molecule chain produces helical structure. In addition, conformation is related to energy according to change in a bond angle between bond atoms, a van der Waals attraction force between non-bonding atoms, exchange repulsion according to overlapping electron cloud between atoms, interaction between dipole elements on polar group and ectrostatic interaction between ions and intramolecular hydrogen bond on ionized atoms. When structure is helical, energy is most stable so that it is also known that helical chain becomes aggregated crystal structure at a range of the temperature which molecule movement is not violent. An interaction between molecules is mainly a van der Waals attraction force, force according to overlapping electron cloud between atoms, intramolecular hydrogen bond and dipole interaction. Moreover, each block is coagulated by each other in copolymer so that microphase separation is caused. A size of this microphase separation is nanometer which is an order of molecule chain so that globular phase and rod-like phase produce a macroscopic lattice when treatment with an appropriate heat is performed. If molecule chain is possible to take an internal rotation likely as polyethylene and polystyrene, a structure of molecule chain is changed simultaneously according to a molecule movement so that it becomes random coil-like. A hard molecule chain such as polyamide in entire aromatic group takes rod-like structure. In molecule such as polyamino acid and DNA, rod-like structure occurs when helical structure is constricted by hydrogen bond. A random coil-like structure occurs when hydrogen bond is cut. Moreover, when a state of thermodynamic equilibrium of macromolecules is collapsed, the volume phase transition such as swelling and contraction appears. In addition, it is known that a natural phenomena to advances to a disorderly directions according to the second rule of the thermodynamics. In the event occurred spontaneously in non-equilibration system likely on living organism, entropy increases according to the second rule of the thermodynamics that an order formation is an acceptable direction thermodynamically. Though the ordering in natural phenomena is destroyed resulting in a direction of the disordering, it is in the theorem that the natural event which is found typically in life events creates the ordering itself. Though it is thought apparently that life events are contrary to a rule of physical chemistry, under a non-equilibration state such as biosis, it is the physical chemistry process whose such cosmos formation is natural and, it is proved by the theory of dissipative structures that the order formation is a natural process of physical chemistry under the non-equilibration system such as life events. This is developed the theory of self systematization phenomenon (formation of ordering structure) in physio-chemical system which is in the non-equilibrium state far from the equilibration state. If it is said simply, change in entropy (dS) in a system within a short interval (dt) is shown as a sum of an entropy (diS) which is caused in an inside of the system and a contributing entropy (deS) due to flow. It is dS=deS+diS. When there is in the steady state that the system is dS/dt=0, it becomes deS=diS<0. Thus, if negative entropy is supplied sufficiently to the system, spontaneous increase in entropy within the system is canceled resulting in ordering structure can be kept within the system.

Such status is to apply to life events. Living organism at any levels of cells, systematized tissues, organs and individuals are in the open and non-equilibration system. If the parameter of generation of entropy according to a nonplastic process is a generation rate of entropy according to a thermal flow, a generation rate of entropy due to flow of a substance and a generation rate of an entropy according to a chemical reaction, an affinity force is a difference of free energy between producing system and reacting system so that larger difference from equilibration takes bigger value, and when a chemical reaction has reached equilibration, a difference of free energy is zero. Therefore, generation of entropy is shown in (reaction rate)×(difference from equilibration in chemical reaction). In general, generation of entropy in a non-equilibrium state is understood as the total sum of (flux)×(thermodynamic force). The flux which is rendering here means flows such as a rate of chemical reaction, thermal flow and diffusion flow. Moreover, thermodynamic force is a driving force such as temperature difference, concentration difference (difference of chemical potential), affinity force of a chemical reaction. For example, if a small amount of a new phase which has a little difference from the original phase appeared when volume (V) and internal energy (E) is constant and, if this state is a state which is received perturbation and, if the newly produced phase is increased gradually, it is thought that the original system shall be disappeared. The original system is instable. A thermodynamic consideration of such change in the state show that if the system is a non-equilibrium state and, if increase in entropy occurred by the perturbation due to the second rule of the thermodynamics, a new phase is produced since it is assumed a local equilibration here. Therefore, a condition for the stabilization in the original system is required to be negative on changes in entropy due to perturbation. If it is restated, it is thought that the system which decreases temperature resulting in gradual absorption of heat (heat capacity at constant volume is negative) if heat is given, and which expands gradually expansion (compressibility is negative) if tension or pressure is given. However, it means that a fact is reverse. Moreover, an excessive generation of entropy is equal to an integrating value on the system as a whole of (difference of flux×difference of thermodynamic force) per unit time. It is shown usually to become negative. It is a universal expansive standard of Prigogine generally known as same as an proving a hypothesis under a local equilibration. When this relation is disturbed by some causes, a standard state becomes to be not stable so that it develops into a new state. This is the basis which an oscillation state causes from a steady state and which a new pattern (for example, functional polymers) is generated from the homogeneous distribution.

The biological effects of inhibitory or blocking agents of molecular generating and/or inducing functions which was carried in claims 1-11 in this invention can be explained with a logical acceptance by that morphogeneis, generation of function and molecular recognition as the fundamental phenomena of the life is in the open system with non-equilibrium under thermodynamics and molecular orbital methods as identical as demonstrated examples and logical interpretations of effects of inhibitory or blocking agents of molecular generating and/or inducing functions which was carried in claims 1-11 in this invention on molecules and macromolecules as non-living organism. As one example, though it is pointed out theoretically that an ideal property of anticancer drugs is necessary to have small entropy and large negative, or high binding enthalpy and low binding entropy without having Bay region, it has been dealt with the realization as the matter which is subtle and profound impossibility. Below, it is given an outline of the cell which is as fundamental structure in a general living organism, and of an thermodynamic and chemical importance of water which is major element of the organism. Finally, by demonstrating a value and property of electron localization of Yoshixol, as one of representative compounds, calculated by an approximation method, thermodynamic and chemical acceptability for the effects and its scientific significance are emphasized again.

Biomembrane is the fluid mosaic which is made up of saccharides, lipids and proteins, and has both properties of hydrophilicity and hydrophobicity. Moreover, in order to keep membrane function normally against a new environmental temperature in general, membrane fluidability is adjusted by changing in fatty acids compositions of membrane phospholipids. Biological effects of Yoshixol which were provided in this invention are appropriate from a series of results demonstrated by using each element of living organism in this invention, resulting in the speculating the appearance of thermodynamic effects with Yoshixol. Hydrophobicity interaction between hydrophobic groups is greatly committing into the stability of biomembrane. Hydrophobic side chain of amino acids lies buried inside into proteins, and it does not come in contact with water. And, it is also known well that multi-dimensional structure of proteins is maintained by hydrogen bond, hydrophobic interaction and van der Waals force, and that forms flexible matrixes. Such flexible and soft structure can change easily corresponding to the environmental condition which surround macromolecules. It has a reversible property that when a condition returns to an initial state, the original multi-dimensional structure recovers. The substance supporting this structure is hydrogen bond and hydrophobic interaction. By solvent except for water, such structure can not be produced. In such flexible structure and a state of random coil, entropy is large. In addition, hydrophobic interaction works between side chains so that hydration water around the side chains is pushed out outside of proteins molecules. For this reason, hydrophilic group of many amino acids is assembled on the surface of a globular proteins so that proteins can dissolve in water with their multi-dimensional structures. Though a globular proteins has the uniform multi-dimensional structure, it is alike with micelle of surface active agent since the outside of globular proteins assembles hydrophilic group and the inside hydrophobic group. Thus, a solvent with huger hydrophobicity is easy to connect proteins so that it is thought that conformation of proteins is changed in order that hydrophobic molecule embedded into the hydrophobic region near proteins surface. From such a chemical fact, when it is considered about structure and function of a cell membrane again, glycolipids are also important elements. While these saccharide chains operate as a discrimination and an adhesion between cells and a receptor of active factor or antigen molecule from the outside of cells, these play an active role on various kinds of functions such as cell prolifelation, differentiation, development and tissue morphogeneis. As a simple example, blood types of A, B, O are the phenomena which is generated in a different structure of saccharide chains which consist of glycolipids on the surface of an erythrocyte. It is also known that prolifelation of human cancer cells are inhibited by giving glycolipids. Inhibition of molecular generating and/or inducing functions of the compound which was carried in claims 1-11 in this invention can inhibit or block the physiological functions generated by multi-dimensional structure of saccharide chains resulting from changing their conformations.

Moreover, cell does not usually exist in a stationary position and, it is also known that cells shows various kinds of movements dependently on the species. While flagellum involves in motility of spermatozoa, cillium is a valid style of movement which a fluid is swayed along a cell surface. Energy source of such a movement is a flow of hydrogen ion. Though procaryotic cells are utilized hydrogen ion itself, an energy source of eucaryote is a flow of hydrogen ion produced by hydrolysis of ATP. At all events, these cellular movements depend on electron transferring which includes hydrogen ion. If these movements are thought as events of change in thermodynamic entropy, effects of inhibition on molecular generating and/or inducing functions of the compound was carried in claims 1-11 in this invention can explain the biological effects such as antimicrobacterial effect, anticancer effect, inhibitory effect on movement ability of spermatozoa which are demonstrated here by the thermodynamic effects. In addition, it is possible to explain effects of enzymes which are related with a chemical reaction within living organism from the point of function generated by molecular structure. For example, in order that the hydrogen atom which is connected on nitrogen atom of a pyrimidine ring on the side chain of histidine is dissociated around pH 7, it plays an important role in vivo of which pH is most accuracy. Then, the circumscription of the active site is the complementary with the substrate so that it can generate an adequate binding force due to interaction of van der Waals. Since interaction of van der Waals is reciprocal proportions on a distance to the seventh, a strong attraction force operates between each space when the surface which can contact exactly exists. Moreover, there is the space which is surrounded by hydrophobic residues in active site of enzymes (for example, trypsin, chymotrypsin and elastase) which serine residue exists in active site such as serine enzymes. The large side chain with residue of C-terminal of the substrate is settled in this space so that residue with large side chain of hydrocarbon and with aromatic series becomes easy to hydrolysis. Moreover, pepsin can hydrolyze a peptide bond which exists between residue with large side chain of hydrocarbon or with aromatic series. But, a rate of hydrolysis is influenced by the secondary residue as well as a next residue of bond which is cut. Moreover, it is also known that SH group of cysteine such as cysteine enzymes operates with an imidazole ring of histidine. Effects of inhibition on molecular generating and/or inducing functions of the compound which was carried in claims 1-11 in this invention can explain the biological effects from the thermodynamic effect and chemical kinetics.

Additionally, based on above-mentioned explanation of mechanism, the intracellular structures are supported by cytoskeleton, which major elements are actin, microtubles and intermediate filament. This cytoskeleton plays a important role on mitosis and prolifelation, and cell death as well as morphologic formation and maintenance. The components which consist of cytoskeleton are generated each biological function by polymerization and depolymerization. For example, though on actin fiber, half of actin within cell is remained as monomer with molecular weight of 42,000, the rest of actin is polymerized resulting in fibers with a diameter about 8 nm. Thus, equilibration is formed between monomers and fibers so that it is on the dynamic equilibrium state that one side of actin fiber becomes to be elongated by polymerization and another site to be shorten by dissociation. As for either, it is pointed out that a diversity on morphogeneis and generation of biological functions is produced by taking multi-dimensional structure. In addition, microtubles and microfilaments which constructs cytoskeleton differ greatly from intracellular organella such as nucleus, chromosome, mitochondria. Though latter one is stabilized, the former is generated newly and is disappeared dependently on the conditions. Thus, microtubles and microfilaments are structure "which is moving" so that it is not stabilized with an uniform structure forever, and it is dynamic. Moreover, to shorten means that tentacle does not contract, but that a length of microtubles becomes short on the base of tentacle, resulting from that microtubles being broken rapidly to proteins as the constructed units on the basic part of microtubles because of degradation (depolymerization) of microtubles to be in tubulin. It is thought that existence of the normal cells is in a suitable equilibration relation (dynamic equilibrium state which is balanced with mutual fluctuation) between the polymerization and depolymerization. Using such a fact, there is a proposal of a compound which inhibits cell-division and prolifelation by promoting the polymerization (for example, taxol). On reverse, it is also possible theoretically to inhibit prolifelation of such cancer cells by promoting effect of the depolymerization as thermodynamic non-equilibration system. The inhibitory agents of molecular generating and/or inducing functions which was carried in claims 1-11 in this invention can be explained the biological effects by property such as thermodynamic effect and hydrophobicity as well as nucleophilic and electrophilic property, resulting in thermodynamic orderings such as change in conformation and phase transition readjust a turbulence of a dynamic equilibrium state in the living organism.

In addition, it is the important factor which is easy to be forgotten, although it is known well that major element of the living organism consists of water. Thus, it may be thought that any intracellular or intracellular environment is also a state of a concentrated solution. It is the main factor which causes phase transition mentioned above. If the biological substances is considered as such an aqueous solution, a heat movement of hydration water surrounding of hydrophobic group becomes slow. As it is identical, a rotation of water molecule surrounding hydrophobic group is also late. Since a hydration process is completely different from hydration of sugar, ion and OH group, it is called with hydrophobic hydration. Thus, a state of a solution reverses a role of a solute and a solvent by the concentration. Essential qualities of a heat movement of molecule in a hydration state is a disorderly state. That change in entropy is negative shows that entropy of hydration water with hydrophobic substance is smaller than that of bulk. Moreover, the state which entropy is low is not a suitable state thermodynamically. When the molecule which has enough hydrophobic group dissolves in water, these hydrophobic groups assemble so that entropy of entire solution becomes larger by pushing out the water molecule which contacts with hydrophobic group. It can be thought that this hydrophobicity interaction makes micelle of surface active agent on assembly. This hydrophobic interaction is important for living organism.

It is also important to study dynamics of water within such living organism for understanding of biological life events as well as medicine. For example, it is thought that a longer time of an alleviation time among cancer tissue is to change conformation of biopolymers. A heat movement of water in a cancer cells is faster than that of water in the normal tissues. For this reason, if there is a neutral substance which promote structuring of suitable water, it becomes possible to inhibit prolifelation of a cancer. It is clear that a relaxation time of proton of water among tissues such as inflammatory edema associated with bacteria infection, virus infection, allergy (atopy) reaction, edema associated with circulatory disturbance and edema on gastroenteritis and gastric ulcer as well as cancer differs from that in normal tissue. Water molecule within the cell has a movement at range between 10 picosecond and 10 nanoseconds so that it is late more than 10 fentseconds of a movement state of water molecule in an extracellular fluid and bulk water. When heat movement is violent, entropy is larger. Thus, it can be said that the structuring water is at the state which entropy is low.

From several scientific facts mentioned above, Yoshixol which is provided by the representative experiments in this invention has the following property of molecular structure (referred Table 2). In other words, 1) it does not have a cyclic electron cloud and π electron density is localized between the double bond around carbonyl group.
2) There is a gap (difference) of HOMO-LUMO, and the reactivity with electrophilic property (amino group and hydroxyl group) and the reactivity with nucleophilic property (proton and carbon cation) are large.
3) Though polarization on carbon atom of carbonyl group (1') is positive and that on oxygen atom is negative concerning to charge distribution, it does not have an ability of proton release and is a neutral molecule.
4) It has methyl group which is alkyl group (hydrophobic structure) on the opposite side of a position of carbonyl group.
5) It has a mirror symmetrical structure stereoscopically. In addition,
6) It does not have Bay region.

With properties mentioned above, It is thought that Yoshixol inhibits function which is generated by conformation of molecule as well as multi-dimensional structure formation of a substance and a functional property by non-structurization of the water molecule which is related to structuring.

TABLE 2

Charge Distribution of Yoshixol Calculated by STO-3G Approximating Method, and Coefficients of HOMO and LUMO.

|  | Charge Distribution | Coefficient of HOMO | Coefficient of LUMO |
| --- | --- | --- | --- |
| =O of 1-position | −0.22654 | −0.47279 | +0.58440 |
| C of 1-position | +0.17523 | −0.21573 | −0.46107 |
| C of 2-position | −0.09785 | +0.36526 | −0.27047 |
| C of 3-position | −0.04393 | +0.37883 | +0.46417 |
| C of 4-position | +0.00415 | −0.05417 | +0.00311 |
| C of 5-position | −0.10435 | −0.06063 | +0.00470 |
| C of 6-position | −0.01661 | +0.34910 | −0.27305 |
| =CH2 of 6-position | −0.22654 | +0.40233 | +0.44858 |

It is thought that the fundamental mechanism concerning on inhibitory agents of molecular generating and/or inducing functions which was carried in claims 1-11 in this inventions is to alter a thermodynamic state of a substance and/or a state which is reacted with an acceptor side according to thermodynamic entropy, an expansion operation of this entropy, force and length (tension or volume), numbers of combination (quantity of probability quantity) and interaction between each factor. This generation of thermodynamic change such as increasing effect of entropy is compatible not only to a substance with thermodynamic equilibration and closed system but to living organism with thermodynamic non-equilibration and opened system. Thus, it is suggested that it is possible to modulate, change or improve a property of a substance multi-dimensionally in both of living organism and non-living substances. For this reason, by darely elaborate on a scientific logic and validity about this mechanism, historical significance on science as well as industrial significance are emphasized in more details although there are several repetitions. Thus, the significance in this invention was clarified. The intermediate compound of 4,4-dimethyl-2-cyclohexen-1-one, which substituent R3, R4, R5, R6 in general formula (3-b) are hydrogen atom, is known that it has a effect as antifungal agents, antiandrogen agents, fragrant agents and reagents for optical activity (Japan patent No. S 50-105841, Japan patent No. S 51-105038, Japan patent No. H 4-316531, U.S. Pat. No. 4,081,458, U.S. Pat. No. 5,169,993, Switzerland patent No. 603071). But, it is not restricted about the following effects based on the logical mechanism, chemical compounds and their derivatives which can inhibit or block induced or generated by multi-dimensional structure (conformation) in general formula of (1-a), (1-b), (2), (3-a) and (3-b) represented in this invention and which are disclosed in this invention. The effects are the following ones; antifungal agents, anticancer drugs, fragrant agents, reagents for an optical activity, antibacterial agents, antiviral agents, bactericidal and/or sterilized agents, anticoagulants and/or antifibrinolytic agents, blood coagulation and fibrinolysis blocking agents, spermatocidal agents, contraceptive agents for external use, thrombolytic agents, conformation altering agents of saccharide-chains, agents for preventing arteriosclerosis, metabolism (lipids, sugar, proteins) improving agents, agents for wound healing, epithelialization promoting agents, inhibitory agents for function of bioactive substances (enzymes, peptides, genes), blocking agents for function of bioactive substances, inhibitory and/or blocking agents of antigen-antibody reaction, organ and tissue preservative and improving agents of physical property of bonds (for example, chain reaction polymerization, sequential reaction polymerization, radical vinyl polymerization, polymerization inhibition, copolymerization, configurational polymerization, sequential polymerization, space lattice polymerization, cross-linking reaction) with non-biological substances (for example, phospholipids, glyceryl group, sulfudoryl group, thiol ester group, monosaccharides, disaccharides, polysaccharides, silicones, vinyls and celluloses). Additional effects are improving agents of physical property according to effects such as methylation of carbohydrates, peptide bond of amide group, a synthesis of soluble globular proteins, stereochemical space recognition and control of substances, micelle formation of lipids. Moreover, the substance is the organic compound which contains effective ingredients with an emulsificating effect of other substance. In addition, another effects of the compound are depolymerization agents, improving agents for surface active substances, phase transition agents, improving agents of phase transition, improving agents of microphase separation, plasticity and/or elasticity promoting agents, plasticity and/or elasticity improving agents (plasticizers), copolymerization agents, copolymerization improving agents, polymerization regulators, improving agents of polymerization adjustment, stabilizers, stabilization improving agents, improving agents of crystallized materials and/or amorphous materials, fluidability improving agents, flexibility promoters, improving agents for changing flexibility, antioxidants, improving and/or modulting agents for fluorescent wavelength and excitation wavelength of pigmentums, coating materials or colorants, improving agents of physical property of low molecule substances, function improving agents of low molecule substances, improving agents of physical property of macromolecules substances, function improving agents of macromolecules substances, improving agents of physical property of macromolecules composite materials and of functional macromolecules composite materials. For example, it can be forecast clearly that the compound can make sensitization, decoloring or tinction of various pigmentums with each metachromatism from the effects of changing a stereochemical structure with photogenetic group.

Those are pigmentums (for example, chalcone, flavone, anthocyanidin and/or aurone) of flavonoid group, pigmentums (for example gentisin and/or lichexanthone) of xanthone group, pigmentums (for example, benzoquinone, siperaquinone, embelin, methaquinone, pulvinic acid, coprinine, roson, juglone (5-hydroxy-1,4-naphthoquinone), lomatiol, anthraquinone, anthrone, alizarin and/or agate azine) of quinone group, pigmentums (for example, crocetin and/or carotene) of carotinoid group, pigmentums (for example, porphine, chlorin, foruvine and/or chlorophyll) of chlorophyll group, pigmentums of phycobilins group, pigmentums of petaleine group, pigmentums of melanin group, pigmentums of synthesized organic compound group.

EXAMPLES OF FORMULATION

Below, an example of formulation is given concretely and is explained.

Formulation Example 1

Cream Agents (Burnishing Type)

As one of a making example of cream agents (burnishing type), the following substances are mixing first of all; Yoshixol (0.3 ml), citric acid-1-hydrate (0.5 ml), polyethylene pyrene glycol (4.5 ml), distilled water (67.7 ml), cetyl alcohol (4.0 ml), stearic acid (10.0 ml), hard paraffin (2.0 g), myristic acid octlydodecyl (5.0 ml), myristic acid isopropyl (5.0 ml), glycerylmonoolate (0.5 ml). Afterward, it is heated by about 80° C. to be dissolution, and an emulsification is performed so that a vanishing cream (O/W emulsion) can be obtained.

Formulation Example 2

Ointment Type

Yoshixol is added to liquid paraffin to be distributed. If this is mixed enough in addition to plastibase, ointment (ointment with oiliness) which consists of 0.3 weight % of Yoshixol can be obtained.

Formulation Example 3

Tablet Type

This tablet and capsule may be able to be coated by easily soluble film coating agents (for example, polyvinylacetaldiethylamino acetate) and edible colorants which is usually used when it needs.

Formulation Example 4

Injection Type

Agents for injection are dissoluted by a little amount of ethanol when it is needed and is obtained by combining with the injection fluid (for example, 20% glucose solution) which is usually used. Though examples of formulation in this invention was explained above, this invention is not restricted by above-mentioned examples of formulation. It is suitably needless to say that it is able to be altered by adequate applications when it is necessary to be changed within the summary in this invention.

The invention claimed is:

1. A method for inhibiting or blocking molecular generating and/or inducing functions of a substance comprising contacting said substance with an inhibiting or blocking effecting amount of a compound represented by formula 2:

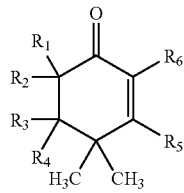

(wherein
- (i) R1, R2, R3, R4, R5 and R6 represent independently hydrogen atom; halogen atom; C1-C6 alkyl group; amidino group; C3-C8 cycloalkyl group; C1-C6 alkoxy C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group;
- (ii) one or more of R1, R2, R3 and R4, and/or one or more of R5 and R6 may be substituted or non-substituted cyclopentyl group; substituted or non-substituted cyclohexyl group; or substituted or non-substituted naphthyl group;
- (iii) R5 and R6 may form a ring by binding with another condensation polycyclic hydrocarbon compound or heterocyclic compound;
- (iv) one or more of R3, R4, R5 and R6 may be substituted by one or more of substituents selected from the group consisting of halogen atom, cyano group, protected or non-protected carboxyl group, protected or non-protected hydroxyl group, protected or non-protected amino group, C1-C6 alkyl group, C1-C6 alkoxy group, C1-C7 alkoxy carbonyl group, aryl group, C3-C6 cycloalkyl group, C1-C6 acylamino group, C1-C6 acyloxy group, C2-C6 alkenyl group, C1-C6 trihalogenoalkyl group, C1-C6 alkylamino group, and C1-C6 dialkylamino group;
- (v) R2 and/or R5 may be substituted by one or more substituents selected from the group consisting of halogen atom, C1-C6 alkyl group, protected or non-protected carboxyl group, protected or non-protected hydroxyl group, protected or non-protected amino group, protected or non-protected C1-C6 alkylamino group, protected or non-protected C1-C6 aminoalkyl group, protected or non-protected C1-C6 alkylamino C1-C6 alkyl group, protected or non-protected hydroxyalkyl group, and C3-C6 cycloalkylamino group;
- (vi) when one or more of R3, R4, R5 and R6 are alkyl groups, terminal end(s) of the alkyl group(s) may be substituted by C3-C8 cycloalkyl group).

2. The method according to claim 1, wherein
said aryl group in (i) and (iv) is phenyl, tollyl, xylyl or naphthyl group;
said substituted cyclopentyl group in (ii) is cyclopentylamino group or cyclopentylcarbinol group, said substituted cyclohexyl group in (ii) is cyclohexylamino group, cyclohexylaldehyde group or cyclohexyl acetic acid group, and said substituted naphthyl group in (ii) is naphthylamino group or naphthylamino sulfonic acid group; and
said condensation polycyclic hydrocarbon compound in (iii) is pentalene, indene, naphthalene, azulene, heptalene, biphenylene, indacene, acenaphthylene, fluorene, phenalene, phenanthrene, anthracene, pentacene, hexacene, dibenzophenanthrene, 1H-cyclopentacyclooctene or benzocyclooctene, and said heterocyclic compound is furan, thiophene, pyrrole, g-pyran, g-thiopyran, pyridine, thiazole, imidazole pyrimidine, indole or quinoline.

3. The method according to claim 1, wherein said method is for inhibiting growth of bacteria.

4. The method according to claim 1, wherein said method is for inhibiting growth of fungi.

5. The method according to claim 1, wherein said method is for inhibiting proliferation of viruses.

6. The method according to claim 1, wherein said method is for killing bacteria and/or for sterilization.

7. The method according to claim 1, wherein said method is for inhibiting growth of cancer and/or tumor.

8. The method according to claim 1, wherein said method is for inhibiting coagulation and/or fibrinolysis.

9. The method according to claim 1, wherein said method is for inhibiting and/or blocking antigen-antibody reactions.

10. The method according to claim 1, wherein said method is for preserving organs and/or tissues.

11. The method according to claim 1, wherein said method is for antisepsis and/or preservation.

12. The method according to claim 1, wherein said method is for indicating a targeted position of generating function of molecule by using a substance represented by the formula 2, which substance is labeled.

13. The method according to claim 1, wherein said method is for reduction.

14. The method according to claim 1, wherein said method is for scavenging free radicals.

15. The method according to claim 1, wherein said method is for desulfurization.

16. The method according to claim 1, wherein said method is for depolymerization.

17. The method according to claim 1, wherein said method is for improving functional and/or physical properties of surfactants.

18. The method according to claim 1, wherein said method is for killing sperms and/or for external contraception.

19. The method according to claim 1, wherein said method is for thrombolysis.

20. The method according to claim 1, wherein said method is for altering conformation of saccharide chains.

21. The method according to claim 1, wherein said method is for preventing arteriosclerosis.

22. The method according to claim 1, wherein said method is for improving metabolism of lipids, sugars and/or proteins.

23. The method according to claim 1, wherein said method is for healing wounds and/or promoting epithelialization.

24. The method according to claim 1, wherein said method is for restoration of hair.

25. The method according to claim 1, wherein said method is for phase transition or for improving phase transition.

26. The method according to claim 1, wherein said method is for improving microphase separation structure.

27. The method according to claim 1, wherein said method is for improving plasticity and/or elasticity.

28. The method according to claim 1, wherein said method is for copolymerization of for improving copolymerization.

29. The method according to claim 1, wherein said method is for regulating polymerization or improving polymerization adjustment.

30. The method according to claim 1, wherein said method is for preventing oxidation.

31. The method according to claim 1, wherein said method is for improving fluidability or fluidity.

32. The method according to claim 1, wherein said method is for softening or improving softness or flexibility.

33. The method according to claim 1, wherein said method is for modulating and/or improving fluorescent wavelength and/or excitation wavelength of pigments, coating materials, paints or colorants.

34. The method according to claim 1, wherein said method is for improving functional and/or physical properties of low molecular substances.

35. The method according to claim 1, wherein said method is for improving physical properties and functions of macromolecular substances.

36. The method according to claim 1, wherein said method is for improving physical properties of macromolecular composite materials and functional macromolecular composite materials.

* * * * *